(12) United States Patent
Hinuma et al.

(10) Patent No.: US 7,041,789 B2
(45) Date of Patent: May 9, 2006

(54) RFRP-3 AND DNA THEREOF

(75) Inventors: Shuji Hinuma, Tsukuba (JP); Hiromi Yoshida, Ishige-machi (JP); Yugo Habata, Tsukuba (JP); Masaki Hosoya, Tsuchiura (JP); Chieko Kitada, Sakai (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 117 days.

(21) Appl. No.: 10/487,634

(22) PCT Filed: Aug. 22, 2002

(86) PCT No.: PCT/JP02/08466

§ 371 (c)(1),
(2), (4) Date: Feb. 24, 2004

(87) PCT Pub. No.: WO03/018795

PCT Pub. Date: Mar. 6, 2003

(65) Prior Publication Data

US 2004/0241165 A1    Dec. 2, 2004

(30) Foreign Application Priority Data

Aug. 24, 2001  (JP) .............................. 2001-254826

(51) Int. Cl.
  *A61K 38/00* (2006.01)
  *A61K 38/04* (2006.01)
  *C07K 16/00* (2006.01)
  *C07K 17/00* (2006.01)
  *C07K 5/00* (2006.01)

(52) U.S. Cl. ...................... 530/326; 530/328; 530/329

(58) Field of Classification Search ................ 530/350, 530/324, 329, 328, 326; 435/68.1, 7.1
See application file for complete search history.

(56) References Cited

FOREIGN PATENT DOCUMENTS

| WO | WO 00/29441 | 5/2000 |
|----|-------------|--------|
| WO | WO 01/66134 | 9/2001 |
| WO | WO 02/46405 | 6/2002 |

OTHER PUBLICATIONS

Shintani et al. New neuropeptides containing carboxy-terminal RFamide and their receptor in mammals. Pharmaceutical Discovery Research Division, . Nat Cell Biol. 2000 Oct;2(10):703-8.*

Hinuma, et al. "New neuropeptides containing carboxy-terminal Rfamide and their receptor in mammals" Nature Cell Biology2: 703-708 (2000).

Liu, et al. "Identification and Characterization of Novel Mammalian Neuropeptide FF-like Peptides That Attenuate Morphine-induced Antinociiception" The Journal of Biological Chemistry 276(40): 36961-36969 (2001).

* cited by examiner

*Primary Examiner*—Robert A. Wax
*Assistant Examiner*—Robert Mondesi
(74) *Attorney, Agent, or Firm*—Mark Chao; Elaine M. Ramesh

(57) ABSTRACT

The RFRP-3 peptide of the present invention which is an agent for promoting prolactin secretion is useful as a prophylactic and/or therapeutic agent for various diseases associated with prolactin secretion, such as hypoovarianism, seminal vesicle hypoplasia, menopausal syndrome and hypothyroidism.

3 Claims, 21 Drawing Sheets

Fig. 1

```
              9              18             27             36             45              54
5' ATG GAA ATT ATT TCA TCA AAA CTA TTC ATT TTA TTG ACT TTA GCC ACT TCA AGC
   --- --- --- --- --- --- --- --- --- --- --- --- --- --- --- --- --- ---
   Met Glu Ile Ile Ser Ser Lys Leu Phe Ile Leu Leu Thr Leu Ala Thr Ser Ser 63             72             81             90             99             108
   TTG TTA ACA TCA AAC ATT TTT TGT GCA GAT GAA TTA GTG ATG TCC AAT CTT CAC
   --- --- --- --- --- --- --- --- --- --- --- --- --- --- --- --- --- ---
   Leu Leu Thr Ser Asn Ile Phe Cys Ala Asp Glu Leu Val Met Ser Asn Leu His 117            126            135            144            153            162
   AGC AAA GAA AAT TAT GAC AAA TAT TCT GAG CCT AGA GGA TAC CCA AAA GGG GAA
   --- --- --- --- --- --- --- --- --- --- --- --- --- --- --- --- --- ---
   Ser Lys Glu Asn Tyr Asp Lys Tyr Ser Glu Pro Arg Gly Tyr Pro Lys Gly Glu 171            180            189            198            207            216
   AGA AGC CTC AAT TTT GAG GAA TTA AAA GAT TGG GGA CCA AAA AAT GTT ATT AAG
   --- --- --- --- --- --- --- --- --- --- --- --- --- --- --- --- --- ---
   Arg Ser Leu Asn Phe Glu Glu Leu Lys Asp Trp Gly Pro Lys Asn Val Ile Lys 225            234            243            252            261            270
   ATG AGT ACA CCT GCA GTC AAT AAA ATG CCA CAC TCC TTC GCC AAC TTG CCA TTG
   --- --- --- --- --- --- --- --- --- --- --- --- --- --- --- --- --- ---
   Met Ser Thr Pro Ala Val Asn Lys Met Pro His Ser Phe Ala Asn Leu Pro Leu 279            288            297            306            315            324
   AGA TTT GGG AGG AAC GTT CAA GAA GAA AGA AGT GCT GGA GCA ACA GCC AAC CTG
   --- --- --- --- --- --- --- --- --- --- --- --- --- --- --- --- --- ---
   Arg Phe Gly Arg Asn Val Gln Glu Glu Arg Ser Ala Gly Ala Thr Ala Asn Leu 333            342            351            360            369            378
   CCT CTG AGA TCT GGA AGA AAT ATG GAG GTG AGC CTC GTG AGA CGT GTT CCT AAC
   --- --- --- --- --- --- --- --- --- --- --- --- --- --- --- --- --- ---
   Pro Leu Arg Ser Gly Arg Asn Met Glu Val Ser Leu Val Arg Arg Val Pro Asn 387            396            405            414            423            432
   CTG CCC CAA AGG TTT GGG AGA ACA ACA ACA GCC AAA AGT GTC TGC AGG ATG CTG
   --- --- --- --- --- --- --- --- --- --- --- --- --- --- --- --- --- ---
   Leu Pro Gln Arg Phe Gly Arg Thr Thr Thr Ala Lys Ser Val Cys Arg Met Leu 441            450            459            468            477            486
   AGT GAT TTG TGT CAA GGA TCC ATG CAT TCA CCA TGT GCC AAT GAC TTA TTT TAC
   --- --- --- --- --- --- --- --- --- --- --- --- --- --- --- --- --- ---
   Ser Asp Leu Cys Gln Gly Ser Met His Ser Pro Cys Ala Asn Asp Leu Phe Tyr 495            504            513            522            531            540
   TCC ATG ACC TGC CAG CAC CAA GAA ATC CAG AAT CCC GAT CAA AAA CAG TCA AGG
   --- --- --- --- --- --- --- --- --- --- --- --- --- --- --- --- --- ---
   Ser Met Thr Cys Gln His Gln Glu Ile Gln Asn Pro Asp Gln Lys Gln Ser Arg

TAA 3'
   ---
   ***
```

Fig. 3

```
               9          18         27         36         45         54
5' ATG GAA ATT ATT TCA TCA AAA CTA TTC ATT TTA TTG ACT TTA GCC ACT TCA AGC
   --- --- --- --- --- --- --- --- --- --- --- --- --- --- --- --- --- ---
   Met Glu Ile Ile Ser Ser Lys Leu Phe Ile Leu Leu Thr Leu Ala Thr Ser Ser 63          72         81         90         99        108
   TTG TTA ACA TCA AAC ATT TTT TGT GCA GAT GAA TTA GTG ATG TCC AAT CTT CAC
   --- --- --- --- --- --- --- --- --- --- --- --- --- --- --- --- --- ---
   Leu Leu Thr Ser Asn Ile Phe Cys Ala Asp Glu Leu Val Met Ser Asn Leu His 117         126        135        144        153        162
   AGC AAA GAA AAT TAT GAC AAA TAT TCT GAG CCT AGA GGA TAC CCA AAA GGG GAA
   --- --- --- --- --- --- --- --- --- --- --- --- --- --- --- --- --- ---
   Ser Lys Glu Asn Tyr Asp Lys Tyr Ser Glu Pro Arg Gly Tyr Pro Lys Gly Glu 171         180        189        198        207        216
   AGA AGC CTC AAT TTT GAG GAA TTA AAA GAT TGG GGA CCA AAA AAT GTT ATT AAG
   --- --- --- --- --- --- --- --- --- --- --- --- --- --- --- --- --- ---
   Arg Ser Leu Asn Phe Glu Glu Leu Lys Asp Trp Gly Pro Lys Asn Val Ile Lys 225         234        243        252        261        270
   ATG AGT ACA CCT GCA GTC AAT AAA ATG CCA CAC TCC TTC GCC AAC TTG CCA TTG
   --- --- --- --- --- --- --- --- --- --- --- --- --- --- --- --- --- ---
   Met Ser Thr Pro Ala Val Asn Lys Met Pro His Ser Phe Ala Asn Leu Pro Leu 279         288        297        306        315        324
   AGA TTT GGG AGG AAC GTT CAA GAA GAA AGA AGT GCT GGA GCA ACA GCC AAC CTG
   --- --- --- --- --- --- --- --- --- --- --- --- --- --- --- --- --- ---
   Arg Phe Gly Arg Asn Val Gln Glu Glu Arg Ser Ala Gly Ala Thr Ala Asn Leu 333         342        351        360        369        378
   CCT CTG AGA TCT GGA AGA AAT ATG GAG GTG AGC CTC GTG AGA CGT GTT CCT AAC
   --- --- --- --- --- --- --- --- --- --- --- --- --- --- --- --- --- ---
   Pro Leu Arg Ser Gly Arg Asn Met Glu Val Ser Leu Val Arg Arg Val Pro Asn 387         396        405        414        423        432
   CTG CCC CAA AGG TTT GGG AGA ACA ACA ACA GCC AAA AGT GTC TGC AGG ATG CTG
   --- --- --- --- --- --- --- --- --- --- --- --- --- --- --- --- --- ---
   Leu Pro Gln Arg Phe Gly Arg Thr Thr Thr Ala Lys Ser Val Cys Arg Met Leu 441         450        459        468        477        486
   AGT GAT TTG TGT CAA GGA TCC ATG CAT TCA CCA TGT GCC AAT GAC TTA TTT TAC
   --- --- --- --- --- --- --- --- --- --- --- --- --- --- --- --- --- ---
   Ser Asp Leu Cys Gln Gly Ser Met His Ser Pro Cys Ala Asn Asp Leu Phe Tyr 495         504        513        522        531        540
   TCC ATG ACC TGC CAG CAC CAA GAA ATC CAG AAT CCC GAT CAA AAA CAG TCA AGG
   --- --- --- --- --- --- --- --- --- --- --- --- --- --- --- --- --- ---
   Ser Met Thr Cys Gln His Gln Glu Ile Gln Asn Pro Asp Gln Lys Gln Ser Arg 549         558        567        576        585
   AGA CTG CTA TTC AAG AAA ATA GAT GAT GCA GAA TTG AAA CAA GAA AAA TAA 3'
   --- --- --- --- --- --- --- --- --- --- --- --- --- --- --- --- ---
   Arg Leu Leu Phe Lys Lys Ile Asp Asp Ala Glu Leu Lys Gln Glu Lys ***
```

Fig. 4

```
                9              18              27              36              45              54
5' ATG GAA ATT ATT TCA TTA AAA CGA TTC ATT TTA TTG ATG TTA GCC ACT TCA AGC
   --- --- --- --- --- --- --- --- --- --- --- --- --- --- --- --- --- ---
   Met Glu Ile Ile Ser Leu Lys Arg Phe Ile Leu Leu Met Leu Ala Thr Ser Ser 63              72              81              90              99             108
   TTG TTA ACA TCA AAC ATC TTC TGC ACA GAC GAA TCA AGG ATG CCC AAT CTT TAC
   --- --- --- --- --- --- --- --- --- --- --- --- --- --- --- --- --- ---
   Leu Leu Thr Ser Asn Ile Phe Cys Thr Asp Glu Ser Arg Met Pro Asn Leu Tyr 117             126             135             144             153             162
   AGC AAA AAG AAT TAT GAC AAA TAT TCC GAG CCT AGA GGA GAT CTA GGC TGG GAG
   --- --- --- --- --- --- --- --- --- --- --- --- --- --- --- --- --- ---
   Ser Lys Lys Asn Tyr Asp Lys Tyr Ser Glu Pro Arg Gly Asp Leu Gly Trp Glu 171             180             189             198             207             216
   AAA GAA AGA AGT CTT ACT TTT GAA GAA GTA AAA GAT TGG GCT CCA AAA ATT AAG
   --- --- --- --- --- --- --- --- --- --- --- --- --- --- --- --- --- ---
   Lys Glu Arg Ser Leu Thr Phe Glu Glu Val Lys Asp Trp Ala Pro Lys Ile Lys 225             234             243             252             261             270
   ATG AAT AAA CCT GTA GTC AAC AAA ATG CCA CCT TCT GCA GCC AAC CTG CCA CTG
   --- --- --- --- --- --- --- --- --- --- --- --- --- --- --- --- --- ---
   Met Asn Lys Pro Val Val Asn Lys Met Pro Pro Ser Ala Ala Asn Leu Pro Leu 279             288             297             306             315             324
   AGA TTT GGG AGG AAC ATG GAA GAA GAA AGG AGC ACT AGG GCG ATG GCC CAC CTG
   --- --- --- --- --- --- --- --- --- --- --- --- --- --- --- --- --- ---
   Arg Phe Gly Arg Asn Met Glu Glu Glu Arg Ser Thr Arg Ala Met Ala His Leu 333             342             351             360             369             378
   CCT CTG AGA CTC GGA AAA AAT AGA GAG GAC AGC CTC TCC AGA TGG GTC CCA AAT
   --- --- --- --- --- --- --- --- --- --- --- --- --- --- --- --- --- ---
   Pro Leu Arg Leu Gly Lys Asn Arg Glu Asp Ser Leu Ser Arg Trp Val Pro Asn 387             396             405             414             423             432
   CTG CCC CAG AGG TTT GGA AGA ACA ACA ACA GCC AAA AGC ATT ACC AAG ACC CTG
   --- --- --- --- --- --- --- --- --- --- --- --- --- --- --- --- --- ---
   Leu Pro Gln Arg Phe Gly Arg Thr Thr Thr Ala Lys Ser Ile Thr Lys Thr Leu 441             450             459             468             477             486
   AGT AAT TTG CTC CAG CAG TCC ATG CAT TCA CCA TCT ACC AAT GGG CTA CTC TAC
   --- --- --- --- --- --- --- --- --- --- --- --- --- --- --- --- --- ---
   Ser Asn Leu Leu Gln Gln Ser Met His Ser Pro Ser Thr Asn Gly Leu Leu Tyr 495             504             513             522             531             540
   TCC ATG GCC TGC CAG CCC CAA GAA ATC CAG AAT CCT GGT CAA AAG AAC CTA AGG
   --- --- --- --- --- --- --- --- --- --- --- --- --- --- --- --- --- ---
   Ser Met Ala Cys Gln Pro Gln Glu Ile Gln Asn Pro Gly Gln Lys Asn Leu Arg 549             558             567             576             585
   AGA CGG GGA TTC CAG AAA ATA GAT GAT GCA GAA TTG AAA CAA GAA AAA TAA 3'
   --- --- --- --- --- --- --- --- --- --- --- --- --- --- --- --- ---
   Arg Arg Gly Phe Gln Lys Ile Asp Asp Ala Glu Leu Lys Gln Glu Lys ***
```

Fig. 5

```
              9           18          27          36          45          54
5' ATG GAA ATT ATT TCA TCA AAG CGA TTC ATT TTA TTG ACT TTA GCA ACT TCA AGC
   --- --- --- --- --- --- --- --- --- --- --- --- --- --- --- --- --- ---
   Met Glu Ile Ile Ser Ser Lys Arg Phe Ile Leu Leu Thr Leu Ala Thr Ser Ser 63          72          81          90          99         108
   TTC TTA ACT TCA AAC ACC CTT TGT TCA GAT GAA TTA ATG ATG CCC CAT TTT CAC
   --- --- --- --- --- --- --- --- --- --- --- --- --- --- --- --- --- ---
   Phe Leu Thr Ser Asn Thr Leu Cys Ser Asp Glu Leu Met Met Pro His Phe His 117         126         135         144         153         162
   AGC AAA GAA GGT TAT GGA AAA TAT TAC CAG CTG AGA GGA ATC CCA AAA GGG GTA
   --- --- --- --- --- --- --- --- --- --- --- --- --- --- --- --- --- ---
   Ser Lys Glu Gly Tyr Gly Lys Tyr Tyr Gln Leu Arg Gly Ile Pro Lys Gly Val 171         180         189         198         207         216
   AAG GAA AGA AGT GTC ACT TTT CAA GAA CTC AAA GAT TGG GGG GCA AAG AAA GAT
   --- --- --- --- --- --- --- --- --- --- --- --- --- --- --- --- --- ---
   Lys Glu Arg Ser Val Thr Phe Gln Glu Leu Lys Asp Trp Gly Ala Lys Lys Asp 225         234         243         252         261         270
   ATT AAG ATG AGT CCA GCC CCT GCC AAC AAA GTG CCC CAC TCA GCA GCC AAC CTT
   --- --- --- --- --- --- --- --- --- --- --- --- --- --- --- --- --- ---
   Ile Lys Met Ser Pro Ala Pro Ala Asn Lys Val Pro His Ser Ala Ala Asn Leu 279         288         297         306         315         324
   CCC CTG AGG TTT GGG AGG AAC ATA GAA GAC AGA AGA AGC CCC AGG GCA CGG GCC
   --- --- --- --- --- --- --- --- --- --- --- --- --- --- --- --- --- ---
   Pro Leu Arg Phe Gly Arg Asn Ile Glu Asp Arg Arg Ser Pro Arg Ala Arg Ala 333         342         351         360         369         378
   AAC ATG GAG GCA GGG ACC ATG AGC CAT TTT CCC AGC CTG CCC CAA AGG TTT GGG
   --- --- --- --- --- --- --- --- --- --- --- --- --- --- --- --- --- ---
   Asn Met Glu Ala Gly Thr Met Ser His Phe Pro Ser Leu Pro Gln Arg Phe Gly 387         396         405         414         423         432
   AGA ACA ACA GCC AGA CGC ATC ACC AAG ACA CTG GCT GGT TTG CCC CAG AAA TCC
   --- --- --- --- --- --- --- --- --- --- --- --- --- --- --- --- --- ---
   Arg Thr Thr Ala Arg Arg Ile Thr Lys Thr Leu Ala Gly Leu Pro Gln Lys Ser 441         450         459         468         477         486
   CTG CAC TCC CTG GCC TCC AGT GAA TCG CTC TAT GCC ATG ACC CGC CAG CAT CAA
   --- --- --- --- --- --- --- --- --- --- --- --- --- --- --- --- --- ---
   Leu His Ser Leu Ala Ser Ser Glu Ser Leu Tyr Ala Met Thr Arg Gln His Gln 495         504         513         522         531         540
   GAA ATT CAG AGT CCT GGT CAA GAG CAA CCT AGG AAA CGG GTG TTC ACG GAA ACA
   --- --- --- --- --- --- --- --- --- --- --- --- --- --- --- --- --- ---
   Glu Ile Gln Ser Pro Gly Gln Glu Gln Pro Arg Lys Arg Val Phe Thr Glu Thr 549         558         567         576         585         594
   GAT GAT GCA GAA AGG AAA CAA GAA AAA ATA GGA AAC CTC CAG CCA GTC CTT CAA
   --- --- --- --- --- --- --- --- --- --- --- --- --- --- --- --- --- ---
   Asp Asp Ala Glu Arg Lys Gln Glu Lys Ile Gly Asn Leu Gln Pro Val Leu Gln 603         612
   GGG GCT ATG AAG CTG TGA 3'
   --- --- --- --- --- ---
   Gly Ala Met Lys Leu ***
```

Fig. 6

```
                        10          20          30          40          50
hLPLRF.aa      1  MEIISSKLFI LLTLATSSLL TSNIFCADEI VMSNLHSKEN YDKYSEPRG-    50
bLPLRF.aa      1  MEIISKRFI  LIMLATSSLL TSNIFCIDES RMPNLVSKKN YDKYSEPRGD    50
rLPLRF.aa      1  MEIISSKRFI LLTLATSSFL TSNTLCQDEI MPHFHSKEG  MGKYVQLRGI    50

60          70          80          90         100
hLPLRF.aa     51  --YPKG---- ER SILNFEELKDW GPKNVIKMST PAVNKMPHSF ANLPLRFGRN   100
bLPLRF.aa     51  LGWEK----  ER SLITFEEVMDM APKI-IKMNK EVVNKMPFSA ANLPLRFGRN   100
rLPLRF.aa     51  PKGVKER    SVTFELKDW GAKKLIKMSP APANKVPHSA ANLPLRFGRN   100

110         120         130         140         150
hLPLRF.aa    101  VQEERSAGAT ANLPLRSGRN MEVSIVRRVP NLPQRFGRTT TAKSVCRMLS   150
bLPLRF.aa    101  MEEERSIRAM ANLPLRFGRN RPSLSRWP   NLPQRFGRTT TAKSITKTLS   150
rLPLRF.aa    101  IEDRRSFRAR ANM------  EAGIMSHFE  SLPQRFGRTT -AFRLTKTLA   150

160         170         180         190         200
hLPLRF.aa    151  DLSMHSE    CANDLYSMT COHQEIQNPD PKQSRLLFK  KIDDAELKQE   200
bLPLRF.aa    151  NLOSMHSF   STN-LIYSMA CQEEIQNPG  QKNLRRG-FQ KIDDAELKQE   200
rLPLRF.aa    151  GLPQKSTHSL ASSESLYAMI RQHQEIQSPG QEDPKKVMT  ETDDAERKQE   200

210         220         230         240         250
hLPLRF.aa    201  K*-------- ---------- ---------- ---------- ----------   250
bLPLRF.aa    201  K*-------- ---------- ---------- ---------- ----------   250
rLPLRF.aa    201  KIGNLQPVLQ GAMKL*.... .......... .......... ..........   250
```

Fig. 7

```
  1  TTTAGACTTAGACGAAATGGAAATTATTTCATTAAAACGATTCATTTTATTGACTGTG         58
  1                             MetGluIleIleSerLeuLysArgPheIleLeuLeuThrVal  14

59  GCAACTTCAAGCTTCTTAACATCAAACACCTTCTGTACAGATGAGTTCATGATGCCTCAT    118
 15  AlaThrSerSerPheLeuThrSerAsnThrPheCysThrAspGluPheMetMetProHis    34

119  TTTCACAGCAAAGAAGGTGACGGAAAAATACTCCCAGCTGAGAGGAATCCCAAAAGGGGAA   178
 35  PheHisSerLysGluGlyAspGlyLysTyrSerGlnLeuArgGlyIleProLysGlyGlu    54

179  AAGGAAAGAAGTGTCAGTTTTCAAGAACTAAAAGATTGGGGGGCAAAGAATGTTATTAAG    238
 55  LysGluArgSerValSerPheGlnGluLeuLysAspTrpGlyAlaLysAsnValIleLys    74

239  ATGAGTCCAGCCCCTGCCAACAAAGTGCCCCACTCAGCAGCCAACCTGCCCCTGAGATTT    298
 75  MetSerProAlaProAlaAsnLysValProHisSerAlaAlaAsnLeuProLeuArgPhe    94

299  GGAAGGACCATAGATGAGAAAAGAAGCCCCGCAGCACGGGTCAACATGGAGGCAGGGACC   358
 95  GlyArgThrIleAspGluLysArgSerProAlaAlaArgValAsnMetGluAlaGlyThr   114

359  AGGAGCCATTTCCCCAGCCTGCCCCAAAGGTTTGGGAGAACAACAGCCAGAAGCCCCAAG   418
115  ArgSerHisPheProSerLeuProGlnArgPheGlyArgThrThrAlaArgSerProLys   134

419  ACACCCGCTGATTTGCCACAGAAACCCCTGCACTCACTGGGCTCCAGCGAGTTGCTCTAC   478
135  ThrProAlaAspLeuProGlnLysProLeuHisSerLeuGlySerSerGluLeuLeuTyr   154

479  GTCATGATCTGCCAGCACCAAGAAATTCAGAGTCCTGGTGGAAAGCGAACGAGGAGAGGA   538
155  ValMetIleCysGlnHisGlnGluIleGlnSerProGlyGlyLysArgThrArgArgGly   174

539  GCGTTTGTGGAAACAGATGATGCAGAAAGGAAACCAGAAAAATAGGAAACCTCGAGCCCG   598
175  AlaPheValGluThrAspAspAlaGluArgLysProGluLys***                  188

599  ACTTCAAGAGGCTACGGAGC                                           618
188                                                                 188
```

RFRP-3 AND DNA THEREOF

This application is the National Phase filing of International Patent Application No. PCT/JP02/08466, filed Aug. 22, 2002.

TECHNICAL FIELD

The present invention relates to a novel polypeptide having effect in regulating prolactin secretion (hereinafter, sometimes abbreviated to "RFRP-3"), a polynucleotide encoding the polypeptide, a method of producing RFRP-3, use of RFRP-3 or a DNA thereof, and so on.

BACKGROUND ART

A large number of hormones and neurotransmitters are regulating the functions of the living body through specific receptors present in the cell membrane. Many of these receptors perform intracellular signal transduction through the activation of guanine nucleotide-binding proteins (hereinafter, sometimes abbreviated to "G proteins") to which they are coupled. Since these receptors have a common structure with seven transmembrane domains, they are called G protein-coupled receptors or seven times transmembrane type receptors (7TMRs).

The hypothalamus-pituitary system is one of those passways which the above-mentioned hormones/neurotransritters and G protein-coupled receptors regulate the functions of the living body. The secretion of pituitary hormones from the pituitary is regulated by hypothalamic hormones, and the functions of target cells/organs are regulated through pituitary hormones released into the blood. The regulation of functions important for the living body, such as the maintenance of homeostasis, development of the reproductive system or individuals, regulation of metabolism or growth, and so forth is performed through this passway.

The secretion of pituitary hormones is regulated by positive or negative feedback mechanisms involving hypothalamic hormones and peripheral hormones secreted from target internal secretion glands.

It is known that these hormones, factors and their receptors are not localized in the hypothalamus-pituitary system but, in general, distributed widely in the brain. Therefore, it is considered that substances called hypothalamic hormones are functioning as neurotransmitters or neuromodulators in the central nervous system.

These hormones, factors and their receptors are distributed similarly in peripheral tissues, and are considered to have important functions individually.

Under circumstances, development of medicines that regulate the secretion of pituitary hormones from the pituitary through regulation of functions of the living body by a G protein-coupled receptor and its ligand, particularly through regulation of hypothalamic hormone secretion, has been desired.

A peptide that regulates prolactin release is disclosed in Nature Cell Biology, Vol. 2, October 2000, pp. 703–708.

Secretory peptides designated RFRP-1, RFRP-2 and RFRP-3, and a G protein-coupled receptor protein OT7T022 to which these peptides bind are disclosed in WO 00/29441.

It is disclosed in WO 01/66134 that those secretory peptides have an effect in regulating prolactin secretion.

It is an object of the present invention to provide a novel polypeptide which has an excellent effect in regulating release.

DISCLOSURE OF THE INVENTION

As a result of intensive and extensive researches toward the solution of the above problem, the present inventors have succeeded in isolating and purifying bovine RFRP-3 which is characterized by having an RF amide-like structure. The present invention has been achieved upon further researches based thereon.

The present invention provides:

[1] (1) A peptide consisting of an amino acid sequence which is from position 104 (Ala) to position 131 (Phe) of SEQ ID NO: 1 or an amide or ester thereof, or a salt thereof;
(2) a peptide consisting of an amino acid sequence which is from position 101 (Ser) to position 131 (Phe) of SEQ ID NO: 1 or an amide or ester thereof, or a salt thereof; or (3) a peptide consisting of an amino acid sequence which is from position 104 (Ala) to position 131 (Phe) of SEQ ID NO: 14 or an amide or ester thereof, or a salt thereof;

[2] (1) A peptide consisting of an amino acid sequence which is from position 125 (Pro) to position 131 (Phe) of SEQ ID NO: 1 or an amide or ester thereof, or a salt thereof;
(2) a peptide consisting of an amino acid sequence which is from position 126 (Asn) to position 131 (Phe) of SEQ ID NO: 1 or an amide or ester thereof, or a salt thereof; or (3) a peptide consisting of an amino acid sequence which is from position 127 (Leu) to position 131 (Phe) of SEQ ID NO: 1 or an amide or ester thereof, or a salt thereof;

[3] An amide of the peptide of [1] or [2] above, or a salt of the amide;

[4] The peptide of [1] or [2] above wherein the C-terminal carboxyl group is amidated, or a salt thereof;

[5] A polynucleotide comprising a polynucleotide encoding the peptide of [1] above;

[6] A polynucleotide comprising a polynucleotide encoding the peptide of [2] above;

[7] The polynucleotide of [5] or [6] above, which is a DNA;

[8] The polynucleotide of [5] above, which consists of (1) a nucleotide sequence which is from position 310 to position 393 of SEQ ID NO: 2, (2) a nucleotide sequence which is from position 301 to position 393 of SEQ ID NO: 2, or (3) a nucleotide sequence which is from position 310 to position 393 of SEQ ID NO: 15;

[9] The polynucleotide of [6] above, which consists of (1) a nucleotide sequence which is from position 373 to position 393 of SEQ ID NO: 2, (2) a nucleotide sequence which is from position 376 to position 393 of SEQ ID NO: 2, or (3) a nucleotide sequence which is from position 379 to position 393 of SEQ ID NO: 2;

[10] A recombinant vector comprising the polynucleotide of [5] or [6] above;

[11] A transformant transformed with the recombinant vector of [10] above;

[12] A method for producing the peptide of [1] or [2] above or an amide or ester thereof, or a salt thereof, comprising culturing the transformant of [11] above and allowing the polypeptide of [1] or [2] above to be produced.

[13] A medicine comprising the peptide of [1] or [2] above or an amide or ester thereof, or a salt thereof.

[14] A medicine comprising the polynucleotide of [5] or [6] above;

[15] The medicine of [13] or [14] above, which is an agent for prolactin secretion;

[16] The medicine of [13] or [14] above, which is an agent for promoting prolactin secretion;

[17] The medicine of [13] or [14] above, which is an inhibitor for prolactin secretion;

[18] The medicine of [16] above, which is a prophylactic and/or therapeutic agent for hypoovarianism, seminal vesicle hypoplasia, osteoporosis, menopausal syndrome, hypogalactia, hypothyroidism or renal insufficiency;

[19] The medicine of [17] above, which is a prophylactic and/or therapeutic agent for hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma, Sheehan's syndrome or spermatogenic disorder;

[20] The medicine of [13] or [14] above, which is a promoting agent for milk secretion in a mammal.

[21] The medicine of [13] or [14] above, which is an agent for testing the function of prolactin secretion;

[22] An antibody to the peptide of [1] or [2] above or an amide or ester thereof, or a salt thereof;

[23] A medicine comprising the antibody of [22] above;

[24] The medicine of [23] above, which is a prophylactic and/or therapeutic agent for hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma or Sheehan's syndrome or spermatogenic disorder;

[25] A diagnostic agent comprising the antibody of [22] above;

[26] The diagnostic agent of [25] above, which is a diagnostic agent for hypoovarianism, seminal vesicle hypoplasia, osteoporosis, menopausal syndrome, hypogalactia, hypothyroidism or renal insufficiency, hyperprolactinemia, pituitary adenoma, diencephalic tumor, menstrual disorder, stresses, autoimmune diseases, prolactinoma, sterility, impotence, amenorrhea, galactorthea, acromegaly, Chiari-Frommel syndrome, Argonz-del Castillo syndrome, Forbes-Albright syndrome, breast cancer lymphoma or Sheehan's syndrome or spermatogenic disorder.

[27] A diagnostic agent comprising the polynucleotide of [5] or [6] above;

[28] The diagnostic agent of [27] above, which is a diagnostic agent for hypoovarianism, seminal vesicle hypoplasia, osteoporosis, menopausal syndrome, hypogalactia, hypothyroidism or renal insufficiency, hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma or Sheehan's syndrome or spermatogenic disorder

[29] An antisense DNA which comprises a nucleotide sequence, or a part thereof, complementary or substantially complementary to a DNA encoding the peptide of [1] or [2] above, and has an effect capable of inhibiting the expression of the DNA;

[30] A medicine comprising the antisense DNA of [29] above;

[31] The medicine of [30] above, which is a prophylactic and/or therapeutic agent for hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma or Sheehan's syndrome or spermatogenic disorder;

[32] A method of screening for a compound or a salt thereof that promotes or inhibits the activity of the peptide of [1] or [2] above or an amide or ester thereof, or a salt thereof, comprising using the peptide of [1] or [2] above or an anode or ester thereof, or a salt thereof;

[33] The screening method of [32] above, further comprising using a protein comprising an amino acid sequence identical or substantially identical to the amino acid sequence represented by SEQ ID NO: 37 or a salt of the protein, or a partial peptide of the protein, or an amide or ester of the partial peptide, or a salt of the partial peptide.

[34] The screening method of [32] above, further comprising using a protein consisting of the amino acid sequence represented by SEQ ID NO: 37 or SEQ ID NO: 54 or a salt of the protein, or a partial peptide of the protein, or an amide or ester of the partial peptide, or a salt of the partial peptide;

[35] A kit for screening for a compound or a salt thereof that promotes or inhibits the activity of the peptide of [1] or [2] above or an amide or ester thereof, or a salt thereof, comprising the peptide of [1] or [2] above or an amide or ester thereof, or a salt thereof;

[36] A compound or a salt thereof that promotes or inhibits the activity of the peptide of [1] or [2] above or an amide or ester thereof, or a salt thereof, wherein the compound or salt thereof is obtainable by the screening method of [32] above or the screening kit of [35] above;

[37] A medicine comprising a compound or a salt thereof that promotes or inhibits the activity of the peptide of [1] or [2] above or an amide or ester thereof, or a salt thereof;

[38] An agent for promoting prolactin secretion comprising a compound or a salt thereof that promotes the activity of the peptide of [1] or [2] above or an amide or ester thereof, or a salt thereof;

[39] A prophylactic and/or therapeutic agent for hypoovarianism, seminal vesicle hypoplasia, osteoporosis, menopausal syndrome, hypogalactia, hypothyroidism or renal insufficiency, comprising a compound or a salt thereof that promotes the activity of the peptide of [1] or [2] above or an amide or ester thereof, or a salt thereof;

[40] A promoting agent for milk secretion in a mammal, comprising a compound or a salt thereof that promotes the activity of the peptide of [1] or [2] above or an amide or ester thereof, or a salt thereof;

[41] An inhibitor for prolactin secretion comprising a compound or a salt thereof that inhibits the activity of the peptide of [1] or [2] above or an amide or ester thereof, or a salt thereof;

[42] A prophylactic and/or therapeutic agent for hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma, Sheehan's syndrome or spermatogenic disorder.

[43] A method of promoting prolactin secretion, comprising administering to a mammal an effective amount of (i) the peptide of [1] or [2] above or an amide or ester thereof, or a salt thereof, (ii) the polynucleotide of [5] or [6] above, or (iii) a compound or a salt thereof that promotes the activity of the peptide of [1] or [2] above or an amide or ester thereof, or a salt thereof;

[44] A method of preventing and/or treating hypoovarianism, seminal vesicle hypoplasia, osteoporosis, menopausal syndrome, hypogalactia, hypothyroidism or renal insufficiency, comprising administering to a mammal an effective amount of (i) the peptide of [1] or [2] above or an amide or ester thereof, or a salt thereof, (ii) the polynucleotide of [5] or [6] above, or (iii) a compound or a salt thereof that promotes the activity of the peptide of [1] or [2] above or an amide or ester thereof, or a salt thereof;

[45] A method of inhibiting prolactin secretion, comprising administering to a mammal an effective amount of (i) the antibody of [22] above, (ii) the antisense DNA of [29] above, or (iii) a compound or a salt thereof that inhibits the activity of the peptide of [1] or [2] above or an amide or ester thereof, or a salt thereof;

[46] A method of preventing and/or treating hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma, Sheehan's syndrome or spermatogenic disorder, comprising administering to a mammal an effective amount of (i) the antibody of [22] above, (ii) the antisense DNA of [29] above, or (iii) a compound or a salt thereof that inhibits the activity of the peptide of [1] or [2] above or an amide or ester thereof, or a salt thereof;

[47] Use of (i) the peptide of [1] or [2] above or an amide or ester thereof, or a salt thereof, (ii) the polynucleotide of [5] or [6] above, or (iii) a compound or a salt thereof that promotes the activity of the peptide of [1] or [2] above or an amide or ester thereof, or a salt thereof, for manufacturing a prolactin secretion-promoting agent;

[48] Use of (i) the peptide of [1] or [2] above or an amide or ester thereof, or a salt thereof, (ii) the polynucleotide of [5] or [6] above, or (iii) a compound or a salt thereof that promotes the activity of the peptide of [1] or [2] above or an amide or ester thereof, or a salt thereof, for manufacturing a prophylactic and/or therapeutic agent for hypoovarianism, seminal vesicle hypoplasia, osteoporosis, menopausal syndrome, hypogalactia, hypothyroidism or renal insufficiency;

[49] Use of (i) the antibody of [22] above, (ii) the antisense DNA of [29] above, or (iii) a compound or a salt thereof that inhibits the activity of the peptide of [1] or [2] above or an amide or ester thereof, or a salt thereof, for manufacturing an inhibitor of prolactin secretion; and

[50] Use of (i) the antibody of [22] above, (ii) the antisense DNA of [29] above, or (iii) a compound or a salt thereof that inhibits the activity of the peptide of [1] or [2] above or an amide or ester thereof, or a salt thereof, for manufacturing a prophylactic and/or therapeutic agent for hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma, Sheehan's syndrome or spermatogenic disorder.

BRIEF DESCRIPTION OF THE DRAWINGS

FIG. 1 shows the nucleotide sequence of a DNA encoding the polypeptide of the present invention (human type) obtained in Reference Example 2, and the amino acid sequence deduced from the nucleotide sequence.

FIG. 3 shows the nucleotide sequence of a DNA encoding the polypeptide of the present invention (human type) obtained in Reference Example 3, and the amino acid sequence deduced from the nucleotide sequence.

FIG. 4 shows the nucleotide sequence of a DNA encoding the polypeptide of the present invention (bovine type) obtained in Reference Example 4, and the amino acid sequence deduced from the nucleotide sequence.

FIG. 5 shows the nucleotide sequence of a DNA encoding the polypeptide of the present invention (rat type) obtained in Reference Example 5, and the amino acid sequence deduced from the nucleotide sequence.

FIG. 6 shows comparison of the amino acid sequences of the polypeptides of the present invention obtained in Reference Examples 3, 4 and 5.

FIG. 7 shows the amino acid sequence of the polypeptide of the present invention (mouse type) obtained in Reference Example 6 and the nucleotide sequence of a DNA encoding the polypeptide.

The time point of the administration is taken as 0 min. Mark * represents significance level: $p<0.05$ and mark ** represents significance level: $p<0.01$.

Figure 11:
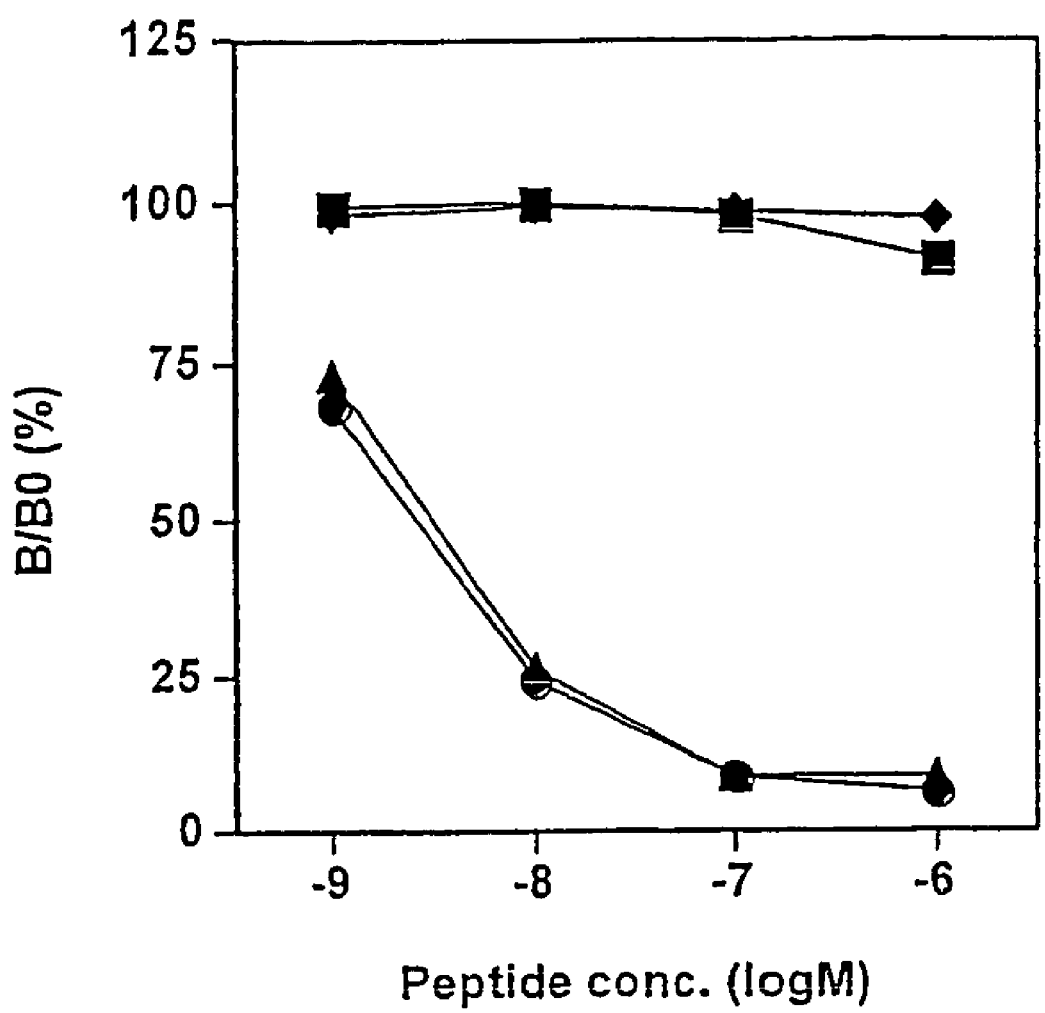

FIG. 11 shows the result of the reactivity of RF amide-related peptides examined by competitive ELA using anti-rat RFRP-1 monoclonal antibody 1F3 in Reference Example 13.

To anti-mouse IgGAM antibody-coated 96-well plates, 50 μl of anti-rat RFRP-1 monoclonal antibody 1F3 and 50 μl of each peptide at concentrations indicated in the axis of abscissas were added. After 16-hr incubation at 4° C., HRP-rat RFRP-1 was added and incubated for another 2 hr at room temperature. After washing the plates, HRP activity was determined at an absorbance of 450 nm. "B" shows the absorbance when the peptide was added; "$B_0$" shows the absorbance when the peptide was not added.

In this Figure, -●- represents a peptide consisting of an amino acid sequence which is from position 83 (Val) to position 94 (Phe) of SEQ ID NO: 50 wherein the C-terminal carboxyl group is amidated (VPHSAANLPLRF-NH$_2$); -▲- represents a peptide consisting of an amino acid sequence which is from position 90 (Leu) to position 94 (Phe) of SEQ ID NO: 50 wherein the C-terminal carboxyl group is amidated (LPLRF-NH$_2$); -■- represents a peptide consisting of an amino acid sequence which is from position 124 (Val) to position 131 (Phe) of SEQ ID NO: 1 wherein the C-terminal carboxyl group is amidated (VPNLPQRF-NH$_2$); and -□- represents a peptide consisting of an amino acid sequence which is from position 128 (Pro) to position 131 (Phe) of SEQ ID NO: 1 wherein the C-terminal carboxyl group is amidated (PQRF-NH$_2$).

Figure 12:
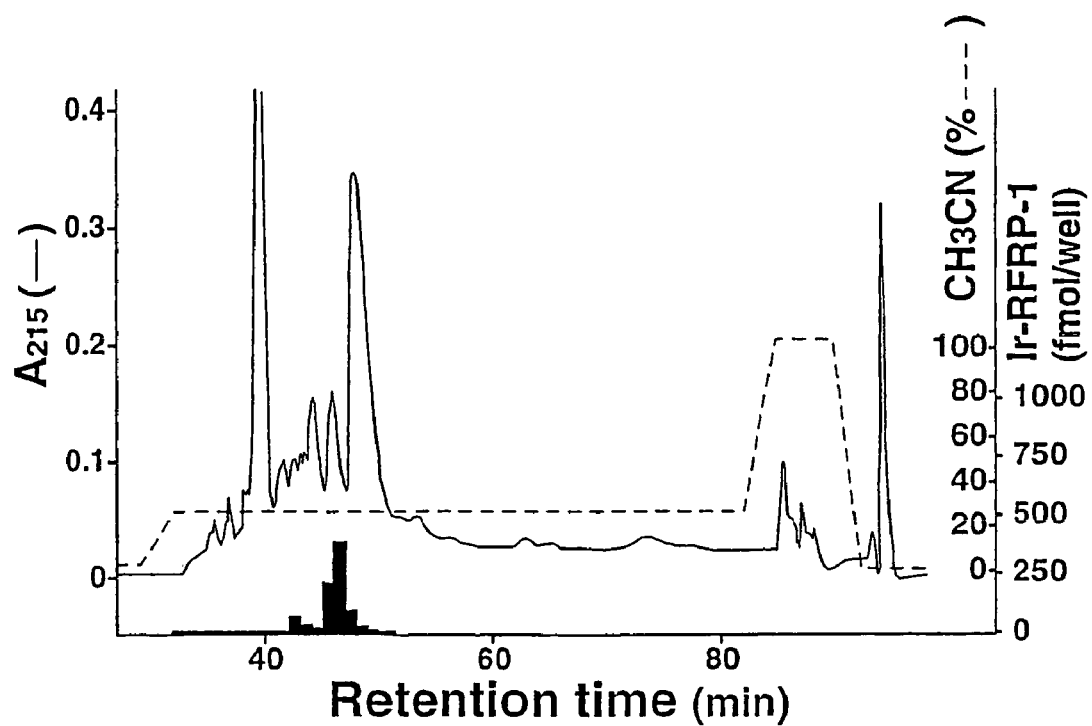

FIG. 12 shows the chromatographic pattern of finally purified endogenous RFRP-1 from bovine hypothalamus obtained in Example A2. It is shown that the chromatogram of μ RPC C2/C18 SC 2.1/10 at the final purification stage. The axis of ordinates represents absorbance and the concentration of eluted acetonitrile; the axis of abscissas represents retention time. The black columns in the Figure show the RFRP-1-like immune activities of individual fractions measured by competitive EIA using anti-rat RFRP-1 monoclonal antibody 1F3.

Figure 13:
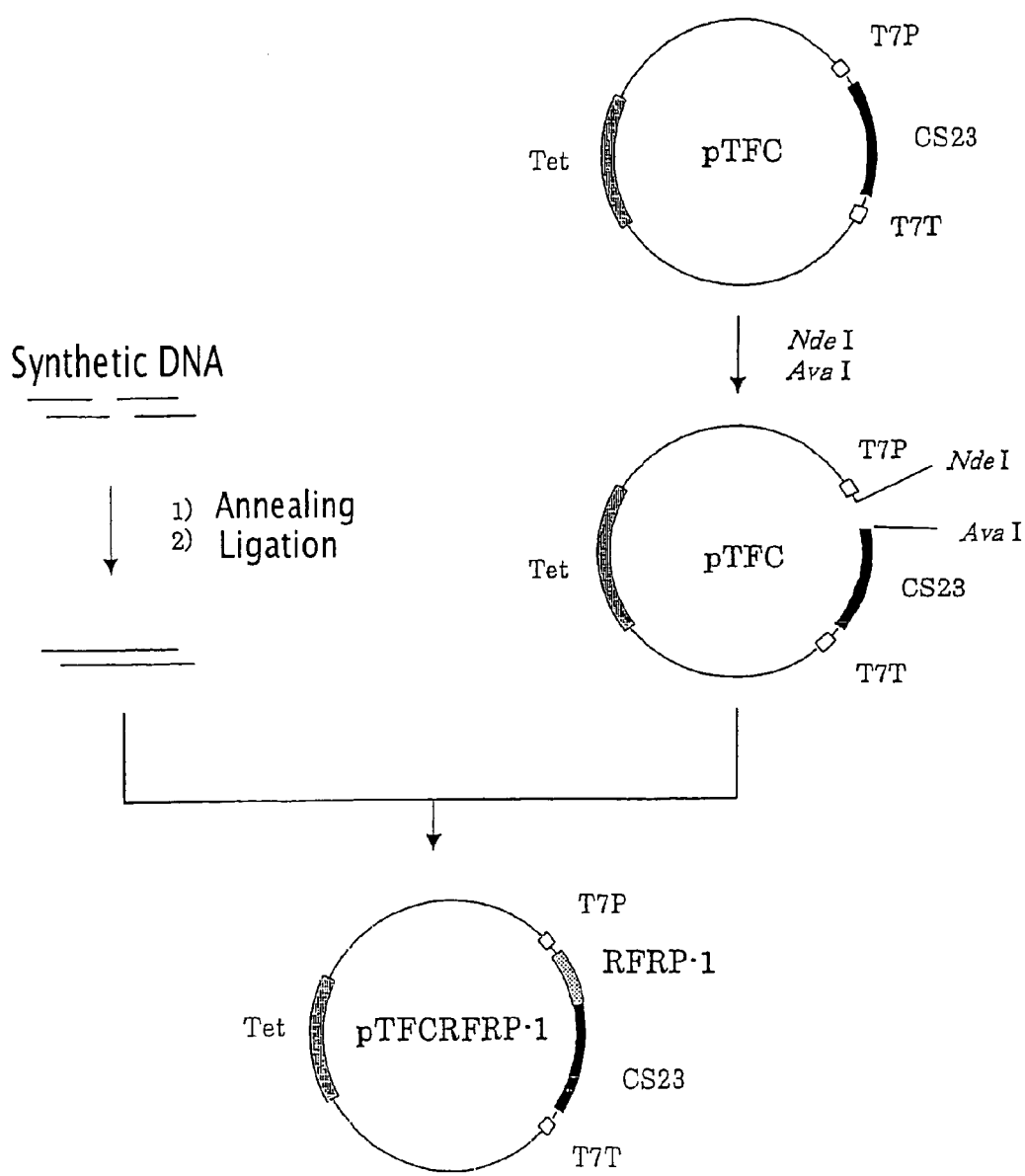

FIG. 13 shows the construction of plasmid pTFCRFRP-1 obtained in Example A4.

Figure 14:
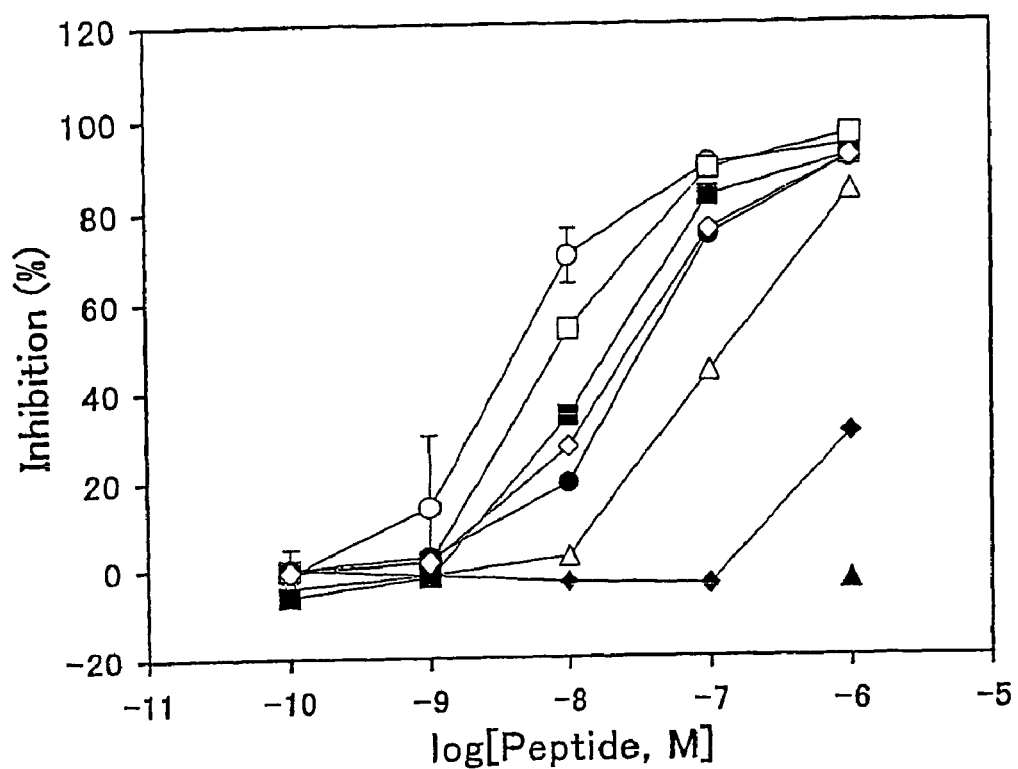

FIG. 14 shows the figure of the inhibitory activities of individual peptides against the increase of intracellular cAMP with forskolin treatment examined in Example A8. In this Figure, -○- represents hRFRP-1–12 (a peptide comprising an amino acid sequence which is from position 81 (Met) to position 92 (Phe) of SEQ ID NO: 1); -■- represents hRFRP-1–37 (a peptide comprising an amino acid sequence which is from position 56 (Ser) to position 92 (Phe) of SEQ ID NO: 1); -◇- represents rRFRP-1–37 (a peptide comprising an amino acid sequence which is from position 58 (Ser) to position 94 (Phe) of SEQ ID NO: 50); -▲- represents hRFRP-2–12 (a peptide comprising an amino acid sequence which is from position 101 (Phe) to position 112 (Ser) of SEQ ID NO: 1); -□- represents hRFRP-3–8 (a peptide comprising an amino acid sequence which is from position 124 (Val) to position 131 (Phe) of SEQ ID NO: 1); -◆- represents PQRFamide (a peptide represented by Pro-Gln-Arg-Phe-NH$_2$); -●- represents LPLRFamide (a peptide represented by Leu-Pro-Leu-Arg-Phe-NH$_2$); and -▲- represents NPFF (a peptide represented by Asn-Pro-Phe-Phe).

Figure 15:
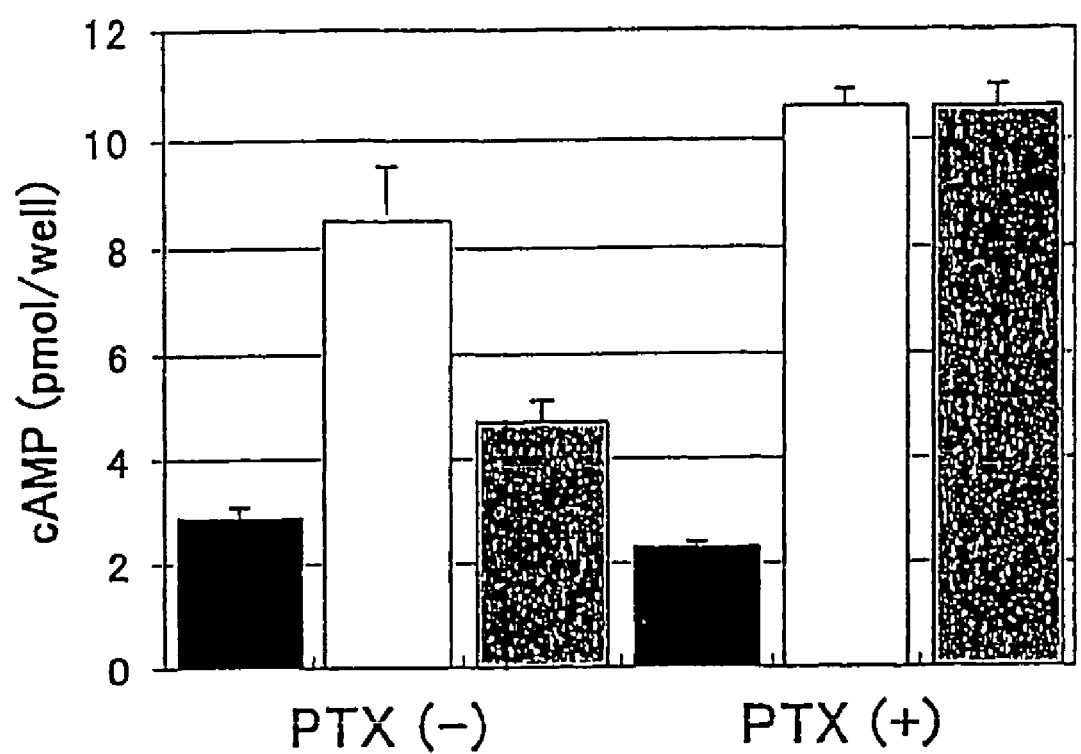

FIG. 15 shows the figure of the effect of pertussis toxin upon activation of human OT7T022 receptor by RFRP peptides examined in Example A9; the above effect is shown using cAMP production inhibitory effect as an indicator.

Figure 16:
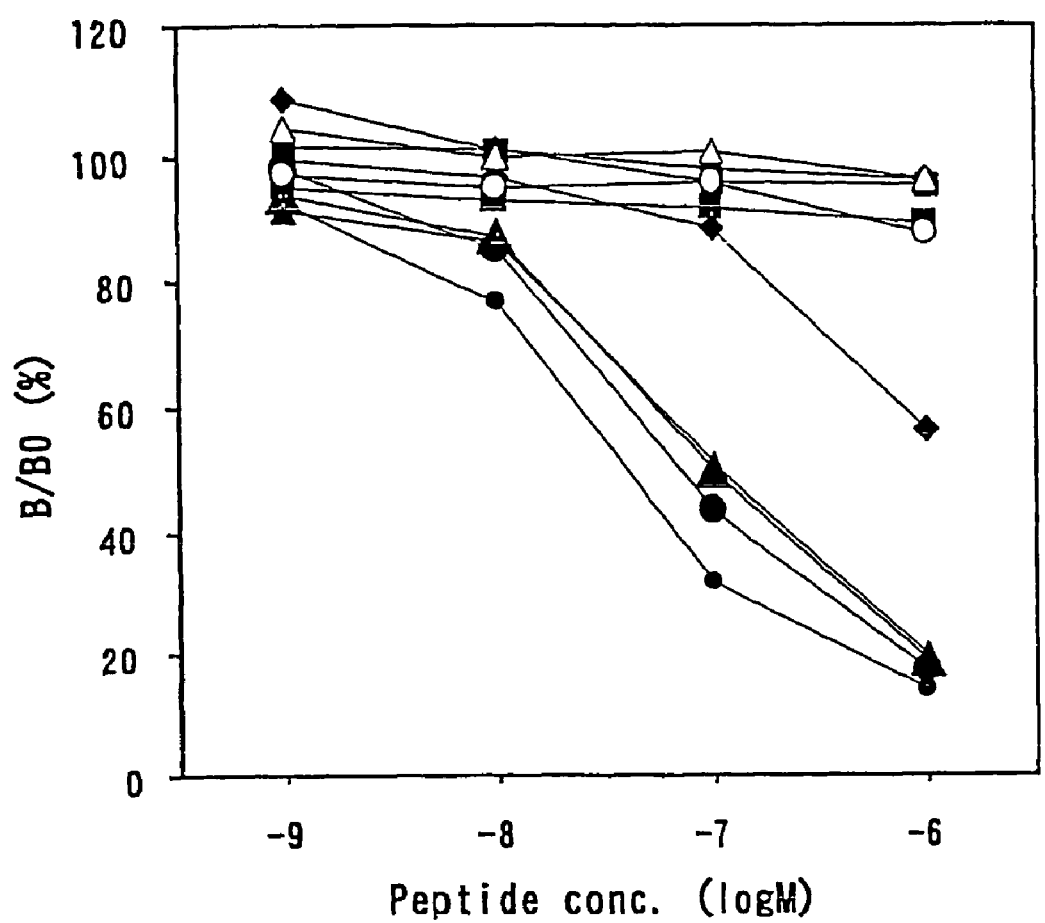

FIG. 16 shows the reactivity of RF amide-related peptides in competitive EIA using anti-rat RFRP-3 monoclonal antibody 7F6. "B" shows the absorbance when the peptide was added; "B$_0$" shows the absorbance when the peptide was not added.

Figure 17:
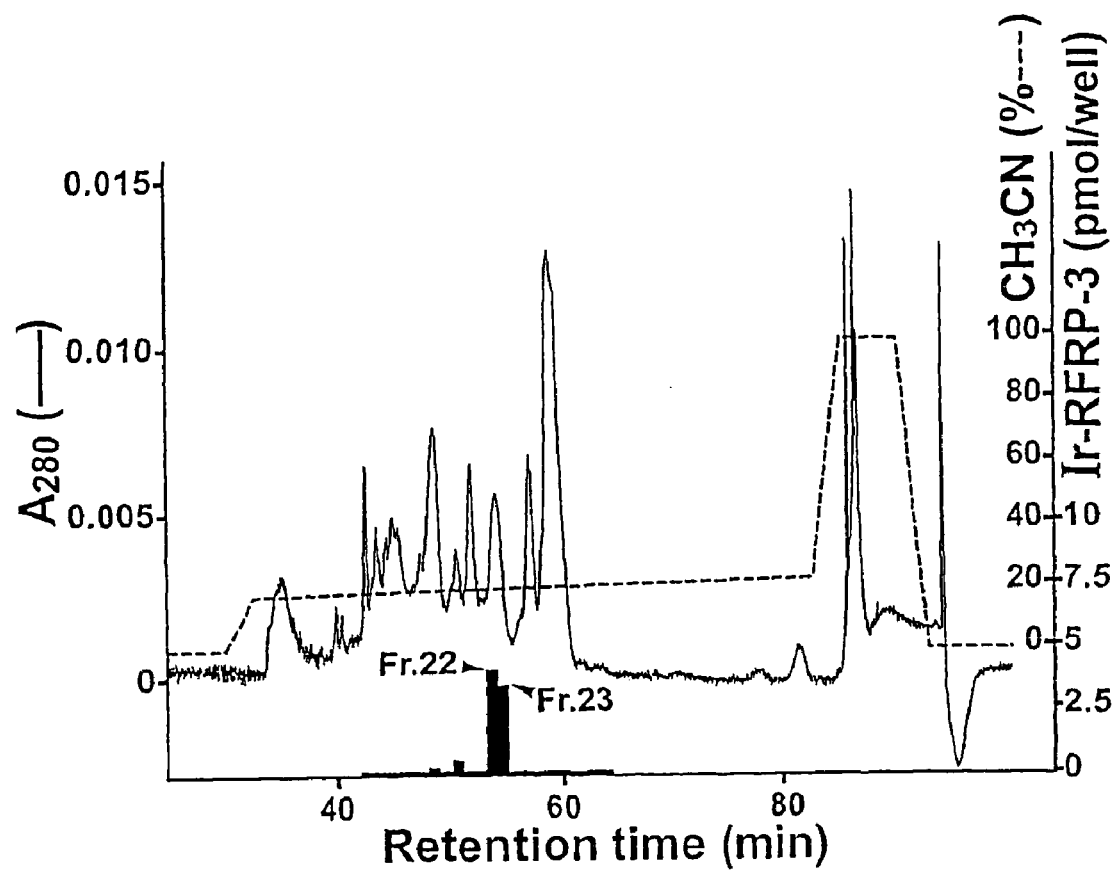

FIG. 17 shows the chromatographic pattern of finally purified endogenous RFRP-3 from bovine hypothalamus. This chromatographic chart shows the absorbance at 215 nm and the concentration of eluted acetonitrile. The black columns in the Figure show the RFRP-3-like immune activities of individual fractions measured by competitive EIA using anti-rat RFRP-3 monoclonal antibody 7F6.

Figure 18:
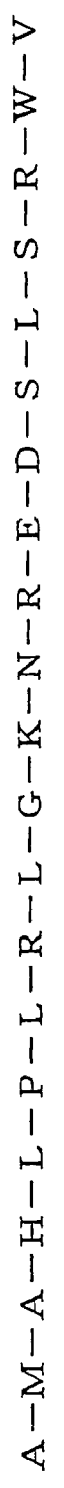

FIG. 18 shows the results of N-terminal amino acid analysis for the finally purified endogenous RFRP-3 sample from bovine hypothalamus.

Figure 19:
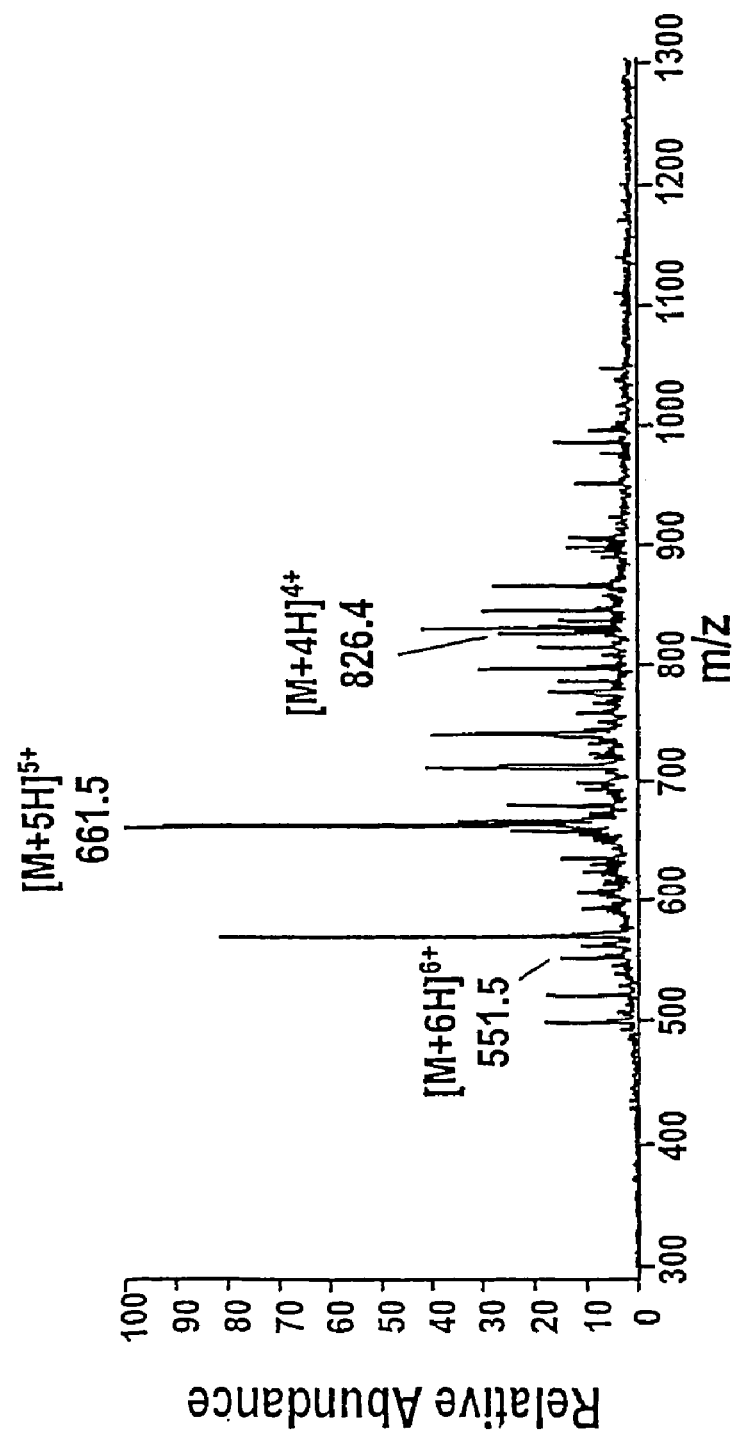

FIG. 19 shows the results of determination of the molecular weight of the finally purified endogenous RFRP-3 sample from bovine hypothalamus.

Figure 20:
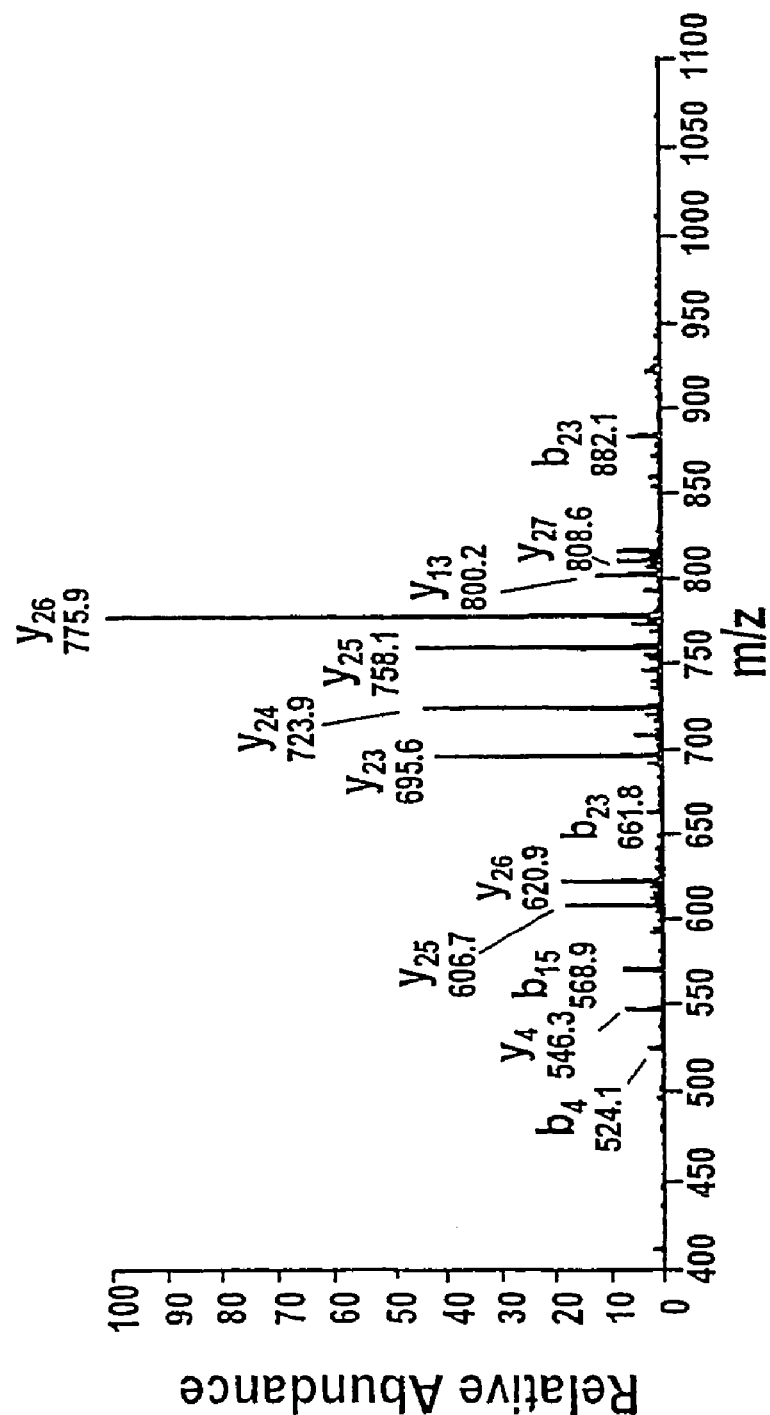

FIG. 20 shows the MS/MS spectrum of the finally purified endogenous RFRP-3 sample purified from bovine hypothalamus measured using a pentavalent molecule-related ion (m/z 661) as a precursor ion.

Figure 21:
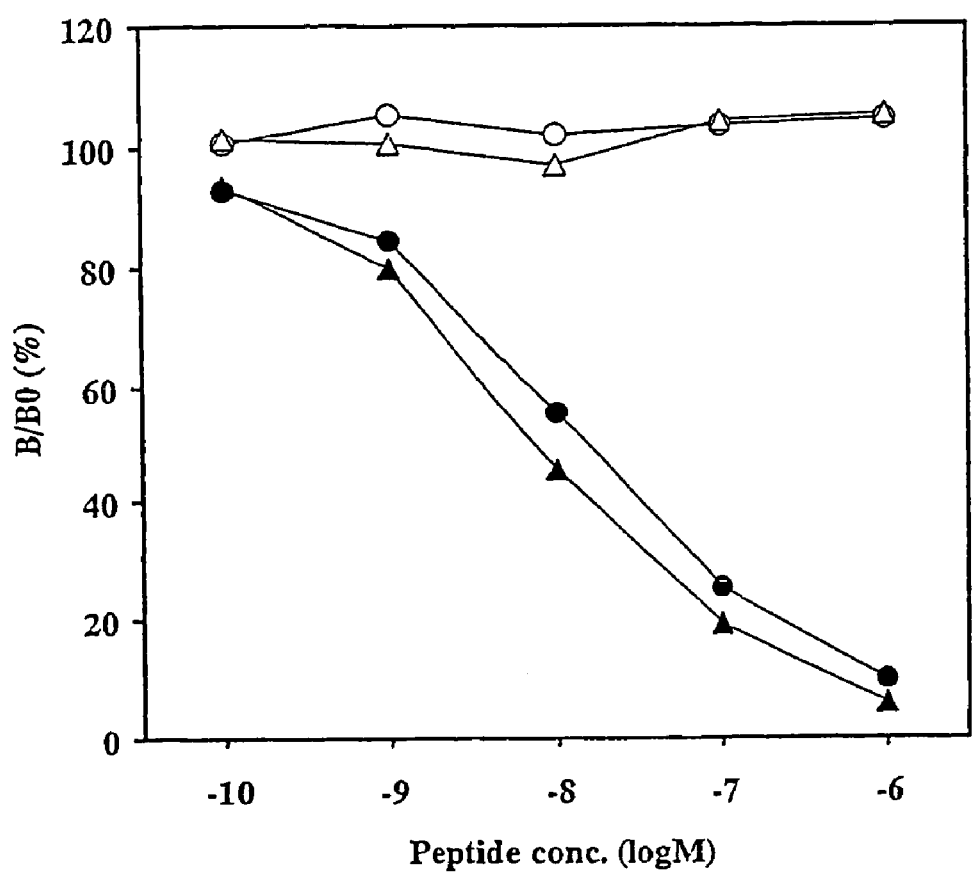

FIG. 21 shows the reactivity of RF amide-related peptides in competitive EIA using anti-rat RFRP-3 polyclonal antibody. "B" shows the absorbance when the peptide was added; "B$_0$" shows the absorbance when the peptide was not added.

BEST MODES FOR CARRYING OUT THE INVENTION

A polypeptide comprising an amino acid sequence identical or substantially identical to the amino acid sequence represented by SEQ ID NO: 1 (hereinafter, sometimes referred to as the "polypeptide of the invention") may be a polypeptide derived from cells of any kind (e.g. retinal cells, hepatocytes, splenocytes, nerve cells, glia cells, pancreatic β cells, bone marrow cells, mesangial cells, Langerhan's cells, epidermal cells, epithelial cells, endothelial cells, fibroblasts, fibrous cells, muscle cells, fat cells, immune cells (e.g. macrophages, T cells, B cells, natural killer cells, mast cells, neutrophils, basophils, eosinophils, monocytes), megakaryocytes, synovial cells, chondrocytes, osteocytes, osteoblasts, osteoclasts, mammary cells, hepatocytes or interstitial cells, or progenitor cells, stem cells or cancer cells of these cells, and so forth) of human or other warm-blooded animals (e.g. guinea pig, rat, mouse, chicken, rabbit, pig, sheep, bovine, monkey, and so forth) or any tissue in which such cells are present, such as brain, various parts of brain (e.g. retina, olfactory bulb, amygdaloid nucleus, cerebral basal nucleus, hippocampus, thalamus, hypothalamus, cerebral cortex, medulla oblongata, cerebellum), spinal cord, pituitary gland, stomach, pancreas, kidney, liver, gonad, thyroid, gall-bladder, bone marrow, adrenal gland, skin, muscle, lung, gastrointestinal tracts (e.g. large intestine, small intestine), blood vessels, heart, thymus, spleen, submandibular gland, peripheral blood, prostate, testis, ovary, placenta, uterus, bone, joint, skeletal muscle, and so forth or hemocyte lineage cells or cultured cells thereof (e.g. MEL, M1, CTLL-2, HT-2, WEHI1–3, HL-60, JOSK-1, K562, ML-1, MOLT-3, MOLT4, MOLT-10, CCRF-CEM, TALL-1, Jurkat, CCRT-HSB-2, KE-37, SKW-3, HUT-78, HUT-102, H19, U937, THP-1, HEL, JK-1, CMK, KO-812, MEG-01, and so forth). The polypeptide may also be a synthetic polypeptide.

Examples of amino acid sequences substantially identical to the amino acid sequence represented by SEQ ID NO: 1 include amino acid sequences having about 70% or more, preferably about 80% or more, more preferably about 90% or more, still more preferably about 95% or more homology to the amino acid sequence represented by SEQ ID NO: 1.

As an amino acid sequence substantially identical to the amino acid sequence represented by SEQ ID NO: 1, an amino acid sequence comprising the amino acid sequence which is from position 22 to position 180 of the amino acid sequence represented by SEQ ID NO: 1 may be given, for example.

More specific examples of amino acid sequences substantially identical to the amino acid sequence represented by SEQ ID NO: 1 include the amino acid sequence represented by SEQ ID NO: 8, SEQ ID NO: 14, SEQ ID NO: 18, SEQ ID NO: 33 or SEQ ID NO: 50.

Examples of polypeptides comprising an amino acid sequence substantially identical to the amino acid sequence represented by SEQ ID NO: 1 include those polypeptides which comprise the above-described amino acid sequence substantially identical to the amino acid sequence represented by SEQ ID NO: 1 (e.g. the amino acid sequence represented by SEQ ID NO: 8, SEQ ID NO: 14, SEQ ID NO: 18, SEQ ID NO: 33 or SEQ ID NO: 50) and has such an activity of regulating prolactin secretion as possessed by a polypeptide comprising the amino acid sequence represented by SEQ ID NO: 1.

The term "substantially identical" means that the activities of polypeptides are naturally same (e.g. physiologically or pharmacologically). Therefore, it is preferable that the activities of regulating prolactin secretion should be equivalent (e.g. about 0.1- to 100-fold, preferably about 0.5- to 10-fold, more preferably 0.5- to 2-fold). However, quantitative factors, such as the degree of activities, the molecular weights of polypeptides, may be optionally different.

The determination of activity of regulating prolactin secretion may be carried out by known methods. For example, this activity may be measured according to the procedures described later in Example 1.

The polypeptide of the present invention include the so-called muteins, such as polypeptides comprising (i) the amino acid sequence of SEQ ID NO: 1, SEQ ID NO: 8, SEQ ID NO: 14, SEQ ID NO: 18, SEQ ID NO: 33 or SEQ ID NO: 50 wherein 1–20 amino acids (preferably 1–15, more preferably 1–5, and still more preferably 1–3 amino acids) are deleted therefrom; (ii) the amino acid sequence of SEQ ID NO: 1, SEQ ID NO: 8, SEQ ID NO: 14, SEQ ID NO: 18, SEQ ID NO: 33 or SEQ ID NO: 50 wherein 1–20 amino acids (preferably 1–15, more preferably 1–5, and still more preferably 1–3 amino acids) are added thereto; (iii) the amino acid sequence of SEQ ID NO: 1, SEQ ID NO: 8, SEQ ID NO: 14, SEQ ID NO: 18, SEQ ID NO: 33 or SEQ ID NO: 50 wherein 1–20 amino acids (preferably 1–15, more preferably 1–5, and still more preferably 1–3 amino acids) are inserted thereinto; (iv) the amino acid sequence of SEQ ID NO: 1, SEQ ID NO: 8, SEQ ID NO: 14, SEQ ID NO: 18, SEQ ID NO: 33 or SEQ ID NO: 50 wherein 1–20 amino acids (preferably 1–15, more preferably 1–5, and still more preferably 1–3 amino acids); or (v) an amino acid sequence which is a combination of these sequences.

If the amino acid sequence has such an insertion, deletion or substitution as described above, the site of the insertion, deletion or substitution is not particularly restricted.

Specific examples of polypeptides comprising an amino acid sequence substantially identical to the amino acid sequence represented by SEQ ID NO: 2 include a polypeptide comprising the amino acid sequence represented by SEQ ID NO: 8, a polypeptide comprising the amino acid sequence represented by SEQ ID NO: 14, a polypeptide comprising the amino acid sequence represented by SEQ ID NO: 18, a polypeptide comprising the amino acid sequence represented by SEQ ID NO: 33, and a polypeptide comprising the amino acid sequence represented by SEQ ID NO: 50.

The polypeptides in the present specification are expressed according to the conventional description of peptides, that is, the N-terminus (amino terminus) at the left end and the C-terminus (carboxyl terminus) at the right end. The C-terminus of the polypeptide of the invention (such as a polypeptide comprising the amino acid sequence represented by SEQ ID NO: 4) may be either a carboxyl group (—COOH), a carboxylate (—COO⁻), an amide (—CONH$_2$) or an ester (—COOR).

Examples of R of the above ester group include $C_{1-6}$ alkyl groups (e.g. methyl, ethyl, n-propyl, isopropyl or n-butyl), $C_{3-8}$ cycloalkyl groups (e.g. cyclopentyl or cyclohexyl), $C_{6-12}$ aryl groups (e.g. phenyl or α-naphthyl), $C_{7-14}$ aralkyl groups such as phenyl-$C_{1-2}$ alkyl groups (e.g. benzyl or phenethyl) and α-naphthyl-$C_{1-2}$ alkyl groups (e.g. α-naphthylmethyl). In addition, the ester group also includes pivaloyloxymethyl esters that are universally used as oral esters.

When the polypeptide of the present invention has a carboxyl group (or carboxylate) at any position other than its C-terminus, the carboxyl group may be amidated or esterified; such a polypeptide is also included in the polypeptide of the invention. The ester in this case may be, for example, any of the esters mentioned above for the C-terminal ester.

Furthermore, the polypeptide of the present invention includes those polypeptides in which the N-terminal amino acid residue (e.g. Met) is protected by a protective group (e.g. $C_{1-6}$ acyl group such as $C_{1-6}$ alkanoyl group (e.g. formyl group or acetyl group)); those polypeptides in which the N-terminal Glu generated through in vivo cleavage is pyroglutaminated; those polypeptides in which a substituent on a side chain of an amino acid (e.g. —OH, —SH, amino group, imidazole group, indole group, or guannidino group) is protected by an appropriate protective group (e.g. $C_{1-6}$ acyl group such as $C_{1-6}$ alkanoyl group (e.g. formyl group or acetyl group)); and conjugated proteins such as the so-called glycoproteins to which sugar chains are linked. Hereinafter, these polypeptides may sometimes be referred to as the polypeptide of the present invention.

Specific examples of the polypeptide of the present invention include a human-derived polypeptide comprising the amino acid sequence represented by SEQ ID NO: 1, a human-derived polypeptide comprising the amino acid sequence represented by SEQ ID NO: 8, a bovine-derived polypeptide comprising the amino acid sequence represented by SEQ ID NO: 14, a rat-derived polypeptide comprising the amino acid sequence represented by SEQ ID NO: 18, a mouse-derived polypeptide comprising the amino acid sequence represented by SEQ ID NO: 33, and a rat-derived polypeptide comprising the amino acid sequence represented by SEQ ID NO: 50. For example, a human-derived polypeptide comprising the amino acid sequence represented by SEQ ID NO: 1, a human-derived polypeptide comprising the amino acid sequence represented by SEQ ID NO: 8, and a bovine-derived polypeptide comprising the amino acid sequence represented by SEQ ID NO: 14 are used preferably.

The RFRP-3 of the present invention consists of (i) an amino acid sequence which is from position 104 (Ala) to position 131 (Phe) of SEQ ID NO: 1 (SEQ ID NO: 63); (i) an amino acid sequence which is from position 101 (Ser) to position 131 (Phe) of SEQ ID NO: 1 (SEQ ID NO: 65); or (iii) the amino acid sequence which is from position 104 (Ser) to position 131 (Phe) of SEQ ID NO: 14 (SEQ ID NO: 67).

The RFRP-3 of the present invention may comprise the above-described amino acid sequence where 1–5 amino acids (preferably 1–3 amino acids) are deleted, or 1–5 amino acids (preferably 1–3 amino acids) are added, or 1–5 amino acids (preferably 1–3 amino acids) are inserted, or 1–5 amino acids (preferably 1–3 amino acids) are substituted with other amino acids; or may comprise an amino acid sequence which is a combination of these amino acid sequences.

Further, as the RFRP-3 of the present invention, a peptide may also be used which comprises at least an amino acid sequence which is from position 127 (Leu) to position 131 (Phe) of the amino acid sequence represented by SEQ ID NO: 1 or SEQ ID NO: 12 (SEQ ID NO: 69) on its C-terminal side. Specifically, a peptide consisting of an amino acid sequence which is from position 124 (Val) to position 131 (Phe) of the amino acid sequence represented by SEQ ID NO: 1 or SEQ ID NO: 12 (SEQ ID NO: 72) (RFRP-3 (8)); a peptide consisting of an amino acid sequence which is from position 125 (Pro) to position 131 (Phe) (SEQ ID NO:

71) (RFRP-3 (7)); a peptide consisting of an amino acid sequence which is from position 126 (Asn) to position 131 (Phe) of the amino acid sequence represented by SEQ ID NO: 1 or SEQ D NO: 12 (SEQ ID NO: 70) (RFRP-3 (6)); or a peptide consisting of an amino acid sequence which is from position 127 (Leu) to position 131 (Phe) of the amino acid sequence represented by SEQ ID NO: 1 or SEQ ID NO: 12 (SEQ ID NO: 69) (RFRP-3 (5)) may be used. Among all, the peptide consisting of an amino acid sequence which is from position 125 (Pro) to position 131 (Phe) of the amino acid sequence represented by SEQ ID NO: 1 (SEQ ID NO: 71) (RFRP-3 (7)); the peptide consisting of an amino acid sequence which is from position 126 (Asn) to position 131 (Phe) of the amino acid sequence represented by SEQ ID NO: 1 (SEQ ID NO: 70) (RFRP-3 (6)); or the peptide consisting of an amino acid sequence which is from position 127 (Leu) to position 131 (Phe) of the amino acid sequence represented by SEQ ID NO: 1 (SEQ ID NO: 69) (RFRP-3 (5)) are used preferably. In particular, the peptide RFRP-3 (7) consisting of an amino acid sequence which is from position 125 (Pro) to position 131 (Phe) of the amino acid sequence represented by SEQ ID NO: 1 (SEQ ID NO: 71) is used preferably. Preferably, the C-terminus of these peptides is an amide.

The C-terminus of the RFRP-3 of the present invention may be either a carboxyl group (—COOH), a carboxylate (—COO$^-$), an amide (—CONH$_2$) or an ester (—COOR) (where R has the same definition as described above). Among all, those which have an amide (CONH$_2$) on their C-terminus are preferable.

When the RFRP-3 of the present invention has a carboxyl group (or carboxylate) at any position other than its C-terminus, the carboxyl group may be amidated or esterified; such RFRP-3 is also included in the polypeptide of the present invention. The ester in this case may be, for example, any of the esters mentioned above for the C-terminal ester.

Further, like the polypeptide of the present invention described above, the RFRP-3 of the present invention also includes those peptides in which the N-terminal amino acid residue (e.g. Met) is protected by a protective group; those peptides in which the N-terminal Glu generated through in vivo cleavage is pyroglutaminated; those peptides in which a substituent on a side chain of an amino acid is protected by an appropriate protective group; and conjugated peptides such as the so-called glycopeptides to which sugar chains are linked.

The RFRP-3 of the present invention has an RF amide structure. The term "RF amide structure" means that the C-terminal of a peptide is arginine-phenylalanine-NH$_2$.

As salts of the polypeptide or the RFRP-3 of the present invention, salts formed with physiologically acceptable acids (e.g. organic or inorganic acids) or bases (e.g. alkali metals) are used. Especially preferable are physiologically acceptable acid addition salts. Examples of such salts include salts formed with inorganic acids (e.g. hydrochloric acid, phosphoric acid, hydrobromic acid or sulfuric acid) and salts formed with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid).

The polypeptide of the present invention or salts thereof or the RFRP of the invention and salts thereof can be produced from the afore-mentioned cells or tissues of human or other warm-blooded animals by known purification methods for polypeptides. Alternatively, they can also be produced by culturing a transformant comprising a DNA described later encoding the polynucleotide. They can also be produced in accordance with the procedures for peptide synthesis which are described later.

In producing the polypeptide or salts thereof or the RFRP or salts thereof from tissues or cells of human or other mammals, the relevant tissue or cell is homogenized and then the desired polypeptide, and so forth is extracted with acids, and so forth. The desired polypeptide, and so forth can be purified and isolated from the resultant extract by a combination of chromatography, such as reversed phase chromatography, ion exchange chromatography and so on.

It is useful for the synthesis of the polypeptide of the present invention or salts thereof or the RFRP of the present invention or salts thereof that any of the commercial resins available for polypeptide synthesis. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2',4'-dimethoxyphenylhydroxymethyl)phenoxy resin, and 4-(2',4'-dimethoxyphenyl-Fmoc-aminoethyl)phenoxy resin. Using such a resin, amino acids of which their α-amino groups and side chain functional groups are protected are condensed on the resin according to the amino acid sequence of the desired polypeptide by conventional condensation methods. At the final stage of the reaction, all protective groups are removed simultaneously with the cleavage of the polypeptide from the resin. Then, in a highly diluted solution, intramolecular disulfide bond formation reaction is carried out to obtain the polypeptide of the invention or a salt thereof of the RFRP of the invention of a salt thereof.

With respect to the condensation of the above-described protected amino acids, it may be utilized that various activators useful for polypeptide synthesis. Among all, carbodiimide reagents are especially preferred. Examples of carbodiimide reagents include DCC, N,N'-diisopropylcarbodiimide, and N-ethyl-N'-(3-dimethylaminoprolyl)carbodiimide. For activation by these reagents, protected amino acids and a recemization inhibitor (e.g. HOBt or HOOBt) may be directly added to the resin, or protected amino acids may be activated in advance in the form of symmetric acid anhydride, HOBt ester or HOOBt ester and then added to the resin.

The solvent used for the above-mentioned activation of protected amino acids or the condensation thereof with a resin may be appropriately selected from those solvents known to be useful for polypeptide (protein) condensation reactions. Examples of useful solvents include acid amides (e.g. N,N-dimethylformamide, N,N-dimethylacetamide or N-methylpyrrolidone), halogenated hydrocarbons (e.g. methylene chloride, or chloroform), alcohols (e.g. trifluoroethanol), sulfoxides (e.g. dimethyl sulfoxide), ethers (e.g. pyridine, dioxane, tetrahydrofuran), nitriles (e.g. acetonitrile or propionitrile), esters (e.g. methyl acetate or ethyl acetate), and suitable mixtures of these solvents. The reaction temperature may be appropriately selected from the range known to be useful for polypeptide bond-forming reactions; usually, the temperature is selected from the range from about −20° C. to about 50° C. The activated amino acid derivative is usually used in 1.5- to 4-fold excess. If the condensation is found insufficient as a result of test using the ninhydrin reaction, sufficient condensation can be achieved by repeating reactions without removing protective groups. If sufficient condensation cannot be achieved even by repeating reactions, unreacted amino acids may be acetylated with acetic anhydride or acetylimidazole so that they do not affect subsequent reactions.

Examples of useful protective groups for the amino group of raw materials include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, and Fmoc.

The carboxyl group can be protected, for example, in the form of an alkyl ester (e.g. straight-chain, branched, or cyclic alkyl esters such as methyl, ethyl, propyl, butyl, t-butyl, cyclopentyl, cyclohexyl, cycloheptyl, cyclooctyl, 2-adamantyl, and so on), aralkyl ester (e.g. benzyl, 4-nitrobenzyl, 4-methoxybenzyl, 4-chlorobenzyl, benzhydryl, and so on), phenacyl ester, benzyloxycarbonylhydrazide, t-butoxycarbonylhydrazide or tritylhydrazide.

The hydroxyl group of serine can be protected, for example, by esterification or etherification. Examples of suitable groups for this esterification include lower ($C_{1-6}$) alkanoyl groups such as acetyl, aroyl groups such as benzoyl, and carbonic acid-derived groups such as benzyloxycarbonyl and ethyloxycarbonyl. Examples of groups suitable for the etherification include benzyl, tetrahydropyranyl and t-butyl.

Examples of protective groups for the phenolic hydroxyl group of tyrosine include Bzl, $Cl_2$-Bzl, 2-nitrobenzyl, BrZ, and t-butyl.

Examples of protective groups for the imidazole ring of histidine include Tos, 4-methoxy-2,3,6-trimethylbenzenesulfonyl, DNP, benzyloxymethyl, Bum, Boc, Trt and Fmoc.

Examples of materials with activated carboxyl groups include the corresponding acid anhydrides, azides and active esters (esters of alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide and HOBt). Examples of raw materials with activated amino groups include the corresponding phosphoric acid amides.

Methods for removing (eliminating) protective groups include, for example, catalytic reduction in a hydrogen stream in the presence of a catalyst such as Pd black or Pd-carbon, acid treatment with anhydrous hydrogen fluoride, methanesulfonic acid, trifluoromethanesulfonic acid, trifluoroacetic acid or mixtures thereof, treatment with a base such as diiso-propylethylamine, triethylamine, piperidine, piperazine or the like, and reduction with sodium in liquid ammonia. The elimination reaction by the above-mentioned acid treatment is generally conducted at temperatures of about −20° C. to about 40° C. In the acid treatment, it is effective to add a cation scavenger such as anisole, phenol, thioanisole, m-cresol, p-cresol, dimethylsulfide, 1,4-butanedithiol or 1,2-ethanedithiol. The 2,4-dinitrophenyl group used as the protective group for the imidazole ring of histidine is removed by thiophenol treatment. The formyl group used as the protective group for the indole ring of tryptophan may be removed by the above-mentioned deprotection by the acid treatment in the presence of 1,2-ethanedithiol, 1,4-butanedithiol or the like, or by alkali treatment using dilute sodium hydroxide, dilute ammonia or the like.

The protection of functional groups in materials that should not be involved in the reaction, protective groups therefor, the removal of these protective groups and the activation of functional groups involved in the reaction can be appropriately selected from groups or methods known in the art.

An alternative method for obtaining amides of the polypeptide or the RFRP of the invention comprises, for example, protecting the α-carboxyl group of the C-terminal amino acid by amidation, extending the peptide (polypeptide) chain to a desired length on the side of the amino group, preparing a polypeptide with its N-terminal α-amino group selectively deprotected, preparing a polypeptide with its C-terminal carboxyl group selectively deprotected, and condensing these two polypeptides in a mixed solvent such as described above. Details of this condensation reaction are the same as described above. After purification of the protected polypeptide thus obtained by condensation, all the protective groups are removed by the method described above to thereby to provide a desired crude polypeptide. This crude polypeptide is purified by various known purification techniques and lyophilized to provide the desired polypeptide or RFRP in an amide form.

As a method for obtaining esters of the polypeptide or the RFRP of the invention, for example, the α-caboxyl group of the C-terminal amino acid is condensed with a desired alcohol to prepare the corresponding amino acid ester, and then this ester is subjected to the same procedures as described above in the preparation of amides to thereby obtain the desired polypeptide or RFRP in an ester form.

The RFRP of the invention or salts thereof can be produced by known methods for peptide synthesis. Alternatively, the RFRP or salts thereof may be produced by digesting the polypeptide of the present invention with an appropriate peptidase. The method for peptide synthesis may be solid-phase synthesis or liquid-phase synthesis. Briefly, a desired peptide can be produced by condensing a partial peptide or amino acids capable of constituting the RFRP of the present invention with the remaining part thereof and, if the product has protective groups, removing the protective groups. Examples of condensation methods and methods for removal of protective groups known in the art include those described in the following references (i) to (v).

(i) M. Bodanszky & M. A. Ondetti, Peptide Synthesis, Interscience Publishers, New York, 1966
(ii) Schroeder & Luebke, The Peptide, Academic Press, New York, 1965
(iii) Nobuo Izumiya et al., Fundamentals and Experiments in Peptide Synthesis, Maruzen, 1975
(iv) Haruaki Yajima and Shumpei Sakakibara, Biochemical Experiment Series 1, Polypeptide Chemistry IV, 205, 1977, and
(v) Haruaki Yajima (ed.), Development of Mediciens (Continued), Vol. 14, Peptide Synthesis, Hirokawa Shoten After the reaction, the RFRP of the present invention can be isolated and purified by a combination of conventional purification techniques such as solvent extraction, distillation, column chromatography, liquid chromatography, and recrystallization. If the obtained RFRP is free, it can be converted to a suitable salt by known methods or methods based thereon. On the contrary, if the RFRP is obtained in a salt form, it can be converted to be free or another salt by known methods or methods based thereon.

The polynucleotide encoding the polypeptide of the present invention may be any polynucleotide as long as it comprises a nucleotide sequence encoding the polypeptide of the invention (DNA or RNA; preferably, DNA). The polynucleotide may be a DNA or RNA (such as mRNA) encoding the polypeptide of the present invention, and may be double-stranded or single-stranded. If the polynucleotide is double-stranded, it may be a double-stranded DNA, a double-stranded RNA, or a DNA:RNA hybrid. If the polynucleotide is single-stranded, it may be a sense strand (i.e. coding strand) or an anti-sense strand (i.e. non-coding strand).

With the polynucleotide encoding the polypeptide of the present invention, it is possible to quantitatively determine the mRNA of the polypeptide of the present invention by such methods as described in New PCR and Its Application (Extra Issue of Experimental Medicine), 15 (7), 1997 or modifications thereof.

The DNA encoding the polypeptide of the present invention may be any DNA as long as it comprises the above-described nucleotide sequence encoding the polypeptide of the present invention. The DNA may be genomic DNA, genomic DNA library, cDNA derived from the above-mentioned cells or tissues, cDNA library derived from the above-mentioned cells or tissues, or synthetic DNA.

Vectors used for library construction may be any vectors such as bacteriophage, plasmid, cosmid, phagemid, and so on. Alternatively, total RNA or mRNA fraction may be prepared from the above-mentioned cells or tissues, followed by direct amplification by reverse transcriptase polymerase chain reaction (hereinafter, abbreviated to "RT-PCR").

Specific examples of the DNA encoding the polypeptide of the present invention include any DNA comprising the nucleotide sequence represented by SEQ ID NO: 2, SEQ ID NO: 9, SEQ ID NO: 15, SEQ ID NO: 19, SEQ ID NO: 34 or SEQ ID NO: 51; or any DNA which comprises a nucleotide sequence hybridizing to the nucleotide sequence represented by SEQ ID NO: 2, SEQ ID NO: 9, SEQ ID NO: 15, SEQ ID NO: 19, SEQ ID NO: 34 or SEQ ID NO: 51 under highly stringent conditions and encodes a polypeptide which substantially has an activity (e.g. cell stimulatory activity) naturally same to the activity of the polypeptide of the present invention.

As DNAs capable of hybridizing to the nucleotide sequence represented by SEQ ID NO: 2, SEQ ID NO: 9, SEQ ID NO: 15, SEQ ID NO: 19, SEQ ID NO: 34 or SEQ ID NO: 51 under highly stringent conditions, DNAs comprising a nucleotide sequence having about 70% or more, preferably about 80% or more, more preferably about 90% or more, still more preferably about 95% or more homology to the nucleotide sequence represented by SEQ ID NO: 2 may be used, for example.

Hybridization can be carried out according to known methods or methods based thereon, e.g. those methods described in "Molecular Cloning," 2nd Ed. (J. Sambrook et al., Cold Spring Harbor Lab. Press, 1989). When commercial libraries are used, hybridization can be carried out in accordance with the methods described in the instructions attached thereto; more preferably, hybridization is carried out under highly stringent conditions.

"Highly stringent conditions" refers to, for example, conditions where the sodium concentration is about 1940 mM, preferably about 19–20 mM, and the temperature is about 50–70° C., preferably about 60–65° C. In particular, conditions where the sodium concentration is about 19 mM and the temperature is about 65° C. are most preferable.

More specifically, as a DNA encoding a polypeptide comprising the amino acid sequence represented by SEQ ID NO: 1, a DNA comprising the nucleotide sequence represented by SEQ ID NO: 2 may be used, for example. As a DNA encoding a polypeptide comprising the amino acid sequence represented by SEQ ID NO: 8, a DNA comprising the nucleotide sequence represented by SEQ ID NO: 9 may be used, for example. As a DNA encoding a polypeptide comprising the amino acid sequence represented by SEQ ID NO: 14, a DNA comprising the nucleotide sequence represented by SEQ ID NO: 15 may be used, for example. As a DNA encoding a polypeptide comprising the amino acid sequence represented by SEQ ID NO: 18, a DNA comprising the nucleotide sequence represented by SEQ ID NO: 19 may be used, for example. As a DNA encoding a polypeptide comprising the amino acid sequence represented by SEQ ID NO: 33, a DNA comprising the nucleotide sequence represented by SEQ ID NO: 34 may be used, for example. As a DNA encoding a polypeptide comprising the amino acid sequence represented by SEQ ID NO: 50, a DNA comprising the nucleotide sequence represented by SEQ ID NO: 51 may be used, for example.

The polynucleotide encoding the RFRP-3 of the present invention may be any polynucleotide as long as it comprises a nucleotide sequence encoding the RFRP-3 of the invention (DNA or RNA; preferably, DNA). The polynucleotide may be a DNA or RNA (such as mRNA) encoding the RFRP-3 of the present invention, and may be double-stranded or single-stranded. When the polynucleotide is double-stranded, it may be a double-stranded DNA, a double-stranded RNA, or a DNA:RNA hybrid. When the polynucleotide is single-stranded, it may be a sense strand (i.e. coding strand) or an anti-sense strand (i.e. non-coding strand).

With the polynucleotide encoding the RFRP-3 of the present invention, it is possible to quantitatively determine the mRNA of the RFRP-3 of the present invention by such methods as described in New PCR and Its Application (Extra Issue of Experimental Medicine), 15 (7), 1997 or modifications thereof.

The DNA encoding the RFRP-3 of the present invention may be any DNA as long as it comprises the above-described nucleotide sequence encoding the RFRP-3 of the present invention. The DNA may be genomic DNA, genomic DNA library, cDNA derived from the above-mentioned cells or tissues, cDNA library derived from the above-mentioned cells or tissues, or synthetic DNA.

Specific examples of the DNA encoding the RFRP-3 of the present invention include:

(i) DNAs encoding a peptide consisting of an amino acid sequence which is from position 104 (Ala) to position 131 (Phe) of SEQ ID NO: 1 (SEQ ID NO: 63); or DNAs comprising a nucleotide sequence hybridizing to these DNAs under highly stringent conditions;

(ii) DNAs encoding a peptide consisting of an amino acid sequence which is from position 101 (Ser) to position 131 (Phe) of SEQ ID NO: 1 (SEQ ID NO: 65); or DNAs comprising a nucleotide sequence hybridizing to these DNAs under highly stringent conditions;

(iii) DNAs encoding a peptide consisting of an amino acid sequence which is from position 104 (Ala) to position 131 (Phe) of SEQ ID NO: 14 (SEQ ID NO: 67); or DNAs comprising a nucleotide sequence hybridizing to these DNAs under highly stringent conditions.

"Highly stringent conditions" refers to, for example, conditions wherein sodium concentration is about 19–40 mM, preferably about 19–20 mM, and temperature is about 50–70° C., preferably about 60–65° C. In particular, conditions wherein sodium concentration is about 19 mM and temperature is about 65° C. are most preferable.

More specifically;

(i) as the DNA encoding a peptide consisting of an amino acid sequence which is from position 104 (Ala) to position 131 (Phe) of SEQ ID NO: 1 (SEQ ID NO: 63), a DNA consisting of a nucleotide sequence which is from position 310 to position 393 of the nucleotide sequence represented by SEQ ID NO: 2 (SEQ ID NO: 64) may be given, for example;

(ii) as the DNA encoding a peptide consisting of an amino acid sequence which is from position 101 (Ser) to position 131 (Phe) of SEQ ID NO: 1 (SEQ ID NO: 65), a DNA consisting of a nucleotide sequence which is from position 301 to position 393 of the nucleotide sequence represented by SEQ ID NO: 2 (SEQ ID NO: 66) may be given, for example; and (iii) as the DNA encoding a peptide consisting of an amino acid sequence which is from position 104 (Ala) to position 131 (Phe) of SEQ ID NO: 14 (SEQ ID NO: 67), a DNA consisting of a nucleotide sequence which is from position 310 to position 393 of the nucleotide sequence represented by SEQ ID NO: 15 (SEQ ID NO: 68) may be given, for example.

Further;

(iv) as the DNA encoding a peptide consisting of an amino acid sequence which is from position 125 (Pro) to position 131 (Phe) of SEQ ID NO: 1, a DNA consisting of a nucleotide sequence which is from position 373 to position 393 of SEQ ID NO: 2 may be given, for example;

(v) as the DNA encoding a peptide consisting of an amino acid sequence which is from position 126 (Asn) to position 131 (Phe) of SEQ ID NO: 1, a DNA consisting of a nucleotide sequence which is from position 376 to position 393 of SEQ ID NO: 2 may be given, for example; and (vi) as the DNA encoding a peptide consisting of an amino acid sequence which is from position 127 (Leu) to position 131 (Phe) of SEQ ID NO: 1, a DNA consisting of a nucleotide sequence which is from position 379 to position 393 of SEQ ID NO: 2 may be given, for example.

The polypeptide of the invention or RFRP-3 thereof, the receptor protein of the invention or RFRP-3 thereof described later, and DNAs encoding these proteins and peptides may be labeled by known methods. Specifically, they may be labeled with isotopes, fluorescently labeled (e.g. with fluorescein, and so forth), biotinylated, or labeled with enzymes.

The cloning of a DNA encoding the full length of the polypeptide or the RFRP-3 of the invention (hereinafter, in the explanation of the cloning and expression of DNAs encoding these polypeptides and so forth, sometimes these peptides and so forth may be briefly referred to as the polypeptide of the invention) can be performed either by PCR amplification from genomic DNA or cDNA using synthetic DNA primers each having a partial nucleotide sequence of the polypeptide of the invention, or by a method where a desired DNA fragment is selected by hybridizing DNA incorporated into an appropriate vector to a labeled DNA probe, the DNA probe being a DNA fragment or a synthetic DNA encoding a part or full length of the polypeptide of the invention. The hybridization can be carried out, for example, according to the method described in "Molecular Cloning", 2nd Edition (J. Sambrook et al., Cold Spring Harbor Lab. Press, 1989). If commercial libraries are used, the hybridization can be carried out according to the instructions attached thereto.

Substitution of the nucleotide sequence of a DNA can be performed by known methods such as ODA-LA PCR, the gapped duplex method, the Kunkel method or modifications thereof, using known kits such as Mutan™-Super Express Km (Takara), Mutan™-K (Takara) and so forth.

The cloned DNA encoding the polypeptide of the invention may be used as it is or after digestion with restriction enzymes or addition of linkers, depending on purposes. The DNA may have ATG at its 5' end as a translation initiation codon and TAA, TGA, or TAG at its 3' end as a translation termination codon. The translation initiation and termination codons may also be added by using appropriate synthetic DNA adapters.

Expression vectors for the polypeptide of the invention can be prepared by, for example, (a) digesting a desired DNA fragment from a DNA encoding the polypeptide of the invention and (b) ligating the DNA fragment to an appropriate expression vector downstream of its promoter.

Examples of vectors useful in the invention include plasmids derived from *Escherichia coli* (e.g. pBR322, pBR325, pUC12, and pUC13); plasmids derived from *Bacillus subtilis* (e.g. pUB110, pTP5 and pC194); plasmids derived from yeast (e.g. pSH19 and pSH15); bacteriophages such as λ-phage; animal viruses such as retrovirus, vaccinia virus, baculovirus; and other vectors such as pA1-11, pXT1, pRc/CMV, pRc/RSV, pcDNAI/Neo and so forth.

Any promoter may be used in the invention as long as it is appropriate for the host that will be used for expressing a desired gene. When the host is an animal cell, examples of promoters useful in the invention include SRα promoter, SV40 promoter, HIV LTR promoter, CMV promoter and HSV-TK promoter.

Among these promoters, CMV (cytomegalovirus) promoter, SRα promoter or the like is preferably used. When the host is an *Escherichia* bacterium, trp promoter, lac promoter, recA promoter, λP$_L$ promoter, lpp promoter, T7 promoter or the like is preferably used. When the host is a *Bacillus* bacterium, SPO1 promoter, SPO2 promoter, penP promoter or the like is preferably used. When the host is yeast, PHO5 promoter, PGK promoter, GAP promoter, ADH promoter, or the like is preferably used. When the host is insect cell, polyhedrin promoter, P10 promoter or the like is preferably used.

The expression vectors may, if desired, further comprise enhancers, splicing signals, polyadenylation signals, selective markers, SV40 replication origin (hereinafter, sometimes abbreviated to "SV40 ori") and the like. Examples of selective markers useful in the invention include dihydrofolate reductase (hereinafter, sometimes abbreviated to "dhfr") gene [methotorexate (MTX) resistance], ampicillin resistance gene (hereinafter, sometimes abbreviated to "Amp$^r$"), neomycin resistance gene [hereinafter, sometimes abbreviated to "Neo$^r$": G418 resistance] and the like. When dhfr gene-deficient Chinese hamster cells are used in combination with dhfr gene as a selective marker, a desired gene may be selected even in a thymidine-free medium.

Furthermore, a signal sequence appropriate for the host may be added, if necessary, to the N-terminal of the polypeptide of the invention. When the host is an *Escherichia* bacterium, the utilizable signal sequences may include PhoA signal sequence, OmpA signal sequence or the like may be added. When the host is a *Bacillus* bacterium, α-amylase signal sequence, subtilisin signal sequence, or the like may be added. When the host is yeast, MFα signal sequence, SUC2 signal sequence or the like may be added. When the host is animal cell, insulin signal sequence, α-interferon signal sequence, antibody molecule signal sequence, or the like may be used.

Using the thus constructed vector comprising a DNA encoding the polypeptide of the invention, transformants can be prepared.

Examples of hosts useful for this purpose include bacteria belonging to the genus *Escherichia*, bacteria belonging to the genus *Bacillus*, yeasts, insect cells, insects, and animal cells.

Specific examples of bacteria belonging to the genus *Escherichia* useful in the invention include *E. coli* K12 DH1 [Proc. Natl. Acad. Sci. USA, Vol. 60, 160 (1968)], JM103 [Nucleic Acids Research, Vol. 9, 309 (1981)], JA221 [Journal of Molecular Biology, Vol. 120, 517 (1978)]), HB101

[Journal of Molecular Biology, Vol, 41, 459 (1969)] and C600 [Genetics, Vol. 39, 440 (1954)].

Specific examples of bacteria belonging to the genus *Bacillus* useful in the invention include *B. subtilis* MI114 [Gene, Vol. 24, 255 (1983)] and 207–21 [Journal of Biochemistry, Vol. 95, 87 (1984)].

Specific examples of yeasts useful in the invention include *Saccharomyces cerevisiae* AH22, AH22R⁻, NA87-11A, DKD-5D and 20B-12, *Schizosaccharonyces pombe* NCYC1913 and NCYC2036, and *Pichia pastoris* KM71.

Specific examples of insect cells useful in the invention include, when the virus used is AcNPV, a cell line derived from larvae of *Spodoptera fugiperda* (Sf cells), MG1 cells derived from the midgut of *Trichoplusia ni*, High Five™ cells derived from eggs of *Trichoplusia ni*, *Mamestra brassicae*-derived cells and *Estigmena acrea*-derived cells. When the virus used is BmNPV, insect cells such as a silkworm-derived cell line (*Bombyx mori* N cells; BmN cells) may be used. Specific examples of Sf cells useful in the invention include Sf9 cells (ATCC CRL 1711) and Sf21 cells [both disclosed in Vaughn J. L. et al., In Vivo, 13, 213–217 (1977)].

Specific examples of insects useful in the invention include larvae of silkworm (Maeda et al., Nature, 315, 592 (1985)).

Specific examples of animal cells useful in the invention include simian cell COS-7, Vero cells, Chinese hamster cell CHO (hereinafter, abbreviated to "CHO cells"), sdhfr gene-deficient Chinese hamster cell CHO (hereinafter, abbreviated to "CHO(dhfr⁻) cells"), mouse L cells, mouse AtT-20 cells, mouse myeloma cells, rat GH3 cells, and human FL cells.

Transformation of bacteria belonging to the genus *Escherichia* can be performed in accordance with methods disclosed, for example, in Proc. Natl. Acad. Sci. USA, Vol. 69, 2110 (1972) and Gene, Vol. 17, 107 (1982).

Transformation of bacteria belonging to the genus *Bacillus* can be performed in accordance with methods disclosed, for example, in Molecular & General Genetics, Vol. 168, 111 (1979).

Transformation of yeasts can be performed in accordance with methods disclosed, for example, in Methods in Enzymology, 194, 182–187(1991) and Proc. Natl. Acad. Sci. USA, Vol. 75, 1929 (1978).

Transformation of insect cells or insects can be performed in accordance with methods disclosed, for example, in Bio/Technology, 6, 47–55 (1988).

Transformation of animal cells can be performed by methods disclosed, for example, in Cell Engineering, Separate Vol. 8, New Cell Engineering Experiment Protocol, 263–267 (1995) (Shujunsha Co.) and Virology, Vol. 52, 456 (1973).

Thus, transformants transformed with the expression vector comprising a DNA encoding the polypeptide can be obtained.

As a medium to culture transformants obtained from *Escherichia* or *Bacillus* bacteria as hosts, a liquid medium is appropriate. The medium may contain carbon sources, nitrogen sources, minerals, and so on which are necessary for the growth of the transformant. As carbon sources, glucose, dextrin, soluble starch, sucrose or the like may be enumerated. As nitrogen sources, organic or inorganic substances such as ammonium salts, nitrates, corn steep liquor, peptone, casein, meat extract, bean cake, potato extract, or the like may be enumerated. As minerals, calcium chloride, sodium dihydrogen phosphate, magnesium chloride, or the like may be enumerated. Further, yeast, vitamins, growth-promoting factors, and so forth may also be added to the medium. Preferable pH of the medium is about 5–8.

As a medium to culture *Escherichia* bacteria, M9 medium containing glucose and casamino acid [Miller, Journal of Experiments in Molecular Genetics, 431–433, Cold Spring Harbor Laboratory, New York, (1972)] is preferable, for example. If necessary, medicines such as 3β-indolyl acrylic acid can be added to the medium to improve the efficiency of the promoter.

When the host is an *Escherichia* bacterium, the transformant is cultured usually at about 15–43° C. for about 3–24 hours. If necessary, aeration and stirring may be applied.

When the host is a *Bacillus* bacterium, the transformant is cultured usually at about 30–40° C. for about 6–24 hours. If necessary, aeration and stirring may also be applied.

As a medium to culture transformants obtained from yeasts as hosts, a medium such as Burkholder minimum medium [Bostian, K. L. et al., Proc. Natl. Acad. Sci. USA, Vol. 77, 4505 (1980)] or SD medium containing 0.5% casamino acid [Bitter, G. A. et al., Proc. Natl. Acad. Sci. USA, Vol. 81, 5330 (1984)] may be used, for example. It is preferable that the pH of the medium be adjusted to about 5–8. The transformant is cultured usually at about 20–35° C. for about 24–72 hours. If necessary, aeration and stirring may be applied.

As a medium to culture transformants obtained from insect cells or insects as hosts, Grace's Insect Medium [Grace, T. C. C., Nature, 195, 788 (1962)] supplemented with additives such as inactivated 10% bovine serum may be used, for example. It is preferable that the pH of the medium be adjusted to about 6.2–6.4. The transformant is cultured usually at about 27° C. for about 3–5 days. If necessary, aeration and stirring may be applied.

As a medium to culture transformants obtained from animal cells as hosts, examples of useful media include MEM medium [Science, Vol. 122, 501 (1952)], DMEM medium [Virology, Vol. 8, 396 (1959)], RPMI 1640 medium [Journal of the American Medical Association, Vol. 199, 519 (1967)] and 199 medium [Proceedings of the Society of the Biological Medicine, Vol. 73, 1 (1950)] each containing about 5–20% fetal calf serum. Preferable pH of the medium is from about 6 to about 8. The transformant is cultured usually at about 30–40° C. for about 15–60 hours. If necessary, aeration and stirring may be applied.

Thus, it is possible to allow the transformant to produce the polypeptide of the invention in its cell membrane, and so forth.

Separation and purification of the polypeptide of the invention from the resultant culture can be carried out, for example, according to the methods described below.

For extraction of the polypeptide of the invention from cultured microorganisms or cells, the microorganism cells are harvested by known methods after the cultivation, suspended in a suitable buffer, and disrupted by sonication or by lysozyme and/or freezing and thawing, and so forth. Then, a crude extract of the polypeptide extract is obtained by centrifugation or filtration. The buffer may contain a protein denaturing agent such as urea or guanidine hydrochloride, or a surfactant such as Triton X-100™. If the polypeptide is secreted into the culture broth, the supernatant is separated from the microorganisms or cells after completion of the cultivation and collected by known methods.

Purification of the polypeptide of the invention contained in the thus obtained culture supernatant or extract can be performed by an appropriate combination of known methods for separation and purification. These known methods include methods utilizing solubility (such as salting out or sedimentation with solvents), methods mainly utilizing difference in molecular weight (such as dialysis, ultrafiltration, gel filtration and SDS-polyacrylamide gel electrophoresis), methods utilizing difference in electric charge (such as ion-exchange chromatography), methods utilizing specific affinity (such as affinity chromatography), methods utilizing difference in the hydrophobicity (such as reversed-phase high-performance liquid chromatography), and methods utilizing difference in isoelectric point (such as isoelectric electrophoresis).

When the thus obtained polypeptide of the invention is a free form, it can be converted into the above-described salt by known methods or methods based thereon. On the contrary, when the desired protein is obtained in a salt form, the salt can be converted into a free form or another salt according to known methods or methods based thereon.

The polypeptide produced by the transformant can be arbitrarily modified or a part thereof can be removed therefrom by using an appropriate protein modification enzyme before or after the purification. Examples of such protein modification enzymes include trypsin, chymotrypsin, arginyl endopeptidase, protein kinase and glycosidase.

The presence or the activity of the thus produced polypeptide of the invention or salts thereof can be measured by binding experiments using labeled ligands, enzyme immunoassays using specific antibodies, and so on.

As a specific example of the receptor for the polypeptide of the invention, or amides or esters thereof, or salts thereof, or the receptor for the RFRP-3 of the invention, or amides or esters thereof, or salts thereof (hereinafter, sometimes referred to as the "receptor protein of the invention"), a receptor protein comprising an amino acid sequence substantially identical to the amino acid sequence represented by SEQ ID NO: 37 (OT7T022) may be given.

The receptor protein used in the invention (hereinafter, referred to as the "receptor protein of the invention") may be a protein derived from cells of any kind (e.g. splenocytes, nerve cells, glia cells, pancreatic β cells, bone marrow cells, mesangial cells, Langerhan's cells, epidermal cells, epithelial cells, endothelial cells, fibroblasts, fibrous cells, muscle cells, fat cells, immune cells (e.g. macrophages, T cells, B cells, natural killer cells, mast cells, neutrophils, basophils, eosinophils, monocytes), megakaryocytes, synovial cells, chondrocytes, osteocytes, osteoblasts, osteoclasts, mammary cells, hepatocytes or interstitial cells, or progenitor cells, stem cells or cancer cells of these cells and so forth) of mammals (e.g. human, guinea pig, rat, mouse, rabbit, pig, sheep, bovine, monkey and so forth) and hemocyte lineage cells or any tissue in which such cells are present, such as brain, various parts of brain (e.g. olfactory bulb, amygdaloid nucleus, cerebral basal nucleus, hippocampus, thalamus, hypothalamus, cerebral cortex, medulla oblongata, cerebellum, occipital lobe, frontal lobe, temporal lobe, putamen, caudate nucleus, callosum, nigra), spinal cord, pituitary gland, stomach, pancreas, kidney, liver, gonad, thyroid, gall-bladder, bone marrow, adrenal gland, skin, muscle, lung, gastrointestinal tracts (e.g. large intestine, small intestine), blood vessels, heart, thymus, spleen, submandibular gland, peripheral blood, peripheral blood cells, prostate, testis, ovary, placenta, uterus, bone, joint, skeletal muscle and so forth (especially, brain and various parts thereof). The receptor protein may also be a synthetic protein.

Examples of amino acid sequences substantially identical to the amino acid sequence represented by SEQ ID NO: 37 include amino acid sequences having about 50% or more, preferably about 70% or more, more preferably about 80% or more, still more preferably about 90% or more homology to the amino acid sequence represented by SEQ ID NO: 37.

As a protein comprising an amino acid sequence substantially identical to the amino acid sequence represented by SEQ ID NO: 37, for example, a protein is preferable which comprises an amino acid sequence substantially identical to the amino acid sequence represented by SEQ ID NO: 37 and has an activity substantially the same as the activity of a protein comprising the amino acid sequence represented by SEQ ID NO: 37. Specifically, a protein comprising the amino acid sequence represented by SEQ ID NO: 54 may be given.

Examples of substantially the same activities include ligand binding activity or the effect of signal transduction. The term, "substantially the same" means that these activities are the naturally same. Therefore, it is preferable that activities such as ligand binding activity or the effect of signal transduction should be equivalent (e.g. about 0.01- to 100 fold, preferably about 0.5- to 20-fold, more preferably 0.5- to 2-fold). However, quantitative factors, such as the degree of activities, the molecular weights of proteins, may be different.

Activities such as ligand binding activity or the effect of signal transduction may be measured according to known methods. For example, such activities may be measured according to the ligand determination method or screening method described later.

Further, as the receptor protein of the invention, proteins having the following amino acid sequences (i) to (iv) may also be used: (i) the amino acid sequence of SEQ ID NO: 37 or SEQ ID NO: 54 wherein one or two or more amino acids (preferably about 1–30, more preferably about 1–10, and still more preferably a few (one or two) amino acids) are deleted therefrom, (ii) the amino acid sequence of SEQ ID NO: 37 or SEQ ID NO: 54 wherein one or two or more amino acids (preferably about 1–30, more preferably about 1–10, and still more preferably a few (one or two) amino acids) are added thereto, (iii) the amino acid sequence of SEQ ID NO: 37 or SEQ ID NO: 54 wherein one or two or more amino acids (preferably about 1–30, more preferably about 1–10, and still more preferably a few (one or two) amino acids) are substituted with other amino acids, or (iv) an amino acid sequence which is a combination of the above amino acid sequences.

The receptor proteins in the present specification are expressed in accordance with the conventions for description of peptides, that is, the N-terminus (amino terminus) at the left end and the C-terminus (carboxyl terminus) at the right end. The C-terminus of the receptor protein used in the invention may be either a carboxyl group (—COOH), a carboxylate (—COO$^-$), an amide (—CONH$_2$) or an ester (—COOR).

Examples of R of the above ester group include $C_{1-6}$ alkyl groups (e.g. methyl, ethyl, n-propyl, isopropyl or n-butyl), $C_{3-8}$ cycloalkyl groups (e.g. cyclopentyl or cyclohexyl), $C_{6-12}$ aryl groups (e.g. phenyl or α-naphthyl), $C_{7-14}$ aralkyl groups such as phenyl-$C_{1-2}$ alkyl groups (e.g. benzyl or phenethyl) and α-naphthyl-$C_{1-2}$ alkyl groups (e.g. α-naphthylmethyl). In addition, the ester group also includes pivaloyloxymethyl esters that are universally used as oral esters.

When the receptor protein of the invention has a carboxyl group (or carboxylate) at any position other than its C-terminus, the carboxyl group may be amidated or esterified; such a protein is also included in the receptor protein of the invention. The ester in this case may be, for example, any of the esters mentioned above for the C-terminal ester.

Further, the receptor protein of the present invention also includes those proteins in which the amino group of the N-terminal Met residue is protected by a protective group (e.g. $C_{1-6}$ acyl group such as $C_{2-6}$ alkanoyl group (e.g. formyl group or acetyl group)); those proteins in which the N-terminal Glu generated through in vivo cleavage is pyroglutaminated; those proteins in which a substituent on a side chain of an amino acid (e.g. —OH, —SH, amino group, imidazole group, indole group, or guannidino group) is protected by an appropriate protective group (e.g. $C_{1-6}$ acyl group such as $C_{2-6}$ alkanoyl group (e.g. formyl group or acetyl group)); and conjugated proteins such as the so-called glycoproteins to which sugar chains are linked.

Specific examples of the receptor protein of the invention include, but are not limited to, a rat-derived receptor protein consisting of the amino acid sequence represented by SEQ ID NO: 37 and a human-derived receptor protein consisting of the amino acid sequence represented by SEQ ID NO: 54.

The partial peptide of the receptor protein of the invention may be any partial peptide as long as it is a partial peptide of the above-described receptor protein. For example, a partial peptide of the receptor protein molecule of the invention that is a site exposed outside of the cell membrane and has receptor-binding activity may be used.

Specifically, as a partial peptide of the receptor protein comprising the amino acid sequence represented by SEQ ID NO: 37 or SEQ ID NO: 54, a peptide comprising an extracellular domain (i.e. hydrophilic site) as determined by hydrophobicity plot analysis may be used. Alternatively, a peptide comprising a hydrophobic site in one of its parts may also be used. Peptides comprising individual domains individually may be used; alternatively, partial peptides comprising a plurality of domains may also be use.

The number of amino acids in the partial peptide of the receptor protein of the invention is at least 20, preferably at least 50, more preferably at least 100 of the above-mentioned amino acid sequence constituting the receptor protein.

The "substantially identical" amino acid sequence means that an amino acid sequence having about 50% or more, preferably about 70% or more, more preferably about 80% or more, still more preferably about 90% or more, most preferably about 95% or more homology to those amino acid sequences.

The term "substantially the same activity" means as defined above. The measurement of the substantially the same activity may be performed as described above.

Further, the partial peptide of the receptor protein of the invention may have the above-described amino acid sequence in which one or two or more (preferably, about 1–10, more preferably a few (one or two)) amino acids are deleted; or one or two or more (preferably, about 1–20, more preferably about 1–10, still more preferably a few (one or two)) amino acids are added; or one or two or more (preferably, about 1–10, more preferably a few (one or two)) amino acids are substituted with other amino acids.

Further, the C-terminus of the partial peptide of the receptor protein of the invention may be either a carboxyl group (—COOH), a carboxylate (—COO⁻), an amide (—CONH$_2$) or an ester (—COOR) (where R is as defined above)

When the partial peptide of the receptor protein of the invention has a carboxyl group (or carboxylate) at any position other than its C-terminus, the carboxyl group may be amidated or esterified; such a peptide is also included in the partial peptide of the receptor protein of the invention.

The ester in this case may be, for example, any of the esters mentioned above for the C-terminal ester.

Further, like the receptor protein described above, the partial peptide of the receptor protein of the present invention also includes those peptides in which the amino group of the N-terminal Met residue is protected by a protective group; those peptides in which the N-terminal Glu generated through in vivo cleavage is pyroglutaminated; those proteins in which a substituent on a side chain of an amino acid is protected by an appropriate protective group; and conjugated peptides such as the so-called glycopeptides to which sugar chains are linked.

As salts of the receptor protein of the invention or partial peptides thereof, especially preferable are physiologically acceptable acid addition salts. Examples of such salts include salts formed with inorganic acids (e.g. hydrochloric acid, phosphoric acid, hydrobromic acid or sulfuric acid) and salts formed with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid).

The receptor protein of the invention or salts thereof can be produced from the afore-mentioned cells or tissues of human or other mammals by known purification methods for proteins. Alternatively, they can also be produced by culturing a transformant comprising a DNA described later encoding the receptor protein of the invention (as a host, the same host for the transformant comprising a DNA encoding the polypeptide of the invention may be used, for example). Such a transformant may be prepared in accordance with the procedures for preparing the transformant comprising a DNA encoding the polypeptide of the invention. Alternatively, they can be produced in accordance with the procedures for peptide synthesis which are described earlier.

When the receptor protein or salts thereof are produced from tissues or cells of human or other mammals, the relevant tissue or cell is homogenized and then the desired protein and so forth is extracted with acids and so forth. The desired protein and so forth can be purified and isolated from the resultant extract by a combination of chromatography, such as reversed phase chromatography, ion exchange chromatography and so on.

The partial peptide of the receptor protein of the invention or salts of the partial peptide may be produced in accordance with known methods of peptide synthesis. Alternatively, they may be produced by digesting the receptor protein of the invention with an appropriate peptidase.

The receptor protein of the invention or salts thereof, and the partial peptide of the receptor protein or amides, esters or salts thereof may be produced in accordance with the above-described procedures for the synthesis of the polypeptide of the invention, or amide, esters or salts thereof.

The polynucleotide encoding the receptor protein of the invention may be any polynucleotide as long as it comprises a nucleotide sequence (DNA or RNA; preferably DNA) encoding the receptor protein of the invention. The polynucleotide may be a DNA or RNA (such as mRNA) encoding the receptor protein of the invention, and may be double-stranded or single-stranded. When the polynucleotide is double-stranded, it may be a double-stranded DNA, a double-stranded RNA, or a DNA:RNA hybrid. When the polynucleotide is single-stranded, it may be a sense strand (i.e. coding strand) or an anti-sense strand (i.e. non-coding strand).

With the polynucleotide encoding the receptor protein of the invention, it is possible to quantitatively determine the mRNA of the receptor protein of the invention by such methods as described in New PCR and Its Application (Extra Issue of Experimental Medicine), 15 (7), 1997 or modifications thereof.

The DNA encoding the receptor protein of the invention may be any of the following DNAs: genomic DNA, genomic DNA library, cDNA derived from the above-mentioned cells or tissues, cDNA library derived from the above-mentioned cells or tissues, or synthetic DNA. Vectors used for library construction may be any vectors such as bacteriophage, plasmid, cosmid, phagemid, and so on. Alternatively, total RNA or mRNA fraction may be prepared from the above-mentioned cells or tissues, followed by direct amplification by reverse transcriptase polymerase chain reaction (hereinafter, abbreviated to "RT-PCR").

Specific examples of the DNA encoding the receptor protein of the invention include a DNA comprising the nucleotide sequence represented by SEQ ID NO: 38, SEQ ID NO: 55 or SEQ ID NO: 56; or a DNA which comprises a nucleotide sequence hybridizable to the nucleotide sequence represented by SEQ ID NO: 38, SEQ ID NO: 55 or SEQ ID NO: 56 under highly stringent conditions and encodes a receptor protein having substantially the same activity in nature (e.g. ligand-binding activity, signal transducing effect, and so forth) as the activity of the receptor protein of the invention.

As the DNA hybridizable to the nucleotide sequence represented by SEQ ID NO: 38, SEQ ID NO: 55 or SEQ ID NO: 56 under highly stringent conditions, a DNA which comprises a nucleotide sequence having about 70% or more, preferably about 80% or more, still more preferably about 90% or more, most preferably about 95% or more homology to the nucleotide sequence represented by SEQ ID NO: 38, SEQ ID NO: 55 or SEQ ID NO: 56 may be used, for example.

The hybridization can be carried out, for example, according to the method described in "Molecular Cloning", 2nd Edition (J. Sambrook et al., Cold Spring Harbor Lab. Press, 1989). When commercial libraries are used, the hybridization can be carried out according to the instructions attached thereto. Preferably, the hybridization can be carried out under highly stringent conditions.

"Highly stringent conditions" refers to, for example, conditions where sodium concentration is about 19–40 mM, preferably about 19–20 mM, and temperature is about 50–70° C., preferably about 60–65° C. In particular, conditions where sodium concentration is about 19 mM and temperature is about 65° C. are most preferable.

The polypeptide encoded by the DNA hybridizable to the nucleotide sequence represented by SEQ ID NO: 38, SEQ ID NO: 55 or SEQ ID NO: 56 may be prepared in accordance with the above-described procedures for the production of the polypeptide of the invention. Amides, esters and salts of this polypeptide may be the same as the amides, esters and salts of the polypeptide of the invention.

More specifically, as the DNA encoding the receptor protein consisting of the amino acid sequence represented by SEQ ID NO: 37, a DNA consisting of the nucleotide sequence represented by SEQ ID NO: 38 may be used, for example. As DNA encoding the receptor protein consisting of the amino acid sequence represented by SEQ ID NO: 54, a DNA consisting of the nucleotide sequence represented by SEQ ID NO: 55 or SEQ ID NO: 56 may be used, for example.

The expression "polynucleotide comprising a part of the nucleotide sequence of a DNA encoding the receptor protein of the invention or a part of the nucleotide sequence complementary to the DNA" is intended to include not only the DNA encoding the partial peptide of the invention but also RNA encoding the same.

The DNA encoding the partial peptide of the receptor protein of the invention may be any DNA as long as it comprises a nucleotide sequence described above encoding the partial peptide of the invention. Further, the DNA may be any of the following DNAs: genomic DNA, genomic DNA library, cDNA derived from the above-mentioned cells or tissues, cDNA library derived from the above-mentioned cells or tissues, or synthetic DNA. Vectors used for library construction may be any vectors such as bacteriophage, plasmid, cosmid, phagemid, and so on. Alternatively, mRNA fraction may be prepared from the above-mentioned cells or tissues, followed by direct amplification by reverse transcriptase polymerase chain reaction (hereinafter, abbreviated to "RT-PCR").

Specific examples of the DNA encoding the partial peptide of the invention include, but are not limited to, (1) a DNA comprising a part of the nucleotide sequence of a DNA comprising the nucleotide sequence represented by SEQ ID NO: 38, SEQ ID NO: 55 or SEQ ID NO: 56 or (2) a DNA comprising a part of the nucleotide sequence of a DNA which comprises a nucleotide sequence hybridizable to the nucleotide sequence represented by SEQ ID NO: 38, SEQ ID NO: 55 or SEQ ID NO: 56 under highly stringent conditions and encodes a receptor protein having substantially the same activity in nature (e.g. ligand-binding activity, signal transducing effect and so forth) as the activity of the receptor protein of the invention.

The antibody against the invention to RFRP-3 (hereinafter, sometimes briefly referred to as the "antibody of the invention") may be either a polyclonal antibody or monoclonal antibody as long as it is capable of recognizing the antibody of the invention against RFRP-3.

The antibody of the invention against RFRP-3 can be prepared in accordance with known procedures for preparing antibodies or antisera using the RFRP-3 of the invention as an antigen.

[Preparation of Monoclonal Antibodies]

(a) Preparation of Monoclonal Antibody-Producing Cells

The RFRP-3 of the invention is administered to warm-blooded animals either alone or together with a carrier or diluent to a site capable of producing antibodies upon the administration. In order to enhance the ability to produce antibodies, complete Freund's adjuvants or incomplete Freund's adjuvants may also be administered. The administration is usually carried out once in every two to six weeks and two to ten times in the total. Examples of warm-blooded animals useful in the invention include monkey, rabbit, dog, guinea pig, mouse, rat, sheep, goat and chicken. Among them, mouse or rat is used preferably.

In the preparation of monoclonal antibody-producing cells, individuals with detectable antibody titers are selected from warm-blooded animals (e.g. mice) immunized with antigen. Then, the spleen or lymph nodes are collected from them two to five days after the final immunization, and antibody-producing cells contained therein are fused with myeloma cells of a homologous or heterologous animal to thereby obtain monoclonal antibody-producing hybridomas. Measurement of antibody titers in antisera may be carried out, for example, by reacting a labeled polypeptide (which will be described later) with the antiserum, followed by measuring the activity of the labeling agent bound to the antibody. The cell fusion may be carried out by a known method, for example, the method of Koehler and Milstein (Nature, 256, 495, (1975)). Examples of useful fusion promoters include polyethylene glycol (PEG), Sendai virus and so forth. Preferably, PEG is used.

Examples of myeloma cells useful in the invention include myeloma cells of warm-blooded animals such as NS-1, P3U1, SP2/0, AP-1 and so forth. Preferably, P3U1 is used. A preferable ratio of the number of antibody-producing cells used (spleen cells) to the number of myeloma cells is from about 1:1 to about 20:1. When PEG (preferably PEG 1000 to PEG 6000) is added at a concentration of about 10–80% and the resultant cell mixture is incubated at 20–40° C. (preferably, at 30–37° C.) for about 1–10 minutes, an efficient cell fusion can be achieved.

Various methods may be used for screening for monoclonal antibody-producing hybridomas. For example, hybridoma culture supernatant is added to a solid phase (e.g. microplate) on which the RFRP-3 antigen has been adsorbed either directly or with a carrier. Then, a radioactively or enzymatically labeled anti-immunoglobulin antibody (anti-mouse immunoglobulin antibody is used when mouse cells are used in the cell fusion) or protein A is added thereto to detect monoclonal antibodies bound to the solid phase. Alternatively, a method may be used in which hybridoma culture supernatant is added to a solid phase on which an anti-immunoglobulin antibody or protein A has been absorbed; then, a radioactively or enzymatically labeled polypeptide is added thereto to thereby detect monoclonal antibodies bound to the solid phase.

Selection of monoclonal antibodies may be carried out by known methods or methods based on them. Usually, selection can be carried out in a medium for culturing animal cells supplemented with HAT (hypoxanthine, aminopterin and thymidine). As a medium for selection and culturing, any medium may be used as long as hybridomas are capable of growing therein. Examples of useful media include RPMI 1640 medium containing about 1–20% (preferably about 10–20%) of fetal calf serum, GIT medium (Wako Pure Chemical Industries, Ltd.) containing about 1–20% of fetal calf serum and a serum-free medium for hybridoma cultivation (SFM-101; Nissui Pharmaceutical Co.). The cultivation temperature is usually about 20–40° C., preferably about 37° C. The cultivation period is usually from five days to three weeks, preferably one to two weeks. The cultivation may be carried out usually under 5% carbon dioxide. The antibody titer of hybridoma culture supernatant may be measured in the same manner as in the above-mentioned measurement of the antibody titers in antisera.

(b) Purification of the Monoclonal Antibodies

Separation and purification of monoclonal antibodies may be carried out by conventional methods, such as methods for separating/purifying immunoglobulin [e.g. salting-out, alcohol precipitation, isoelectric precipitation, electrophoresis, adsorption/desorption using ion exchangers (e.g. DEAE), ultracentrifugation, gel filtration, specific purification methods in which only an antibody is collected by means of an antigen-binding solid phase or active adsorbent such as protein A or protein G, followed by dissociation of the bond].

[Preparation of Polyclonal Antibodies]

The polyclonal antibody of the invention can be produced by known methods or methods based on them. For example, an immunogen (RFRP-3 antigen) per se or a complex of the immunogen and a carrier protein is prepared. Then, using the immunogen or the complex, warm-blooded animals are immunized in the same manner as described for the production of monoclonal antibodies. Fractions containing the antibody against the polypeptide of the invention are harvested from the immunized animals, followed by separation and purification of the antibody.

With respect to the immunogen-carrier protein conjugate for use in the immunization of warm-blooded animals, the kind of carrier protein and the mixing ratio of the carrier and the hapten are not particularly restricted as long as antibodies are produced efficiently against the hapten cross-linked to the carrier. For example, bovine serum albumin, bovine thyroglobulin, hemocyanin, or the like is coupled to the hapten at a weight ratio of about 0.1–20:1, preferably about 1–5:1.

A variety of condensing agents can be used for the coupling between the hapten and the carrier. For example, glutaraldehyde, carbodiimide, maleimide, or active ester reagents containing a thiol or dithiopyridyl group may be used.

The condensation product is administered to a warm-blooded animal either alone or together with a carrier or diluent at a site capable of producing antibodies upon the administration. In order to enhance the antibody production ability, complete Freund's adjuvant or incomplete Freund's adjuvant may also be administered. Administration is carried out generally once in about every 2–6 weeks and about 3–10 times in the total.

Polyclonal antibodies can be recovered from the blood, abdominal dropsy or other body fluid, preferably from the blood, of the warm-blooded animal immunized as described above.

Polyclonal antibody titers in antisera can be determined in the same manner as described above for the determination of monoclonal antibody titers in antisera. The separation and purification of polyclonal antibodies can be carried by the same methods for separation and purification of immunoglobulin as those described for the separation and purification of monoclonal antibodies.

With respect to the antisense DNA having a nucleotide sequence complementary to or substantially complementary to the DNA encoding the RFRP-3 of the invention (hereinafter, this DNA may be referred to as the "DNA of the invention"), any antisense DNA may be used as long as it has a nucleotide sequence complementary to or substantially complementary to the DNA of the invention and has an effect capable of inhibiting the expression of this DNA.

A nucleotide sequence substantially complementary to the DNA of the invention refers to, for example, a nucleotide sequence having about 70% or more, preferably about 80% or more, more preferably about 90% or more, most preferably about 95% or more homology to the full-length or a partial nucleotide sequence of the complementary nucleotide sequence to the DNA of the invention (i.e., the complementary strand to the DNA of the invention). Particularly preferable is an antisense DNA having about 70% or more, preferably about 80% or more, more preferably about 90% or more, most preferably about 95% or more homology to a part of the complementary strand to the DNA of the invention encoding an N-terminal region of the RFRP-3 of the invention (e.g. nucleotide sequence encoding a region neighboring the initiation codon). These antisense DNAs can be synthesized with known DNA synthesizers.

(1) Therapeutic and/or Prophylactic Agents for Various Diseases Where the RFRP-3 of the Invention is Involved The RFRP-3 of the invention, or amides or esters thereof, or salts thereof (hereinafter, sometimes these may be briefly referred to as the "RFRP-3 of the invention") have an effect in regulating prolactin secretion, i.e. promoting and inhibiting effects on prolactin secretion. Since the RFRP-3 of the invention has an effect in promoting prolactin secretion, the RFRP-3 may be used as a medicine, for example, as a prophylactic and/or therapeutic agent for various diseases associated with prolactin secretion failure.

On the other hand, since the RFRP-3 of the invention has high affinity with the receptor protein of the invention, desensitization against prolactin secretion will occur when administered at a high dose. As a result, the RFRP-3 of the invention also has an effect in inhibiting prolactin secretion. In such a case, the RFRp-3 can be used as a prophylactic and/or therapeutic agent for various diseases associated with excessive prolactin secretion.

Therefore, as an agent for promoting prolactin secretion, the RFRP-3 of the invention is useful as a prophylactic and/or therapeutic agent for various diseases associated with prolactin secretion, such as hypoovarianism, seminal vesicle hypoplasia, osteoporosis, menopausal syndrome, hypogalactia, hypothyroidism or renal insufficiency.

Further, since the RFRP-3 of the invention has aphrodisiac effect (pheromone-like effect) based on its effect in promoting prolactin secretion, it is also useful as an aphrodisiac agent.

Further, as an inhibitor of prolactin secretion, the RFRP-3 of the invention is useful as a prophylactic and/or therapeutic agent for various diseases associated with prolactin secretion, such as hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma, Sheehan's syndrome or spermatogenic disorder.

Further, the RFRP-3 of the invention is also useful as a contraceptive based on its prolactin secretion-inhibiting effect.

Besides, the RFRP-3 of the invention is also useful as a medicine for testing prolactin secretion function or a veterinary medicine such as a promoting agent for milk secretion in mammals such as bovine, goat, pig and so forth. Further, it is expected to apply the RFRP-3 to a useful substance production system where the useful substance is allowed to be produced in mammal bodies and then secreted into their milk.

Further, since the RFRP-3 of the invention has placental function-regulating effect, the RFRP-3 is also useful as a prophylactic and/or therapeutic agent for choriocarcinoma, hydatidiform mole, invasive mole, miscarriage, fetal hypotrophy, glucose metabolism disorder, lipidosis or induction of delivery.

The effect of regulating prolactin secretion of the RFRP-3 of the invention may be measured by methods described, for example, in Neuroendocrinology, vol. 62, 1995, pp. 198–206 or Neuroscience Letters, vol. 203, 1996, pp. 164–170, or modifications thereof. Preferably, the measurement is carried out by the methods described later in Examples.

Further, since the RFRP-3 of the invention has pain-inducing effect, the RFRP-3 is also useful as a prophylactic and/or therapeutic agent for paralgesia.

When the RFRP-3 of the invention is used as the above-described medicine or veterinary medicine, the RFRP-3 may be used according to conventional procedures. For example, the RFRP-3 of the invention may be administered orally in the form of tablets (sugar-coated, if necessary), capsules, elixirs, microcapsules or the like; or parenterally in the form of injections such as aseptic solutions or suspensions in water or other pharmaceutically acceptable liquids. These preparations may be produced, for example, by mixing the RFRP-3 of the invention or a salt thereof with physiologically acceptable carriers, flavoring agents, excipients, vehicles, antiseptics, stabilizers, binders and so forth in unit dosage forms required for preparing generally approved pharmaceutical preparations. The amounts of active ingredients in these formulations are decided so that an appropriate dose within the specified range can be obtained.

Examples of additives which may be mixed in tablets, capsules and so forth include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is capsule, liquid carrier such as oils and fats may further be included in addition to the above-mentioned materials. Sterile compositions for injection can be formulated according to conventional practices in pharmaceutical manufacturing, e.g., by dissolving or suspending active ingredients, naturally occurring vegetable oils such as sesame oil, coconut oil, and so forth in vehicles such as water for injection.

Examples of aqueous liquids for injection include physiological saline and isotonic solutions containing glucose and other auxiliary agents (e.g. D-sorbitol, D-mannitol, sodium chloride, and so forth). They may be used in combination with a suitable auxiliary solubilizer such as alcohol (e.g. ethanol and so forth), polyalcohol (e.g. propylene glycol, polyethylene glycol, and so forth), nonionic surfactant (e.g. Polysorbate 80™, HCO-50, and so forth). Examples of oily liquids for injection include sesame oil, soybean oil, and so forth. They may be used in combination with an auxiliary solubilizer such as benzyl benzoate, benzyl alcohol, and so forth. In addition, buffers (e.g. phosphate buffer, sodium acetate buffer, and so forth), analgesic agents (e.g. benzalkonium chloride, procaine hydrochloride, and so forth), stabilizers (e.g. human serum albumin, polyethylene glycol, and so forth), preservatives (e.g. benzyl alcohol, phenol, and so forth), antioxidants, and so forth may also be admixed therewith. Usually, the prepared injections are filled in appropriate ampoules aseptically.

Since the thus obtained preparations are safe and of low toxicity, they can be administered to mammals (e.g., human, rat, mouse, guinea pig, rabbit, sheep, pig, bovine, horse, cat, dog, monkey, sacred baboon, chimpanzee, and so forth).

Although dose levels of the RFRP-3 of the invention may vary depending on symptoms and so on, the RFRP-3 of the invention is generally administered to adult patients with hypothyroidism (60 kg in body weight) at a dose of about 0.1–100 mg/day, preferably about 1.0–50 mg/day, more preferably about 1.0–20 mg/day when administered orally. With respect to parenteral administration, if the RFRP-3 of the invention is administered, for example, in the form of an injection, it is convenient to intravenously inject the RFRP-3 into adult patients with hypothyroidism (60 kg in body weight) at a dose of about 0.01–30 mg/day, preferably about 0.1–20 mg/day, and more preferably about 0.1–10 mg/day, though the dose per administration may vary depending on the patient to be treated, symptoms, method of administration, and so forth. For other animals, corresponding doses may be administered after appropriate conversion of the above-mentioned values per 60 kg.

(2) Method of Screening for Compounds or Salts Thereof that Promote or Inhibit the Activity of the RFRP-3 of the Invention A method of screening for compounds or salts thereof that promote or inhibit the activity of the RFRP-3 of the invention comprising using the RFRP-3 of the invention is preferably a method of screening for compounds or salts thereof that promote or inhibit the activity of the RFRP-3 of the invention comprising using the RFRP-3 of the invention and the receptor protein of the invention or a partial peptide, amide, ester or salt thereof (hereinafter, they are sometimes referred to as the "receptor protein of the invention").

Specifically, this screening method is performed by measuring the activities of the RFRP-3 of the invention in case (i) where the receptor protein of the invention is contacted with the RFRP-3 of the invention and in case (ii) where the receptor protein of the invention and a test compound are contacted with the RFRP-3 of the invention, and then comparing the results.

Specifically, the above screening method is characterized by measuring and comparing, for example, the cell stimulatory activities of the RFRP-3 of the invention and the test compound or the amounts of binding of the RFRP-3 of the invention and the test compound to the receptor protein of the invention in case (i) and case (ii).

The cell stimulatory activity and so forth of the RFRP-3 of the invention may be measured by known methods such as those described in Dockray, G. J. et al., Nature, 305: 328–330, 1983; Fukusumi, S., et al., Biochem. Biophys. Res. Commun., 232: 157–163, 1997; Hinuma, S., et al., Nature, 393: 272–276, 1998; Tatemoto, K., et al. Biochem. Biophys. Res. Commun., 251: 471–476, 1998, or modifications thereof.

The amounts of binding of the RFRP-3 of the invention and the test compound to the receptor protein of the invention and the cell stimulatory activities thereof may be measured by the methods described later or modifications thereof.

The test compound may be, for example, a peptide, protein, non-peptidic compound, synthetic compound, fermentation product, cell extract, plant extract, or animal tissue extract. These compounds may be either novel compounds or known compounds.

For carrying out the above screening method, the RFRP-3 of the invention is suspended in a buffer appropriate for screening to thereby prepare a sample of the RFRP-3 of the invention. Any buffer may be used as long as it does not inhibit the reaction between the RFRP-3 of the invention and the receptor protein of the invention; e.g. phosphate buffer, Tris-HCl buffer and so forth of pH about 4–10 (preferably about 6–8) may be used.

For example, a test compound which promotes the cell death inhibitory activity (e.g. survival ratio) in (ii) above by about 20% or more, preferably by about 30% or more, more preferably by about 50% or more compared to the activity in (i) above may be selected as a compound, or a salt thereof, that promotes the activity of the polypeptide of the invention.

For example, a test compound which increases the cell stimulatory activity and so forth in (ii) by about 20% or more, preferably by about 30% or more, more preferably by about 50% or more compared to the corresponding activity in (i) above may be selected as a compound that promotes the cell stimulatory activity and so forth of the RFRP-3 of the invention. On the other hand, a test compound which inhibits the cell stimulatory activity and so forth in (ii) by about 20% or more, preferably by about 30% or more, more preferably by about 50% or more compared to the corresponding activity in (i) above may be selected as a compound that inhibits the cell stimulatory activity and so forth of the RFRP-3 of the invention.

Prior to these tests, it is preferable to confirm that test compounds bind to the receptor protein of the invention by testing the compounds in accordance with the procedures (i) to (iii), or modifications thereof, described in later in "Measurement of the Amounts of Binding of the RFRP-3 of the Invention and Test Compounds to the Receptor Protein of the Invention".

Further, as an indicator for judging that the above-described test compound is a compound or a salt thereof that promotes or inhibits the activity of the RFRP-3 of the invention, there are amounts of binding between RFRP-3 of the present invention or the experimental compound and the receptor protein of the present invention and an activity that inhibits the binding of the labeled RFRP-3 of the invention to the receptor protein of the invention. For example, a test compound that inhibits the binding of the labeled RFRP-3 by 10% or more at $1\times10^{-2}$ M or below in such a binding test system as described in Hosoya M. et al., Biochem. Biophys. Res. Commun. 194(1), 133–143, 1993 is considered very likely to be a compound or a salt thereof that promotes or inhibits the activity of RFRP-3 of the invention. However, binding inhibitory activity is a relative value measured based on the binding of the labeled RFRP-3. Therefore, binding inhibitory activity is not an essential item for judging that the relevant test compound is a compound or a salt thereof that promotes or inhibits the activity of RFRP-3 of the invention.

The screening kit of the invention contains the RFRP-3 of the invention. Preferably, the screening kit of the invention further contains the receptor of the RFRP-3 of the invention, i.e. the receptor protein of the invention (specifically, a protein comprising an amino acid sequence identical or substantially identical to the amino acid sequence represented by SEQ ID NO: 37 or a salt thereof, or a partial peptide of the protein, or an amide, ester or salt of the partial peptide).

As one example of the screening kit of the invention, the following may be given.

1. Screening Reagents (i) Measuring Buffer and Washing Buffer

Hanks' Balanced Salt Solution (Gibco) supplemented with 0.05% bovine serum albumin (Sigma).

This buffer may be stored at 4° C. after sterilization with a filter 0.45 µm in pore size or may be prepared at the time of use.

(ii) Receptor Sample

CHO cells expressing the receptor protein of the invention are sub-cultured to 12-well plates at $5\times10^5$ cells/well and then cultured for 2 days at 37° C., under 5% $CO_2$ 95% air.

(iii) Labeled Ligand

An aqueous solution of the RFRP-3 of the invention labeled with a commercial radioisotope such as [$^3$H], [$^{125}$I], [$^{14}$C] or [$^{35}$S] is stored at 4° C. or −20° C. This solution is diluted to 1 µM with the measuring buffer at the time of use.

(iv) Ligand Standard Solution

The RFRp-3 of the invention is dissolved in 0.1% bovine serum albumin (Sigma)-containing PBS to give a concentration of 1 mM and stored at −20° C.

2. Measuring Method (i) The CHO cells expressing the receptor protein of the invention cultured in 12-well tissue culture plates are washed twice with 1 ml of the washing buffer. Then, 490 μl of the measuring buffer is added to each well.

(ii) After addition of 5 μl of a test compound ($10^{-3}$–$10^{-10}$ M), 5 μl of the labeled ligand is added and reacted for 1 hr at room temperature. In order to know the amount of non-specific binding, 5 μl of $10^{-3}$ M ligand is added instead of the test compound.

(iii) The reaction solution is removed, and the cells are washed three times with 1 ml of the washing buffer. The labeled ligand bound to the cells is dissolved with 0.2 N NaOH-1% SDS and mixed with 4 ml of Liquid Scintillator A (Wako Purechemical Industries).

(iii) The radioactivity is measured with a liquid scintillation counter (Beckman). Then, percent maximum binding (PMB) is determined with the numerical formula described below.

$$PMB = [(B-NSB)/(B_0-NSB)] \times 100 \quad \text{[Numerical Formula I]}$$

where
PMB: percent maximum binding
B: value when a test compound is added
NSB: amount of non-specific binding
$B_0$: amount of maximum binding The compounds or salts thereof obtainable by using the screening method or screening kit of the invention are compounds that are selected from the above-described test compounds (such as peptides, proteins, non-peptidic compounds, synthetic compounds, fermentation products, cell extracts, plant extracts, animal tissue extracts, plasma and so forth) and promote or inhibit the activity (e.g. cell stimulatory activity) of the RFRP-3 of the invention.

As salts of such compounds, the same salts as described earlier on the salts of the RFRP-3 of the invention may be used.

(3) Methods of Measuring the Amounts of Binding of the RFRP-3 of the Invention and Test Compounds to the Receptor Protein of the Invention and the Cell Stimulatory Activities Thereof By using the receptor protein of the invention or constructing an expression system for a recombinant receptor protein and using a receptor binding assay system with the expression system, it is possible to measure the amounts of binding and the cell stimulatory activities of those compounds (e.g. peptides, protein, non-peptidic compounds, synthetic compounds, fermentation products, and so forth) that bind to the receptor protein of the invention and have cell stimulatory activity (e.g. activity to promote or inhibit the liberation of arachidonic acid, the liberation of acetylcholine, intracellular $Ca^{2+}$ liberation, intracellular cAMP production, intracellular cGMP production, inositol phosphate production, changes in cell membrane potentials, the phosphorylation of intracellular proteins, the activation of c-fos, the lowering of pH, and so forth).

The measuring methods are characterized by measuring, for example, the amounts of binding of test compounds to the receptor protein of the invention or the cell stimulatory activities of the test compounds when the receptor protein of the invention is contacted with the RFRP-3 of the invention or the test compounds.

More specifically, the present invention provides the following measuring methods:

(i) a measuring method wherein a labeled RFRP-3 of the invention or a labeled test compound is contacted with the receptor protein of the invention, and then the amount of binding of the labeled RFRP-3 or the labeled test compound to the receptor protein is measured;

(ii) a measuring method wherein a labeled RFRP-3 of the invention or a labeled test compound is contacted with cells, or a membrane fraction thereof, containing the receptor protein of the invention, and then the amount of binding of the labeled RFRP-3 or the labeled test compound to those cells or the membrane fraction is measured;

(iii) a measuring method wherein a labeled RFRP-3 of the invention or a labeled test compound is contacted with a receptor protein expressed on cell membranes which has been prepared by culturing a transformant comprising a DNA encoding the receptor protein of the invention, and then the amount of binding of the labeled RFRP-3 or the labeled test compound to the receptor protein is measured;

(iv) a measuring method wherein a labeled RFRP-3 of the invention or a labeled test compound is contacted with cells containing the receptor protein of the invention, and then the cell stimulatory activities mediated by the receptor protein (e.g. activity to promote or inhibit the liberation of arachidonic acid, the liberation of acetylcholine, intracellular $Ca^{2+}$ liberation, intracellular cAMP production, intracellular cGMP production, inositol phosphate production, changes in cell membrane potentials, the phosphorylation of intracellular proteins, the activation of c-fos, the lowering of pH and so forth) are measured; and (v) a measuring method wherein a labeled RFRP-3 of the invention or a labeled test compound is contacted with a receptor protein expressed on cell membranes which has been prepared by culturing a transformant comprising a DNA encoding the receptor protein of the invention, and then the cell stimulatory activities mediated by the receptor protein (e.g. activity to promote or inhibit the liberation of arachidonic acid, the liberation of acetylcholine, intracellular $Ca^{2+}$ liberation, intracellular cAMP production, intracellular cGMP production, inositol phosphate production, changes in cell membrane potentials, the phosphorylation of intracellular proteins, the activation of c-fos, the lowering of pH and so forth) are measured.

It is especially preferable to conduct the tests described in (i) to (iii) above to confirm that the test compound binds to the receptor protein of the invention, and then to conduct the tests described in (iv) and (v) above.

First, the receptor protein used in the measuring method may be any material as long as it contains the aforementioned receptor protein of the invention. A suitable example is a receptor protein expressed in a large quantity in animal cells.

For the production of the receptor protein of the invention, the afore-mentioned expression method may be used. Preferably, the receptor protein is produced by expressing a DNA encoding the receptor protein in mammalian cells or in insect cells. As a DNA fragment encoding the desired protein portion, usually a complementary DNA is used though the DNA is not limited to a complementary DNA. For example, a gene fragment or synthetic DNA may also be used. In order to introduce the DNA fragment encoding the receptor protein of the invention into a host animal cell and to express it efficiently, it is preferred that the DNA fragment should be incorporated downstream of a promoter such as polyhedron promoter derived from nuclear polyhedrosis virus belonging to baculovirus, promoter derived from SV40, promoter derived from retrovirus, metallothionein promoter, human heat shock promoter, cytomegalovirus promoter, SR α promoter and so forth. The quantity and the quality of the expressed receptor can be examined by known methods. For example, methods described in Nambi, P. et al:

The Journal of Biochemical Society, vol. 267, pp. 19555–19559 (1992) may be used.

Thus, in the above measuring method, the material containing the receptor protein of the invention may be either the receptor protein of the invention purified according to known methods, or cells or a membrane fraction thereof containing the receptor protein.

When cells containing the receptor protein of the invention are used in the measuring method, the cells may be fixed in glutaraldehyde, formalin and so forth. Such fixation may be carried out according to known methods.

"Cells containing the receptor protein of the invention" refers to host cells expressing the receptor protein of the invention. Examples of the host cell useful in the invention include *Escherichia coli, Bacillus subtilis*, yeasts, insect cells and animal cells.

The "cell membrane fraction" refers to a cell membrane-rich fraction which is obtainable by known methods after disruption of cells. Examples of methods of cell disruption include a method of squeezing cells using a Potter-Elvehjem homogenizer, disruption by a Waring blender or a Polytron (Kinematica), disruption by ultrasonication, disruption via ejection of cells from small nozzles while applying a pressure using a French press or the like and so forth. For the fractionation of cell membranes, centrifugal fractionation such as differential centrifugation or density gradient centrifugation is mainly used. For example, disrupted cells are centrifuged at a low speed (500 rpm to 3,000 rpm) for a short period (usually, from about one to ten min); the resultant supernatant is further centrifuged at a high speed (15,000 rpm to 30,000 rpm) usually for 30 min to 2 hr; and the resulting precipitate is used as a membrane fraction. The membrane fraction contains large quantities of the expressed receptor protein and cell-derived membrane components such as phospholipids and membrane proteins.

The amount of the receptor protein in the receptor protein-containing cells or the membrane fraction thereof is preferably $10^3$ to $10^8$ molecules per cell, more preferably $10^5$ to $10^7$ molecules per cell. Incidentally, the greater the expressed amount, the higher the ligand binding activity (specific activity) per membrane fraction whereby the construction of a highly sensitive screening system becomes possible and, moreover, it permits measurement of a large amount of samples with the one same lot.

For conducting the above-mentioned methods (i) to (iii), an appropriate receptor protein fraction and a labeled test compound are necessary.

As the receptor protein fraction, a natural receptor protein fraction or a recombinant protein fraction having an activity equivalent to that of the natural protein fraction is preferable. The term "activity equivalent to" refers to equivalent ligand binding activity, signal transducing effect, or the like.

As the labeled test compound, a compound selected from peptides, proteins, non-peptidic compounds, synthetic compounds, fermentation products, cell extracts, plant extracts, animal tissue extracts, plasma, and so forth and labeled with [$^3$H], [$^{125}$I], [$^{14}$C], [$^{35}$S] and so forth.

Specifically, first, cells or cell membrane fractions containing the receptor protein of the invention are suspended in a buffer suitable for the assay to thereby prepare the receptor sample. The buffer may be any buffer, such as Tris-HCL buffer or phosphate buffer with pH 4–10 (preferably pH 6–8), as long as it does not inhibit the binding of the ligand to the receptor protein. In order to reduce non-specific binding, surfactants such as CHAPS, Tween 80™ (Kao-Atlas), digitonin or deoxycholate and various proteins such as bovine serum albumin (BSA) or gelatin may be added to the buffer. Further, in order to inhibit the degradation of the receptor and the ligand by protease, a protease inhibitor such as PMSF, leupeptin, E-64 (Peptide Institute) or pepstatin may be added. A specific amount (5,000 cpm to 500,000 cpm) of a test compound labeled with [$^3$H], [$^{125}$I], [$^{14}$C], [$^{35}$S] or the like is allowed to co-exist in 0.01 ml–10 ml of the receptor solution. In order to know the amount of non-specific binding (NSB), a reaction tube to which a greatly excessive amount of the unlabeled test compound has been added is also prepared. The reaction is carried out at 0–50° C., preferably at 4–37° C. for about 20 min to 24 hr, preferably about 30 min to 3 hr. After the reaction, the reaction solution is filtered through a glass fiber filter or the like, and washed with the appropriate amount of the same buffer. Then, the radioactivity remaining in the glass fiber filter is measured with a liquid scintillation counter or a gamma-counter. When the count (B-NSB) obtained by subtracting the non-specific binding amount (NSB) from the total binding amount (B) is more than 0 cpm, the test compound can be selected as a compound that promotes the activity of the RFRP-3 of the invention.

In order to conduct the methods described in (iv) and (v) above, the cell stimulatory activity mediated by the receptor protein (e.g. activity to promote or inhibit the liberation of arachidonic acid, the liberation of acetylcholine, intracellular $Ca^{2+}$ liberation, intracellular cAMP production, intracellular cGMP production, inositol phosphate production, changes in cell membrane potentials, the phosphorylation of intracellular proteins, the activation of c-fos, the lowering of pH, and so forth.) may be measured by known methods or with commercial measuring kits. Specifically, first, cells containing the receptor protein are cultured in multi-well plates or the like. The medium is exchanged with a fresh medium or an appropriate buffer without cytotoxicity. Then, the RFRP-3 of the invention or a test compound is added to the cells, which are incubated for a specific period. After extraction of the cells or recovery of the supernatant, the resultant products are determined quantitatively according to respective procedures. When it is difficult to assay the production of a substance to be used as an indicator of cell stimulatory activity (e.g. arachidonic acid) due to a protease contained in the cells, the assay may be performed with the addition of an inhibitor to the protease. With respect to such activity as inhibition of cAMP production, the activity may be detected as a production inhibitory effect upon those cells which were treated with forskolin or the like to increase their basic yield.

The measuring kit described above contains the receptor protein of the invention, cells containing the receptor protein of the invention, or a cell membrane fraction of cells containing the receptor protein of the invention.

As one example of such a measuring kit, the following may be given.

1. Screening Reagents (i) Measuring Buffer and Washing Buffer

Hanks' Balanced Salt Solution (Gibco) supplemented with 0.05% bovine serum albumin (Sigma).

This buffer may be stored at 4° C. after sterilization with a filter 0.45 μm in pore size or may be prepared at the time of use.

(ii) G Protein-Coupled Receptor Protein Sample

CHO cells expressing the receptor protein of the invention are sub-cultured to 12-well plates at $5 \times 10^5$ cells/well and then cultured for 2 days at 37° C. under 5% $CO_2$ 95% air.

(iii) Labeled Test Compound

A compound labeled with a commercial radioisotope such as [$^3$H], [$^{125}$I], [$^{14}$C] or [$^{35}$S], or a compound labeled with other appropriate method. An aqueous solution of the labeled test compound is stored at 4° C. or −20° C. and diluted to 1 μM with the measuring buffer at the time of use. Those test compounds which are sparingly soluble in water, they are dissolved in dimethyl formamide, DMSO, methanol, or the like.

(iv) Unlabeled Test Compound

The same compound used for the labeled test compound is prepared at a concentration 100- to 1000-fold higher than that of the labeled test compound.

2. Measuring Method
(i) The CHO cells expressing the receptor protein of the invention cultured in 12-well tissue culture plates are washed twice with 1 ml of the washing buffer. Then, 490 μl of the measuring buffer is added to each well.
(ii) Five μl of the labeled test compound is added to each well and reacted for 1 hr at room temperature. In order to know the amount of non-specific binding, 5 μl of the unlabeled test compound is added in advance.
(iii) The reaction solution is removed, and the cells are washed three times with 1 ml of the washing buffer. The labeled test compound bound to the cells is dissolved with 0.2 N NaOH-1% SDS and mixed with 4 ml of liquid Scintillator A (Wako Purechemical Industries).
(iii) The radioactivity is measured with a liquid scintillation counter (Beckman).

(4) Medicines Comprising the Compounds Obtained by the Screening Method of the Invention The compound or salts thereof obtained by using the screening method or the screening kit of the invention may be used as a prophylactic and therapeutic agent for various diseased associated with insufficient prolactin secretion when the compound has an effect of promoting prolactin secretion; and the compound or salts thereof may be used as a prophylactic and/or therapeutic agent for various diseases associated with excessive prolactin secretion when the compound has an effect of inhibiting prolactin secretion.

When the obtained compound or salts thereof have an effect of promoting prolactin secretion, they are useful as a prophylactic and/or therapeutic agent for various diseases associated with prolactin secretion, such as hypoovarianism, seminal vesicle hypoplasia, osteoporosis, menopausal syndrome, hypogalactia, hypothyroidism or renal insufficiency as an agent for promoting prolactin secretion.

Further, since the compound or salts thereof have aphrodisiac effect (pheromone-like effect) based on their effect in promoting prolactin secretion, they are also useful as an aphrodisiac agent.

On the other hand, when the obtained compound or salts thereof have an effect in inhibiting prolactin secretion, they may be used as a prophylactic and/or therapeutic agent for various diseases associated with excessive prolactin secretion. The compound or salts thereof are useful as a prophylactic and/or therapeutic agent for various diseases associated with prolactin secretion, such as hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma or Sheehan's syndrome or spermatogenic disorder, as an inhibitor of prolactin secretion.

Further, the compound or salts thereof are also useful as a contraceptive based on their effect in inhibiting prolactin secretion.

Besides, the obtained compound or salts thereof are also useful as a medicine for testing the function of prolactin secretion or veterinary medicine such as a promoting agent for milk secretion in mammals such as bovine, goat or pig. Further, it is expected to apply such compound or salts thereof to a production system for a useful substance where the useful substance is allowed to be produced in mammal bodies and then secreted into their milk.

Further, since the obtained compound or salts thereof have placental function-regulating effect, they are also useful as a prophylactic and/or therapeutic agent for choriocarcinoma, hydatidiform mole, invasive mole, miscarriage, fetal hypotrophy, glucose metabolism disorder, lipidosis or induction of delivery.

The effect in regulating prolactin secretion of the compound or salts thereof obtained by using the above-described screening method or screening kit may be measured by methods described, for example, in Neuroendocrinology, vol. 62, 1995, pp. 198–206 or Neuroscience Letters, vol. 203, 1996, pp. 164–170, or modifications thereof. Preferably, the measurement is carried out by the methods described later in Examples.

Further, compounds that promote the activity of the RFRP-3 of the invention are useful as a prophylactic and/or therapeutic agent for paralgesia.

On the other hands, compounds that inhibit the activity of the RFRP-3 of the invention are useful as an analgesic agent.

When the obtained compound or a salt thereof is used as the above-described medicine or veterinary medicine, they may be used according to conventional procedures. For example, the compounds or salts thereof may be administered orally in the form of tablets (sugar-coated, if necessary), capsules, elixirs, microcapsules or the like; or parenterally in the form of injections such as aseptic solutions or suspensions in water or other pharmaceutically acceptable liquids. These preparations may be produced, for example, by mixing the compound or a salt thereof with physiologically acceptable carriers, flavoring agents, excipients, vehicles, antiseptics, stabilizers, binders, and so forth in unit dosage forms required for preparing generally approved pharmaceutical preparations. The amounts of active ingredients in these formulations are decided so that an appropriate dose within the specified range can be obtained.

Examples of additives which may be mixed in tablets, capsules, and so forth include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is capsule, liquid carrier such as oils and fats may further be included in addition to the above-mentioned materials. Sterile compositions for injection can be formulated according to conventional practices in pharmaceutical manufacturing, e.g., by dissolving or suspending active ingredients, naturally occurring vegetable oils such as sesame oil, coconut oil, and so forth in vehicles such as water for injection.

Examples of aqueous liquids for injection include physiological saline and isotonic solutions containing glucose and other auxiliary agents (e.g. D-sorbitol, D-mannitol, sodium chloride, and so forth). They may be used in combination with a suitable auxiliary solubilizer such as alcohol (e.g.

ethanol, and so forth.), polyalcohol (e.g. propylene glycol, polyethylene glycol, and so forth), nonionic surfactant (e.g. Polysorbate 80™, HCO-50, and so forth). Examples of oily liquids for injection include sesame oil, soybean oil, and so forth. They may be used in combination with an auxiliary solubilizer such as benzyl benzoate, benzyl alcohol, and so forth. In addition, buffers (e.g. phosphate buffer, sodium acetate buffer, and so forth), analgesic agents (e.g. benzalkonium chloride, procaine hydrochloride, and so forth), stabilizers (e.g. human serum albumin, polyethylene glycol, and so forth), preservatives (e.g. benzyl alcohol, phenol, and so forth), antioxidants, and so forth may also be admixed therewith. Usually, the prepared injections are filled in appropriate ampoules aseptically.

Since the thus obtained preparations are safe and of low toxicity, they can be administered to mammals (e.g., human, rat, mouse, guinea pig, rabbit, sheep, pig, bovine, horse, cat, dog, monkey, sacred baboon, chimpanzee, and so forth).

Although dose levels of the obtained compound or a salt thereof may vary depending on symptoms and so on, the compound or a salt thereof is generally administered to adult patients with hypothyroidism (60 kg in body weight) at a dose of about 0.1–100 mg/day, preferably about 1.0–50 mg/day, more preferably about 1.0–20 mg/day when administered orally. With respect to parenteral administration, if the compound or a salt thereof is administered, for example, in the form of an injection, it is convenient to inject intravenously to adult patients with hypothyroidism (60 kg in body weight) at a dose of about 0.01–30 mg/day, preferably about 0.1–20 mg/day, and more preferably about 0.1–10 mg/day, though the dose per administration may vary depending on the patient to be treated, symptoms, method of administration, and so forth. For other animals, corresponding doses may be administered after appropriate conversion of the above-mentioned values per 60 kg.

(5) Quantitative Determination of RFRP-3 Using the Antibody of the Invention

Since the antibody of the invention can specifically recognize the RFRP-3 of the invention, the antibody may be used for quantitative determination of the RFRP-3 of the invention contained in sample solutions, in particular, in quantitative determination by sandwich immunoassay.

The present invention provides:

(i) a method of quantitative determination of the RFRP-3 of the invention in a sample solution, comprising competitively reacting the antibody of the invention with the sample solution and the RFRP-3 of the invention labeled, and determining the ratio of the labeled RFRP-3 of the invention bound to the antibody; and (ii) a method of quantitative determination of the RFRP-3 of the invention in a sample solution, comprising reacting the sample solution with the antibody of the invention insolubilized on a carrier and another antibody of the invention labeled, simultaneously or in succession, and determining the activity of the labeling agent on the insolubilized carrier.

In the quantitative determination method described in (ii) above, it is preferred that one antibody should be an antibody that recognizes an N-terminal region of the RFRP-3 of the invention and the other antibody should be an antibody that reacts with a C-terminal region of the RFRP-3 of the invention.

Further, the monoclonal antibody of the invention may be used to quantitatively determine the RFRP-3 of the invention or may be used for detection of the RFRP-3 by tissue staining. For these purposes, either antibody molecules per se or the F(ab')$_2$, Fab' or Fab fragment thereof may be used.

Methods of quantitative determination of the RFRP-3 of the invention using the antibody of the invention are not particularly limited. Any measuring method may be used in which the amount of antibody, antigen or antibody-antigen complex corresponding to the amount of the antigen in a sample solution (e.g. the amount of the RFRP-3 of the invention) is detected by chemical or physical means, and then calculated from a standard curve prepared using a standard solution containing a known amount of the antigen. For example, nephrometry, competitive methods, immunometric methods and sandwich assay may be used conveniently and, in terms of sensitivity and specificity, the sandwich assay described later is particularly preferred.

Examples of labeling agents useful in measuring methods utilizing labeling substances include radioisotopes, enzymes, fluorescent substances, and luminescent substances. Examples of radioisotopes include [$^{125}$I], [$^{131}$I], [$^{3}$H] and [$^{14}$C]. Preferred examples of enzymes are those which are stable and with high specific activity, e.g., β-galactosidase, β-glucosidase, alkali phosphatase, peroxidase and malate dehydrogenase. Examples of fluorescent substances include fluorescamine and fluorescein isothiocyanate. Examples of luminescent substances include luminol, luminol derivatives, luciferin, and lucigenin. Further, a biotin-avidin system may also be used for binding an antibody or antigen with a labeling agent.

Insolubilization of antigens or antibodies may be performed by physical adsorption or by chemical binding usually used for insolubilizing or immobilizing peptides or enzymes. Examples of carriers useful for this purpose include insoluble polysaccharides such as agarose, dextran and cellulose; synthetic resins such as polystyrene, polyacrylamide and silicone; and glass.

In the sandwich assay, a sample solution is reacted with an insolubilized monoclonal antibody of the invention (primary reaction); then, another monoclonal antibody of the invention that is labeled is reacted therewith (secondary reaction); and the activity of the labeling agent on the insolubilized carrier is measured to thereby quantitatively determine the amount of the RFRP-3 of the invention in the sample solution. The primary reaction and the secondary reaction may be conducted in the reverse order, or they may be conducted simultaneously or with an interval. The type of the labeling agent and the method of insolubilization may be the same as those described herein earlier. In immunoassays using the sandwich technique, the antibody insolubilized on a solid phase or the antibody labeled is not necessarily a single antibody, a mixture of two or more antibodies may be used for the purposes of enhancing the sensitivity of measurement, and so forth.

In the method of measuring the RFRP-3 of the invention by the sandwich assay of the invention, the monoclonal antibodies of the invention used in the primary and the secondary reactions are preferably those antibodies whose sites of binding to the RFRP-3 of the invention are different from each other. For example, if the antibody used in the secondary reaction recognizes a C-terminal region of the RFRP-3 of the invention, an antibody that recognizes a site other than the C-terminal region, e.g. an N-terminal region, is preferably used in the primary reaction.

The monoclonal antibody of the invention may be used in a measuring system other than the sandwich assay, such as competitive methods, immunometric methods and nephrometry.

In competitive methods, an antigen in a sample solution and a labeled antigen are reacted competitively with an antibody, then, unreacted labeled antigen (F) and labeled antigen bound to the antibody (B) are separated (i.e. B/F separation); and the amount of the label of B or F is measured to thereby quantitatively determine the amount of the antigen in the sample solution. With respect to this reaction method, there are a liquid phase method in which a soluble antibody is used, and the B/F separation is conducted with polyethylene glycol, and a second antibody to the above-mentioned antibody is used; and a solid phase method in which a solidified antibody is used as the first antibody or a soluble antibody is used as the first antibody while a solidified antibody is used as the second antibody.

In immunometric methods, an antigen in a sample solution and a solidified antigen are reacted competitively with a specific amount of a labeled antibody, followed by separation of the solid phase from the liquid phase; or an antigen in a sample solution is reacted with an excessive amount of a labeled antibody, and then a solidified antigen is added to bind unreacted labeled antibody to the solid phase, followed by separation of the solid phase from the liquid phase. Subsequently, the amount of label in one of the phases is measured to determine the amount of the antigen in the sample solution.

In nephrometry, the amount of insoluble precipitate generated as a result of antigen-antibody reaction in a gel or solution is measured. Even when the amount of the antigen in a sample solution is small and thus only a small amount of such precipitate is obtained, laser nephrometry utilizing the scattering of laser can be used conveniently.

In applying each of those immunological measuring methods to the measuring method of the present invention, no special conditions or operations are required. A measuring system for the polypeptide of the present invention may be constructed using the conventional conditions and operational procedures in the relevant measuring method while taking into account usual technical consideration of those skilled in the art. For details of these commonly used technical means, a variety of reviews, reference books, and so forth may be referred to.

For example, Hiroshi Irie (ed.): "Radioimmunoassay" (Kodansha, 1974); Hiroshi Irie (ed.): "Radioimmunoassay; Second Series" (Kodansha, 1979), Eiji Ishikawa et al. (ed.): "Enzyme Immunoassay" (Igaku Shoin, Japan, 1978); Eiji Ishikawa et al. (ed.): "Enzyme Immunoassay" (Second Edition) (Igaku Shoin, 1982); Eiji Ishikawa et al. (ed.): "Enzyme Immunoassay" (Third Edition) (Igaku Shoin, 1987); "Methods in Enzymology", Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (Academic Press) and the like may be referred to.

By using the antibody of the invention as described above, the RFRP-3 of the invention can be quantitatively determined with high sensitivity.

Further, when abnormality is detected in the concentration of the RFRP-3 of the invention in a subject by quantitatively determining the concentration of the RFRP-3 of the invention using the antibody of the invention, it is possible to diagnose that the subject has one of the following diseases associated with prolactin secretion, such as hypoovarianism, seminal vesicle hypoplasia, osteoporosis, menopausal syndrome, hypogalactia, hypothyroidism, renal insufficiency, hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma, Sheehan's syndrome or spermatogenic disorder, or paralgesia; or that the subject is very likely to develop such a disease in the future.

Further, the antibody of the invention may be used for detecting the RFRP-3 of the invention present in body fluids, tissues or other samples. The antibody of the invention may also be used in the preparation of antibody columns for use in the purification of the RFRP-3 of the invention; in the detection of the RFRP-3 of the invention in individual fractions generated in the course of purification; and in the analysis of the behavior of the RFRP-3 of the invention in test cells.

(6) Gene Diagnostics

The DNA of the invention can, when used as a probe for example, detect abnormalities in DNA or mRNA encoding the RFRP-3 of the invention (gene abnormalities) in human or other warm-blooded animals (e.g. rat, mouse, guinea pig, rabbit, bird, sheep, pig, bovine, horse, cat, dog, monkey, and so forth). Thus, the DNA of the invention is useful as a gene diagnostic for diagnosing, e.g., damage, mutations or reduced expression of the above DNA or mRNA, or increase or excessive expression of the above DNA or mRNA.

Gene diagnosis using the DNA of the invention may be performed by known methods such as Northern hybridization or PCR-SSCP method (Genomics, Vol. 5, 874879 (1989); Proceedings of the National Academy of Sciences of the USA, 86: 2766–2770 (1989)).

When abnormality in expression is detected by Northern hybridization, for example, it is possible to diagnose that the relevant subject is very likely to have one of the following diseases associated with prolactin secretion, such as hypoovarianism, seminal vesicle hypoplasia, osteoporosis, menopausal syndrome, hypogalactia, hypothyroidism, renal insufficiency, hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma, Sheehan's syndrome or spermatogenic disorder, or paralgesia; or that the subject is very likely to develop such a disease in the future.

(7) Medicines Comprising Antisense DNA

Antisense DNA that complementarily binds to the DNA of the invention and thus inhibits the expression of that DNA is useful as a prophylactic and/or therapeutic agent for the above-described various diseases associated with prolactin secretion or as an analgesic agent.

For example, when the antisense DNA is used, the antisense DNA alone or the antisense DNA inserted into an appropriate vector such as a retrovirus vector, adenovirus vector, adeno-associated virus vector, and so forth may be administered using conventional means. The antisense DNA may be administered as it is or after formulation with physiologically acceptable carriers such as adjuvants to promote uptake, by means of a gene gun or a catheter such as hydrogel catheter. Formulation may be performed in the same manner as the formulation of medicines comprising the RFRP-3 of the invention.

Dose levels of the antisense DNA of the invention may vary depending upon the patient to be treated, the target organ, symptoms, administration route, and so on. In oral administration, generally, the antisense DNA is administered to patients with sterility (60 kg in body weight) at a dose of about 0.1–100 mg/day, preferably about 1.0–50 mg/day, more preferably about 1.0–20 mg/day. In parenteral administration, when the antisense DNA of the invention is administered, for example, in the form of an injection, it is convenient to inject the antisense DNA of the invention intravenously to patients with hyperprolactinemia (60 kg in body weight) at a dose of about 0.01–30 mg/day, preferably about 0.1–20 mg/day, more preferably about 0.1–10 mg/day, though the dose level may vary depending on the patient to be treated, the target organ, symptoms, administration route, and so on. For other animals, corresponding doses may be administered after appropriate conversion of the above-mentioned values per 60 kg.

Further, the antisense DNA may be used as an oligonucleotide probe for diagnostic purposes to examine the presence or state of expression of the DNA of the invention in tissues or cells.

(8) Medicines Comprising the Antibody of the Invention

The antibody of the invention that has an effect of neutralizing the activity of the RFRP-3 of the invention is useful as a prophylactic and/or therapeutic agent for the above-described diseases associated with prolactin secretion or as an analgesic agent.

The above-mentioned prophylactic and/or therapeutic agents comprising the antibody of the invention may be administered orally or parenterally to human or other mammals (e.g. rat, rabbit, sheep, pig, bovine, cat, dog, monkey, and so forth) in the forms of liquid preparations without any processing or in appropriate forms of pharmaceutical compositions. Dose levels may vary depending upon the patient to be treated, the target disease, symptoms, administration route, and so on. However, it is convenient to inject the antibody of the invention intravenously at a dose of about 0.01–20 mg/kg body weight, preferably about 0.1–10 mg/kg body weight, more preferably about 0.1–5 mg/kg body weight per administration about one to five times a day, preferably about one to three times a day. In other parenteral administration and oral administration, similar dose levels may be used. If symptoms are particularly heavy, the dose may be increased accordingly.

The antibody of the invention may be administered alone or in the forms of appropriate pharmaceutical compositions. The pharmaceutical compositions for the above administration comprise the antibody or salt thereof, pharmacologically acceptable carriers, and diluents or excipients. Such compositions are provided in forms appropriate for oral or parenteral administration.

For example, compositions for oral administration include solid or liquid preparations such as tablets (including sugar-coated tablets and film-coated tablets), pills, granules, dispersants, capsules (including soft capsules), syrups, emulsions and suspensions. These compositions are prepared according to conventional methods and contain carriers, diluents or excipients conventionally used in the field of medicine manufacturing. For example, lactose, starch, sucrose, magnesium stearate and the like are used as carriers or excipients for tablets.

Compositions for parenteral administration include, for example, injections and suppositories. Injections include intravenous injections, subcutaneous injections, intradermal injections, muscle injections, instilment injections, and so forth. Such injections may be prepared by dissolving, suspending or emulsifying the above antibody or salt thereof in an aseptic, aqueous or oily liquid. Examples of aqueous liquids for injection include physiological saline and isotonic solutions containing glucose and other auxiliary agents. They may be used in combination with a suitable auxiliary solubilizer such as alcohol (e.g. ethanol), polyalcohol (e.g. propylene glycol, polyethylene glycol), nonionic surfactant [e.g. Polysorbate 80™, HCO-50 (polyoxyethylene (50 mol) adduct of hydrogenated castor oil)], and so forth). Examples of oily liquids for injection include sesame oil and soybean oil. They may be used in combination with an auxiliary solubilizer such as benzyl benzoate, benzyl alcohol, and so forth. Usually, the prepared injections are filled in appropriate ampoules. Suppositories for administration into rectum may be prepared by mixing the antibody or a salt thereof with a conventional suppository base.

It is convenient to formulate the above-described pharmaceutical compositions for oral or parenteral administration into unit dosage forms that would give an appropriate dose of the active ingredient. Examples of such unit dosage forms include tablets, pills, capsules, injections (ampoules), and suppositories. Usually, each unit of these dosage forms contains preferably about 5–500 mg of the above-described antibody. In particular, each unit contains preferably about 5–100 mg in injections, and each unit in other dosage forms contains preferably about 10–250 mg.

The above-described pharmaceutical compositions may contain other active ingredients as long as they do not produce undesirable interaction with the above-described antibody.

(9) DNA-Transferred Animals

The present invention further provides non-human mammals harboring a foreign DNA encoding the RFRP-3 of the invention (hereinafter referred to briefly as the "foreign DNA of the invention") or a mutant thereof (sometimes referred to briefly as the "foreign mutant DNA of the invention").

Thus, the present invention provides:

(1) A non-human mammal harboring the foreign DNA of the invention or a mutant DNA thereof:

(2) The non-human mammal according to (1) which is a rodent:

(3) The non-human mammal according to (2) wherein the rodent is mouse or rat; and (4) A recombinant vector containing the foreign DNA of the invention or a mutant DNA thereof and capable of expressing the DNA in a mammal.

The non-human mammal harboring the foreign DNA of the invention or a mutant DNA thereof (hereinafter referred to briefly as the "DNA-transferred animal of the invention") can be created by transferring the desired DNA to a germinal cell such as unfertilized egg cells, fertilized egg cells, or sperm cells or primordial cells thereof, preferably during the period of embryogenesis in the ontogenesis of the non-human mammal (more preferably, in the stage of a single cell or a fertilized egg cell and generally at the 8-cell stage or earlier), by the calcium phosphate method, electric pulse method, lipofection method, agglutination method, microinjection method, particle gun method, or DEAE-dextran method. It is also possible to transfer the foreign DNA of the invention of interest into somatic cells, organs in the living body, tissue cells, or the like by such DNA transfer methods to use the resultant cells or tissues in cell culture or tissue culture. Further, by fusing the resultant cells with the above-mentioned germinal cell by known cell fusion methods, it is also possible to create the DNA-transferred animal of the invention.

The non-human mammal useful in the invention includes bovine, pig, sheep, goat, rabbit, dog, cat, guinea pig, hamster, mouse, rat, and so on. From the viewpoint of construction of diseased animal models, rodents which have comparatively short ontogenesis and life cycles and can be easily bred, particularly mouse (e.g. pure strains such as C57BL/6, DBA2, and so forth and hybrid strains such as B6C3F$_1$, BDF$_1$, B6D2F$_1$, BALB/c, ICR, and so forth) or rat (e.g. Wistar, SD, and so forth), are preferred.

Examples of the "mammal" in the expression "a recombinant vector capable of expressing the DNA in a mammal" include human in addition to the above-mentioned non-human mammals.

The foreign DNA of the invention is not a DNA of the invention which is inherently possessed by the non-human mammal, but a DNA of the invention that has been once isolated/extracted from a mammal.

Examples of the mutant DNAs of the invention include not only the DNAs that have variations (e.g. mutations) in the nucleotide sequence of the original DNA of the invention as a result of, for example, addition or deletion of nucleotides or substitution with other nucleotides, but also abnormal DNAs.

The term "abnormal DNA" as used herein means any DNA that causes expression of an abnormal RFRP-3 of the invention. For example, a DNA that allows expression of an RFRP-3 that inhibits the function of the normal RFRP-3 of the invention may be used.

The foreign DNA of the invention may be derived from a mammal that is of the same species as that of the host animal or of different species. For transfer of the DNA of the invention to the host animal, it is generally advantageous to use a DNA construct in which the DNA is ligated downstream of a promoter capable of expressing the DNA in animal cells. For example, in transferring the human DNA of the invention, this human DNA of the invention may be ligated downstream of a promoter capable of directing expression of DNAs derived from various animals (e.g. rabbit, dog, cat, guinea pig, hamster, rat, mouse, and so forth) harboring the DNA of the invention having high homology to the human DNA to thereby prepare a DNA construct (e.g. vector), which can then be microinjected into fertilized egg cells of a host mammal such as fertilized mouse egg cells. Thus, a DNA-transferred mammal showing high expression of the DNA of the invention can be created.

Examples of the expression vector for the RFRP-3 of the invention include plasmids derived from *E. coli*, plasmids derived from *B. subtilis*, plasmids derived from yeast, λ phage and other bacteriophages, retroviruses such as Molony leukemia virus, and animal viruses such as vaccinia virus and vaculovirus. Preferable examples are *E. coli*-derived plasmids, *B. subtilis*-derived plasmids and yeast-derived plasmids.

Examples of promoters that regulate the expression of the DNA include (1) promoters for DNAs derived from viruses (e.g. simian virus, cytomegalovirus, Molony leukemia virus, JC virus, papilloma virus, poliovirus, and so forth), (2) promoters derived from mammals (e.g. human, rabbit, dog, cat, guinea pig, hamster, rat, mouse, and so forth), for example, promoters of albumin, insulin II, uroprakin II, elastase, erythropoietin, endothelin, muscle creatine kinase, glial fibrillary acidic protein, glutathione S-transferase, platelet-derived growth factor β, keratin K1, K10, and K14, collagen type I and type II, cyclic AMP-dependent polypeptide kinase βI subunit, dystrophin, tartaric acid-resistant alkaline phosphatase, atrial natriuretic factor, endothelial receptor tyrosine kinase (generally abbreviated to Tie2), sodium/potassium-dependent adenosinetriphosphatase (Na, K-ATPase), neurofilament light chain, metallothionein I and IIA, metalloproteinase I tissue inhibitor, MHC Class I antigen (H-2L), H-ras, renin, dopamine β-hydroxylase, thyroid peroxidase (TPO), polypeptide chain elongation factor 1α (EF-1α), β-actin, α- and β-myosin heavy chain, myosin light chains 1 and 2, myelin basic protein, thyroglobulin, Thy-1, immunoglobulin H chain variable region (VNP), serum amyloid P component, myoglobin, troponin C, smooth muscle α-actin, preproenkephalin A, vasopressin, and so on. Preferable are those promoters which can direct high expression of the DNA in the whole body, e.g. cytomegalovirus promoter, human polypeptide chain elongation factor 1α (EF-1α) promoter, and human and chicken β-actin promoters.

It is preferable that the vector has a sequence for terminating the transcription of the desired messenger RNA (generally called terminator) in the DNA-transferred mammal. For example, sequences derived from viruses or various mammals may be used. Preferably, SV40 terminator derived from simian virus or the like is used.

In addition, for enhancing the expression of the desired DNA further, it is possible, depending on the specific purpose, to ligate a splicing signal, an enhancer domain, a portion of an eucaryotic DNA intron, and so forth upstream of the 5'-end of the promoter region, between the promoter region and the translated region, or downstream of the 3'-end of the translated region.

The translated region for the normal RFRP-3 of the invention may be obtained as the entire genomic DNA or a part thereof from liver-, kidney-, thyroid cell- or fibroblast-derived DNA from human or other mammals (e.g. rabbit, dog, cat, guinea pig, hamster, rat, mouse, and so forth) or commercial genomic DNA libraries. Alternatively, the translated region may be obtained using, as a raw material, cDNA prepared from liver-, kidney-, thyroid cell- or fibroblast-derived DNA by conventional methods. The foreign abnormal DNA is capable of creating a mutated translated region from the translated region for the normal RFRP-3 obtained from the above-mentioned cell or tissue by point mutagenesis.

The translated region can be prepared as a DNA construct which can be expressed in a DNA-transferred animal, by conventional recombinant DNA techniques, i.e. by ligating it downstream of the promoter and, if desired, upstream of the transcription termination site.

The transfer of the foreign DNA of the invention at the fertilized egg cell stage insures that the DNA will be ubiquitous in all the germ cells and somatic cells of the host mammal. The presence of the DNA of the invention in the germ cells of the DNA-transferred animal following DNA transfer means that all the germinal cells and somatic cells of all the subsequent generations of the DNA-transferred animal harbor the DNA of the invention. Thus, the progeny of such DNA-transferred animal which inherited the foreign DNA of the invention have the DNA in all of their germ cells and somatic cells.

The non-human mammal into which the foreign normal DNA of the invention has been transferred can be verified by mating to retain the foreign DNA stably and then bred as a line harboring that DNA from generation to generation under usual breeding conditions.

The transfer of the foreign DNA of the invention at the fertilized egg cell stage insures that the DNA will be present in excess in all the germ cells and somatic cells of the host mammal. The presence of the foreign DNA of the invention in the germ cells of the DNA-transferred animal following the DNA transfer means that all the germinal cells and somatic cells of all the progeny of the DNA-transferred animal harbor the foreign DNA of the invention in excess. Thus, the progeny of such DNA-transferred animal which inherited the foreign DNA of the invention have the DNA in excess in their germ cells and somatic cells.

By preparing homozygous animals having the transferred DNA in both homologous chromosomes and mating male animals with female animals, it is possible to breed through generations so that every progeny harbors the DNA in excess.

The non-human mammal harboring the normal DNA of the invention features a high expression of the normal DNA and may eventually develop a hyperergasia of the RFRP-3 of the invention through activation of the function of the endogenous normal DNA. Thus, the animal can be utilized as an animal model of that disease. For example, by using the DNA-transferred animal harboring the normal DNA of the invention, it is possible to study the hyperergasia of the RFRP-3 of the invention, to elucidate the mechanisms of diseases with which the RFRP-3 of the invention is associated, and to explore therapeutic modalities for the diseases.

Furthermore, the mammal to which the foreign normal DNA of the invention has been transferred presents symptoms due to an increase in the free RFRP-3 of the invention and, therefore, can also be used in the screening of therapeutic medicines for diseases with which the RFRP-3 of the invention is associated.

On the other hand, the non-human mammal harboring the foreign abnormal DNA of the invention can be verified by mating to retain the DNA stably and then bred as a line harboring the DNA from generation to generation under usual breeding conditions. Moreover, it is possible to incorporate the desired foreign DNA in the above-mentioned plasmid and use it as a starting material. The DNA construct with the promoter can be prepared by conventional recombinant DNA techniques. Transfer of the abnormal DNA of the invention in the fertilized egg cell stage insures that the transferred DNA will be ubiquitous in all the germ cells and somatic cells of the host mammal. The presence of the abnormal DNA of the invention in the germ cells of the DNA-transferred animal means that all the progeny of this DNA-transferred animal harbor the abnormal DNA of the invention in all of their germinal cells and somatic cells. The progeny of this animal harbor the abnormal DNA of the invention in all of their germinal cells and somatic cells. By preparing homozygous male and female animals having the introduced DNA in both homologous chromosomes and mating them, it can be insured that every progeny harbors the DNA from generation to generation.

The non-human mammal harboring the abnormal DNA of the invention features a high expression of the abnormal DNA and, therefore, may eventually develop adiaphoria associated with functional inactivation of the RFRP-3 of the invention through inhibition of the function of the endogenous normal DNA. Thus, the animal can be utilized as an animal model of that disease. For example, by using the DNA-transferred animal harboring the abnormal DNA of the invention, analysis of the mechanism of this functional inactivation adiaphoria attributable to the RFRP-3 of the invention and therapeutic modalities for the disease can be explored.

As a specific potential use, the DNA-transferred animal with a high expression of the abnormal DNA of the invention can be used as a model for elucidating the functional inhibition of the normal polypeptide by the abnormal polypeptide of the invention (dominant negative effect) in adiaphoria of functional inactivation.

Moreover, the DNA-transferred mammal harboring the foreign abnormal DNA of the invention develops symptoms due to an increase in the free polypeptide of the invention and, therefore, can be utilized in the screening of therapeutic medicines for adiaphoria attributable to functional inactivation of the polypeptide of the invention.

As other potential uses of the two types of DNA-transferred animals harboring the two kinds of DNAs of the invention, the following may be considered:

(1) Use as a cell source for tissue culture;
(2) Analysis of those polypeptides which are expressed or activated specifically by the RFRP-3 of the invention, by analyzing the DNA or RNA in tissues of the DNA-transferred animal of the invention or by analyzing the compositions of the peptides expressed by the DNA;
(3) Study of the functions of cells of those tissues which are generally difficult to culture, by using the cells from the tissues containing the DNA as cultured by the standard tissue culture technique;
(4) Screening for medicines capable of enhancing the cell functions by using the cells described in (3); and
(5) Isolation and purification of the mutant RFRP-3 of the invention and construction of antibodies thereto.

Furthermore, by using the DNA-transferred animal of the invention, clinical symptoms of diseases associated with the RFRP-3 of the invention, inclusive of above-described adiaphoria associated with functional inactivation of the RFRP-3 of the invention, can be investigated. In addition, more detailed pathological findings can be obtained in various organs of this model of diseases associated with the RFRP-3 of the invention, thus contributing to the development of new therapies as well as the study and treatment of secondary diseases arising from such diseases.

Moreover, by removing various organs from the DNA-transferred animal of the invention, mincing them and digesting them with a proteolytic enzyme such as trypsin, free single cells harboring the transferred DNA can be recovered. These cells can be cultured for establishment of a cell line. Furthermore, characterization of cells producing the RFRP-3 of the invention can be made and their relationship with apoptosis, differentiation, or proliferation, the mechanism of signal transduction in them, and abnormalities involved can be explored to thereby generate information useful for further elucidation of the RFRP-3 of the invention and its effects.

Moreover, for the development of therapeutic medicines for diseases associated with the RFRP-3 of the invention, such as adiaphoria resulted from functional inactivation of the RFRP-3 of the invention by using the DNA-transferred animal of the invention, an effective and rapid screening technology for such therapeutic medicines can be established by using the test and assay methods described hereinbefore. In addition, by using the above DNA-transferred animal or the foreign DNA expression vector of the invention, gene therapies for diseases associated with the RFRP-3 of the invention can be explored and developed.

(10) Knockout Animals

The invention further provides non-human mammalian embryonic stem cells wherein the DNA of the invention is inactivated, and non-human mammals deficient in expression of the DNA of the invention wherein the DNA of the invention is deactivated.

The invention, therefore, provides:
(1) A non-human mammalian embryonic stem cell wherein the DNA of the invention is inactivated;
(2) The embryonic stem cell according to in (1) wherein the DNA is inactivated by introduction of a reporter gene (e.g. *E. coli*-derived β-galactosidase gene);
(3) The embryonic stem cell according to (1) which is neomycin-resistant;
(4) The embryonic stem cell according to (1) wherein the non-human mammal is a rodent;
(5) The embryonic stem cell according to (4) wherein the rodent is mouse;
(6) A non-human mammal deficient in expression of the DNA of the invention, wherein the DNA is inactivated;
(7) The non-human mammal according to (6) wherein the DNA is inactivated by introduction of a reporter gene (e.g. *E. coli*-derived β-galactosidase gene) and the reporter gene can be expressed under the control of the promoter for the DNA of the invention;
(8) The non-human mammal according to (6) wherein the non-human mammal is a rodent;
(9) The non-human mammal according to (8) wherein the rodent is mouse; and
(10) A method for screening for compounds, or salts thereof, that enhance or inhibit the promoter activity for the DNA of the invention, which comprises administering a test compound to the non-human mammal according to (7) and detecting expression of the reporter gene.

The expression "non-human mammalian embryonic stem cell wherein the DNA of the invention is inactivated" means the embryonic stem cell (hereinafter referred to briefly as ES cell) of a non-human mammal in which the DNA has been deprived of the capacity to express the RFRP-3 of the invention (hereinafter, sometimes referred to as the "knockout DNA of the invention") through introduction of an artificial mutation to the DNA of the invention possessed by the non-human mammal to thereby inhibit expression of the DNA of the invention or through substantial deprivation of the activity of the RFRP-3 of the invention encoded by the DNA.

As the non-human mammals, the same animals as mentioned hereinbefore may be used.

Examples of the method for introducing an artificial mutation to the DNA of the invention are a deletion of some or all of the DNA sequence, or an insertion of a different DNA, or substitution with a different DNA by the genetic engineering technology. The knockout DNA of the invention may be created by such a mutation that would shift the reading frame or destroy the function of the promoter or exon.

The non-human mammalian embryonic stem cell wherein the DNA of the invention is inactivated (hereinafter referred to as the "DNA inactivated ES cell of the invention" or the "knockout ES cell of the invention") can be prepared by, for example, procedures which comprise isolating the DNA of the invention from a desired non-human mammal, inserting a medicine-resistance gene, typically neomycin-resistance gene or hygromycin-resistance gene, or a reporter gene such as lacZ (β-galactosidase gene) or cat (chloramphenicol acetyltransferase gene) into its exon region to disrupt the function of the exon or inserting a DNA sequence for terminating gene transcription (e.g. poly A addition signal) in an intron region between exons to thereby inhibit synthesis of a complete mRNA, introducing the thus-constructed DNA strand having a DNA sequence designed to eventually disrupt the gene (hereinafter, referred to briefly as the "targeting vector") into the chromosomes of the host animal by homologous recombination, subjecting the resulting ES cell to Southern hybridization analysis using a DNA sequence located on the DNA of the invention or in its vicinity as a probe or a PCR procedure using a DNA sequence located on the targeting vector and a DNA sequence in the vicinity but not including the DNA of the invention used in the construction of the targeting vector as primers, and selecting the knockout ES cell of the invention.

The original ES cell to be used for inactivation of the DNA of the invention by the homologous recombination technique or the like may be an already established cell line such as those mentioned hereinbefore or a new cell line established de novo by the known method of Evans and Kaufman. Taking mouse ES cells as an example, ES cells of the 129 line are generally employed but the immunological background of this line is not clear. Therefore, the cell line established by using $BDF_1$ mice created by the hybridization of C57BL/6 mice and C57BL/6 mice, both yielding few eggs, with DBA/2 mice ($BDF_1=F_1$ of C57BL/6 and DBA/2) for preparing pure-line ES cells with an immunologically defined genetic background can be used with advantage. In addition to the advantage of high egg output and sturdiness of the egg, $BDF_1$ mice have the background of C57BL/6 mice so that in the construction of a disease model with ES cells obtained, the genetic background of the model mice can be converted to that of C57BL/6 mice by back-crossing with C57BL/6.

Moreover, in establishing an ES cell line, it is common practice to use blastocytes 3.5 days following fertilization but, aside from them, a large number of early embryos can be prepared with high efficiency by harvesting the embryos at the 8-cell stage and culturing them into blastocytes.

Furthermore, while ES cells from both male and female animals can be used, generally ES cells of male animals are more convenient for the construction of reproduction line chimeras. Moreover, for the purpose of reducing the burden of the complicated cultural procedure, it is preferable to carry out sexing as early as possible.

As a typical method for sexing ES cells, there can be mentioned the method in which the gene in the sex determination region on the Y chromosome is amplified and detected by PCR. Whereas the conventional karyotype analysis requires about $10^6$ cells, the above method requires only about one colony equivalent of ES cells (about 50 cells). Therefore, the primary selection of ES cells in an early stage can be made by this sexing method. Since male cells can thus be selected in the early stage, the trouble in the initial stage of culture can be drastically reduced.

Moreover, the secondary selection can be carried out by G-banding for the number of chromosomes. The number of chromosomes in the resulting ES cell is preferably 100% of the normal number but this goal may not be reached due to the physical and other factors involved in the establishment of the line. In such cases, it is preferable to knockout the gene of the ES cell and re-clone it into the normal cell (taking a mouse as an example, the cell in which the number of chromosomes is 2n=40).

The embryonic stem cell line thus established is generally very satisfactory in proliferation characteristic but since it is liable to lose its ontogenic ability, it must be subcultured with sufficient care. For example, this cell line should be cultured on suitable feeder cells such as STO fibroblasts in the presence of LIF (1–10000 U/ml) in a carbon dioxide incubator (preferably 5% $CO_2$, 95% air or 5% oxygen, 5% $CO_2$, 90% air) at about 37° C. and, in subculture, it should be treated with trypsin/EDTA solution (generally 0.001–0.5% trypsin/0.1–5 mM EDTA, preferably about 0.1% trypsin/1 mM EDTA) to provide single cells and seed them on freshly prepared feeder cells. While such subculture is generally performed every 1–3 days, it is good practice to observe the cells on each occasion and, whenever morphologically abnormal cells are discovered, discard the culture.

ES cells can be allowed to differentiate into various types of cells, such as head long muscle cells, visceral muscle cells, heart muscle cells, and so forth by conducting monolayer culture to a high density under suitable conditions or suspension culture until a mass of cells is formed (M. J. Evans & M. H. Kaufman, Nature, 292, 154, 1981; G. R. Martin, Proceedings of National Academy of Science USA, 78, 7634, 1981; T. C. Doetschman et al., Journal of Embryology and Experimental Morphology, 87, 27, 1985), and the cell deficient in expression of the DNA of the invention as obtainable by causing the ES cell of the invention to differentiate is useful for the cytobiological in vitro study of the RFRP-3 of the invention.

The non-human mammal deficient in expression of the DNA of the invention can be differentiated from normal animals by assaying the mRNA in the animals by the known method and comparing the amounts of expression indirectly.

As the non-human mammal used for this purpose, the same animals as mentioned hereinbefore may be used.

With respect to the non-human mammal deficient in expression of the DNA of the invention, the DNA of the invention can be knocked out by introducing the targeting vector constructed as described above into, for example, mouse embryonic stem cells or mouse egg cells and thereby allowing the DNA sequence of the targeting vector harboring the inactivated DNA of the invention to undergo homologous recombination with, and accordingly replacing, the DNA of the invention on the mouse embryonic stem cell or egg cell chromosomes.

The cell with the DNA of the invention thus knocked out can be judged by Southern hybridization analysis using a DNA sequence on the DNA of the invention or in its vicinity as a probe or by PCR using a DNA sequence on the targeting vector or a mouse-derived DNA sequence in a region adjacent to but not including the DNA of the invention used in the targeting vector as primers. When a non-human mammalian embryonic stem cell is used, a cell line with the DNA of the invention knocked out by the homologous recombination technique is cloned and injected into the non-human mammalian embryo or blastocyte at a suitable stage of embryogenesis, for example at the 8-cell stage, and the resulting chimera embryo is transplanted in the pseudopregnant uterus of the non-human mammal. The animal thus obtained is a chimera animal constituted by both the cells harboring the normal DNA locus of the invention and the cells harboring the artificially mutated DNA locus of the invention.

When some of the gametes of this chimera animal harbor the mutated DNA locus of the invention, an individual whose entire tissue is constituted by cells harboring the mutated DNA locus of the invention can be screened from the colony of animals obtained by crossing such a chimera animal with a normal animal, for example by coat color discrimination. The individuals thus selected are usually animals hetero-deficient in expression of the RFRP-3 of the invention and by mating such individuals hetero-deficient in expression of the RFRP-3 of the invention with each other, animals homo-deficient in expression of the RFRP-3 of the invention can be acquired.

When egg cells are used, a transgenic non-human mammal with the targeting vector having been introduced into its chromosomes can be prepared by injecting the DNA solution into the egg cell nucleus by the microinjection technique and selecting animals expressing a mutation of the DNA of the invention by homologous recombination.

The individuals with the DNA of the invention thus knocked out are mated to verify that the animals obtained by mating also have the DNA knocked out and they can be sub-bred under the usual breeding conditions.

Preparation and maintenance of the germ line may also be carried out in accordance with conventional methods. Thus, by mating male and female animals harboring the inactivated DNA, homozygotes having the inactivated DNA in both homologous chromosomes can be obtained. The homozygotes thus obtained are bred under such condition that, with regard to the dam, the number of homozygotes is plural per normal individual. By mating male and female heterozygotes, homozygotes and heterozygotes both harboring the inactivated DNA can be sub-bread.

The non-human mammalian embryonic stem cell harboring the inactivated DNA of the invention is very useful for the construction of non-human mammals deficient in expression of the DNA of the invention.

Moreover, the mammal deficient in expression of the DNA of the invention lacks various biological activities inducible by the RFRP-3 of the invention or the receptor protein of the invention and can, therefore, be of use as an animal model of diseases arising from inactivation of the biological activities of the RFRP-3 of the invention or the receptor protein of the invention, thus being useful in the etiological studies of such diseases and development of therapeutic methods.

(10a) Method of Screening for Compounds with Therapeutic/Prophylactic Effect Upon Diseases Resulted from Deficiency or Damage of the DNA of the Invention Non-human mammals deficient in expression of the DNA of the invention may be used for screening for compounds with a therapeutic and/or prophylactic effect upon diseases resulted from deficiency or damage of the DNA of the invention.

The present invention provides a method of screening for compounds, or salts thereof, having a therapeutic and/or prophylactic effect upon diseases resulted from deficiency or damage of the DNA of the invention, which is characterized by administering a test compound to a non-human mammal deficient in expression of the DNA of the invention and observing and measuring the changes in the mammal.

As the non-human mammal deficient in expression of the DNA of the invention used in the above screening method, the same animals as described earlier may be used.

The test compound may be, for example, a peptide, protein, non-peptidic compound, synthetic compound, fermentation product, cell extract, plant extract, animal tissue extract or plasma. These compounds may be either novel compounds or known compounds.

Specifically, a non-human mammal deficient in expression of the DNA of the invention is treated with a test compound and then compared with a control animal not treated with the compound. Subsequently, the therapeutic and/or prophylactic effect of the test compound may be examined using the changes in individual organs, tissues or disease symptoms in the mammal as indicators.

As a method for treating a test animal with a test compound, oral administration, intravenous injection, or the like may be used. The method may be appropriately selected depending on the symptoms of the test animal, the nature of the test compound, and so on. Dose levels of the test compound may be appropriately selected taking into account of the administration method, the nature of the test compound, and so on. Further, dose levels of the test compound may be appropriately selected depending on the administration method, the nature of the relevant test compound, and so on.

When compounds that have a therapeutic and/or prophylactic effect upon diseases associated with insufficient prolactin secretion (e.g. hypoovarianism, seminal vesicle hypoplasia, osteoporosis, menopausal syndrome, hypogalactia, hypothyroidism or renal insufficiency), diseases associated with excessive prolactin secretion (e.g. hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma or Sheehan's syndrome or spermatogenic disorder), paralgesia, or the like is screened for, test compounds are administered to non-human mammals deficient in the expression of the DNA of the invention, followed by measurement of the time course of blood prolactin levels, and so forth in the mammals.

In the above screening method, when a test compound has been administered to a test animal and, as a result, the amount of prolactin secretion of the test animal has changed by about 10% or more, preferably by about 30% or more, more preferably by about 50% or more, the test compound can be selected as a compound that has a therapeutic and/or prophylactic effect upon the above-described diseases.

Compounds obtainable by using the screening method of the invention are compounds selected from the above-mentioned test compounds and have a therapeutic and/or prophylactic effect upon diseases resulted from deficiency or damage of the RFRP-3 of the invention. Therefore, they may be used as medicines that are safe and of low toxicity, such as prophylactic and/or therapeutic agents for those diseases that are safe and of low toxicity. Furthermore, compounds derived from those compounds obtained by the above screening may also be used in the same manner.

The compound obtained by the above screening may be in a salt form. As salts of the compounds, salts formed with physiologically acceptable acids (e.g. organic or inorganic acids) or bases (e.g. alkali metals) may be used. Especially preferable are physiologically acceptable acid addition salts. Examples of such salts include salts formed with inorganic acids (e.g. hydrochloric acid, phosphoric acid, hydrobromic acid or sulfuric acid) and salts formed with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid).

Medicines comprising the compound, or a salt thereof, obtained by the above screening may be prepared in the same manner as described for medicines comprising the RFRP-3 of the invention.

Since the thus obtained preparations are safe and of low toxicity, they may be administered to, for example, human and other mammals (such as rat, mouse, guinea pig, rabbit, sheep, pig, bovine, horse, cat, dog, monkey, and so forth).

Dose levels of the above compound or a salt thereof may vary depending upon the target disease, the patient to be treated, administration route, and so on. When the compound is administered orally, generally the compound is administered to adult patients with hypothyroidism (60 kg in body weight) at a dose of about 0.1–100 mg/day, preferably about 1.0–50 mg/day, more preferably about 1.0–20 mg/day. With respect to parenteral administration, when the compound is administered to adult patients with hypothyroidism (60 kg in body weight), for example, in the form of an injection, it is convenient to intravenously inject the compound at a dose of about 0.01–30 mg/day, preferably about 0.1–20 mg/day, and more preferably about 0.1–10 mg/day, though the dose per administration may vary depending on the patient to be treated, the target disease, and so forth. For other animals, corresponding doses may be administered after appropriate conversion of the above-mentioned values per 60 kg.

(10b) Method of Screening for Compounds that Promote or Inhibit the Activity of the Promoter for the DNA of the Invention The present invention provides a method of screening for compounds, or salts thereof, that promote or inhibit the activity of the promoter for the DNA of the invention, which is characterized by administering a test compound to a non-human mammal deficient in expression of the DNA of the invention and detecting the expression of a reporter gene.

In the above screening method, there is used a non-human mammal deficient in expression of the DNA of the invention wherein the DNA of the invention is inactivated as a result of introduction of a reporter gene, and this reporter gene is capable of being expressed under the control of the promoter for the DNA of the invention.

As the test compound, the compounds as enumerated above may be used.

As the reporter gene, the genes as enumerated above may be used. Among all, β-galactosidase gene (lacZ), soluble alkali phosphatase gene or luciferase gene may be preferably used.

In the non-human mammal deficient in expression of the DNA of the invention wherein the DNA of the invention is replaced with a reporter gene, since the reporter gene is present under the control of the promoter for the DNA of the invention, the promoter activity can be detected by tracing the expression of the substance encoded by the reporter gene.

For example, when a part of the DNA region encoding the RFRP-3 of the invention is replaced with $E.\ coli$-derived β-galactosidase gene (lacZ), β-galactosidase is expressed instead of the RFRP-3 of the invention in those tissues where originally the RFRP-3 of the invention has been expressed. Thus, by staining with a substrate for β-galactosidase such as 5-bromo-4-chloro-3-indolyl-β-D-galactopyrasosidase (X-gal), it is possible to observe the state of in vivo expression of the RFRP-3 of the invention in the mammal simply. Specifically, mice deficient in the RFRP-3 of the invention or tissue sections thereof may be fixed in glutaraldehyde or the like, washed with phosphate-buffered physiological saline (PBS), and treated with a staining solution containing X-gal at room temperature or around 37° C. for about 30 min to 1 hr. Subsequently, the tissue samples are washed with 1 mM EDTA/PBS solution to terminate the β-galactosidase reaction, followed by observation of the resultant color development. Alternatively, mRNA encoding lacZ may be detected according to conventional methods.

The compounds or salts thereof obtainable by the above-described screening are compounds that are selected from the above-mentioned test compounds and yet promote or inhibit the promoter activity for the DNA of the invention.

The compound obtained by the above screening may be in a salt form. As salts of the compound, salts formed with physiologically acceptable acids (e.g. organic or inorganic acids) or bases (e.g. alkali metals) may be used. Especially preferable are physiologically acceptable acid addition salts. Examples of such salts include salts formed with inorganic acids (e.g. hydrochloric acid, phosphoric acid, hydrobromic acid or sulfuric acid) and salts formed with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid).

Since compounds, or salts thereof, that promote the promoter activity for the DNA of the invention can promote the expression of the RFRP-3 of the invention and thereby promote the function thereof, they may be used as prophylactic and/or therapeutic agents for various diseases associated with prolactin secretion insufficiency, and useful, based on their prolactin secretion-promoting effect, as prophylactic and/or therapeutic agents for various diseases associated with prolactin secretion such as hypoovarianism, seminal vesicle hypoplasia, osteoporosis, menopausal syndrome, hypogalactia, hypothyroidism, renal insufficiency, and so forth or paralgesia.

Further, since those compounds or salts thereof have aphrodisiac effect (pheromone-like effect) based on their prolactin secretion-promoting effect, they are also useful as an aphrodisiac agent.

Since compounds, or salts thereof, that inhibit the promoter activity for the DNA of the invention can inhibit the expression of the RFRP-3 of the invention and thereby inhibit the function thereof, they may be used as prophylactic and/or therapeutic agents for various diseases associated with excessive prolactin secretion, and useful, based on their prolactin secretion-inhibiting effect, as prophylactic and/or therapeutic agents for various diseases associated with prolactin secretion such as hyperprolactinemia, pituitary adenoma, diencephalic tumor, menstrual disorder, stresses, autoimmune diseases, prolactinoma, sterility, impotence, amenorrhea, galactorrhea, acromegaly, Chiari-Frommel syndrome, Argonz-del Castillo syndrome, Forbes-Albright syndrome, breast cancer lymphoma or Sheehan's syndrome or spermatogenic disorder, and so forth.

Further, those compounds or salts thereof are also useful as a contraceptive based on their prolactin secretion-inhibiting effect.

Further, those compounds or salts thereof are also useful as an analgesic agent.

Additionally, those compounds or salts thereof obtainable of the above screening method are also useful as a medicine for testing prolactin secretion function or a veterinary medicine such as a promoting agent for milk secretion in mammals such as bovine, goat, pig, and so forth. Besides, it is expected to apply those compounds or salts thereof to a useful substance production system where the useful substance is allowed to be produced in mammal bodies and then secreted into their milk.

Further, since those compounds or salts thereof have placental function-regulating effect, they are also useful as a prophylactic and/or therapeutic agent for choriocarcinoma, hydatidiform mole, invasive mole, miscarriage, fetal hypotrophy, glucose metabolism disorder, lipidosis or induction of delivery.

Further, compounds derived from those compounds obtained from the above screening may also be used in the same manner.

Medicines comprising the compound or, a salt thereof, obtained by the above screening may be prepared in the same manner as described for medicines comprising the RFRP-3 of the invention or a salt thereof.

Since the thus obtained preparations are safe and of low toxicity, they may be administered to, for example, human or other mammals (such as rat, mouse, guinea pig, rabbit, sheep, pig, bovine, horse, cat, dog, monkey, and so forth).

Dose levels of the above compound or a salt thereof may vary depending upon the target disease, the patient to be treated, administration route, and so on. When a compound that promotes the promoter activity for the DNA of the invention is administered orally, generally the compound is administered to adult patients with hypothyroidism (60 kg in body weight) at a dose of about 0.1–100 mg/day, preferably about 1.0–50 mg/day, more preferably about 1.0–20 mg/day. With respect to parenteral administration, when a compound that promotes the promoter activity for the DNA of the invention is administered to adult patients with hypothyroidism (60 kg in body weight), for example, in the form of an injection, it is convenient to intravenously inject the compound at a dose of about 0.01–30 mg/day, preferably about 0.1–20 mg/day, and more preferably about 0.1–10 mg/day, though the dose per administration may vary depending on the patient to be treated, the target disease, and so forth. For other animals, corresponding doses may be administered after appropriate conversion of the above-mentioned values per 60 kg.

On the other hand, when a compound that inhibits the promoter activity for the DNA of the invention is administered orally, generally the compound is administered to adult patients with hyperprolactinemia (60 kg in body weight) at a dose of about 0.1–100 mg/day, preferably about 1.0–50 mg/day, more preferably about 1.0–20 mg/day. With respect to parenteral administration, when a compound that inhibits the promoter activity for the DNA of the invention is administered to adult patients with hyperprolactinemia (60 kg in body weight) in the form of an injection, it is convenient to intravenously inject the compound at a dose of about 0.01–30 mg/day, preferably about 0.1–20 mg/day, and more preferably about 0.1–10 mg/day, though the dose per administration may vary depending on the patient to be treated, the target disease, and so forth. For other animals, corresponding doses may be administered after appropriate conversion of the above-mentioned values per 60 kg.

Thus, the non-human mammal deficient in expression of the DNA of the invention is extremely useful in screening for compounds, or salts thereof, that promote or inhibit the promoter activity for the DNA of the invention, and may contribute greatly to the elucidation of causes of various diseases resulted from deficiency in expression of the DNA of the invention, or to the development of prophylactic and/or therapeutic agents for such diseases.

When the so-called transgenic animal is created by using a DNA comprising the promoter region of the RFRP-3 of the invention, ligating genes encoding various proteins downstream of the promoter region, and injecting the thus prepared construct into egg cells of an animal, it is possible to allow the animal to synthesize its RFRP-3 specifically, which will enable the examination of the in vivo function of the RRRP-3. Further, if a cell line which expresses an appropriate reporter gene ligated to the above promoter region has been established, such a cell line may be used as a search system for those low molecular weight compounds that specifically promote or inhibit in vivo production ability for the RFRP-3 of the invention per se.

In the specification and drawings of the present application, the abbreviations used for bases (nucleotides), amino acids and so forth are those recommended by the IUPAC-IUB Commission on Biochemical Nomenclature or those conventionally used in the art. Examples of such abbreviations are given below. Amino acids that may have optical isomers are intended to represent their L-isomer unless otherwise specified.

DNA: Deoxyribonucleic acid
cDNA: Complementary deoxyribonucleic acid
A: Adenine
T: Thymine
G: Guanine
C: Cytosine
I: Inosine
R: Adenine (A) or Guanine (G)
Y: Thymine M or Cytosine (C)
M: Adenine (A) or Cytosine (C)
K: Guanine (G) or Thymine (T)
S: Guanine (G) or Cytosine (C)
W: Adenine (A) or Thymine (I)
B: Guanine (G), Guanine (G) or Thymine Cr)
D: Adenine (A), Guanine (G) or Thymine Cr)
V: Adenine (A), Guanine (G) or Cytosine (C)
N: Adenine (A), Guanine (G), Cytosine (C) or Thymine (T), or unknown or other nucleotide
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetracetic acid
SDS: Sodium dodecyl sulfate
BHA: Banzhydrylamine
pMBHA: p-Methylbenzhydrylamine
Tos: p-Toluene sulfonyl
Bzl: Benzyl
Bom: Benzyloxymethyl
Boc: t-Butyloxycarbonyl
DCM: Dichloromethane
HOBt: 1-Hydroxybenzotriazole
DCC: N,N'-Dicyclohexylcarbodiimide
TFA: Trifluoroacetate
DIEA: Diisopropylethylamine
Gly: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro or P: Proline
Asn or N: Asparagine
Gln or Q: Glutamine
pGlu: Pyroglutamic acid
BHA: Banzhydrylamine
pMBHA: p-Methylbenzhydrylamine
Tos: p-Toluene sulfonyl
Bzl: Benzyl
OcHex: Cyclohexyl ester
Boc: t-Butyloxycarbonyl
DCM: Diclhoromethane
HOBt: 1-Hydroxybenztriazole
DCC: N,N'-Dicyclohexylcarbodiimide
TFA: Trifluoroacetate
DIEA: Diisopropylethylamine The SEQ ID NOS of the SEQUENCE LISTING of the present specification represent the sequences as indicated below.

[SEQ ID NO: 1]
This shows the amino acid sequence of the polypeptide of the invention (human type) obtained in Reference Example 1 described later.

[SEQ ID NO: 2]
This shows the nucleotide sequence of a DNA encoding the polypeptide of the invention comprising the amino acid sequence represented by SEQ ID NO: 1.

[SEQ ID NO: 3]
This shows the nucleotide sequence of primer F5 used in the Reference Example 1 described later.

[SEQ ID NO: 4]
This shows the nucleotide sequence of primer F6 used in the Reference Example 1 described later.

[SEQ ID NO: 5]
This shows the nucleotide sequence of primer F1 used in the Reference Example 1 described later.

[SEQ ID NO: 6]
This shows the nucleotide sequence of primer R5 used in the Reference Example 1 described later.

[SEQ ID NO: 7]
This shows the nucleotide sequence of primer hR1 used in the Reference Example 3 described later.

[SEQ ID NO: 8]
This shows the amino acid sequence of the polypeptide of the invention (human type) obtained in Reference Example 3 described later.

[SEQ ID NO: 9]
This shows the nucleotide sequence of a DNA encoding the polypeptide of the invention comprising the amino acid sequence represented by SEQ ID NO: 8.

[SEQ ID NO: 10]
This shows the nucleotide sequence of primer bF6 used in the Reference Example 4 described later.

[SEQ ID NO: 11]
This shows the nucleotide sequence of primer bF7 used in the Reference Example 4 described later.

[SEQ ID NO: 12]
This shows the nucleotide sequence of primer bR6 used in the Reference Example 4 described later.

[SEQ ID NO: 13]
This shows the nucleotide sequence of primer bR7 used in the Reference Example 4 described later.

[SEQ ID NO: 14]
This shows the amino acid sequence of the polypeptide of the invention (bovine type) obtained in the Reference Example 4 described later.

[SEQ ID NO: 15]
This shows the nucleotide sequence of a DNA encoding the polypeptide of the invention comprising the amino acid sequence represented by SEQ ID NO: 14.

[SEQ ID NO: 16]
This shows the nucleotide sequence of primer rLPR1 used in the Reference Example 5 described later.

[SEQ ID NO: 17]
This shows the nucleotide sequence of primer rLPF1 used in the Reference Example 5 described later.

[SEQ ID NO: 18]
This shows the amino acid sequence of the polypeptide of the invention (rat type) obtained in the Reference Example 5 described later (before re-cloning).

[SEQ ID NO: 19]
This shows the nucleotide sequence of a DNA encoding the polypeptide of the invention comprising the amino acid sequence represented by SEQ ID NO: 18.

[SEQ ID NO: 20]
This shows a nucleotide sequence encoding RFGK sequence.

[SEQ ID NO: 21]
This shows a nucleotide sequence encoding RFGR sequence.

[SEQ ID NO: 22]
This shows a nucleotide sequence encoding RSGK sequence.

[SEQ ID NO: 23]
This shows a nucleotide sequence encoding RSGR sequence.

[SEQ ID NO: 24]
This shows a nucleotide sequence encoding RLGK sequence.

[SEQ ID NO: 25]
This shows a nucleotide sequence encoding RLGR sequence.

[SEQ ID NO: 26]
This shows the nucleotide sequence of primer FF2 used in the Reference Example 6 described later.

[SEQ ID NO: 27]
This shows the nucleotide sequence of primer rR4 used in the Reference Example 6 described later.

[SEQ ID NO: 28]
This shows the nucleotide sequence of primer mF1 used in the Reference Example 6 described later.

[SEQ ID NO: 29]
This shows the nucleotide sequence of primer mF3 used in the Reference Example 6 described later.

[SEQ ID NO: 30]
This shows the nucleotide sequence of primer mR1 used in the Reference Example 6 described later.

[SEQ ID NO: 31]
This shows the nucleotide sequence of primer moF used in the Reference Example 6 described later.

[SEQ ID NO: 32]
This shows the nucleotide sequence of primer moR used in the Reference Example 6 described later.

[SEQ ID NO: 33]
This shows the amino acid sequence of the polypeptide of the invention (mouse type) obtained in the Reference Example 6 described later.

[SEQ ID NO: 34]
This shows the nucleotide sequence of a DNA encoding the polypeptide of the invention comprising the amino acid sequence represented by SEQ ID NO: 33.

[SEQ ID NO: 35]
This shows the nucleotide sequence of primer 1 used for cloning the cDNA encoding the novel G protein-coupled receptor protein rOT7T022L derived from the peripheral area of rat brainstem obtained in Reference Example 7 described later.

[SEQ ID NO: 36]
This shows the nucleotide sequence of primer 2 used for cloning the cDNA encoding the novel G protein-coupled receptor protein rOT7T022L derived from the peripheral area of rat brainstem obtained in Reference Example 7 described later.

[SEQ ID NO: 37]
This shows the amino acid sequence of the novel G protein-coupled receptor protein rOT7T022L derived from the peripheral area of rat brainstem obtained in Reference Example 7 described later.

[SEQ ID NO: 38]
This shows the nucleotide sequence of the cDNA encoding the novel G protein-coupled receptor protein rOT7T022L derived from the peripheral area of rat brainstem obtained in Reference Example 7 described later.

[SEQ ID NO: 39]
This shows the amino acid sequence of the peptide obtained in (3) in Reference Example 7 described later.

[SEQ ID NO: 40]
This shows the amino acid sequence of the peptide obtained in (4) in Reference Example 7 described later.

[SEQ ID NO: 41]
This shows the amino acid sequence of the peptide obtained in (5) in Reference Example 7 described later.

[SEQ ID NO: 42]
This shows a nucleotide sequence encoding a peptide comprising an amino acid sequence which is from position 81 (Met) to position 92 (Phe) of the amino acid sequence represented by SEQ ID NO: 1.

[SEQ ID NO: 43]
This shows a nucleotide sequence encoding a peptide comprising an amino acid sequence which is from position 101 (Ser) to position 112 (Ser) of the amino acid sequence represented by SEQ ID NO: 1.

[SEQ ID NO: 44]
This shows a nucleotide sequence encoding a peptide comprising an amino acid sequence which is from position 124 (Val) to position 131 (Phe) of the amino acid sequence represented by SEQ ID NO: 1.

[SEQ ID NO: 45]
This shows a nucleotide sequence encoding a peptide comprising an amino acid sequence which is from position 1 (Met) to position 92 (Phe) of the amino acid sequence represented by SEQ ID NO: 1.

[SEQ ID NO: 46]

This shows a nucleotide sequence encoding a peptide comprising an amino acid sequence which is from position 1 (Met) to position 112 (Ser) of the amino acid sequence represented by SEQ ID NO: 1.

[SEQ ID NO: 47]

This shows a nucleotide sequence encoding a peptide comprising an amino acid sequence which is from position 1 (Met) to position 131 (Phe) of the amino acid sequence represented by SEQ ID NO: 1.

[SEQ ID NO: 48]

This shows the nucleotide sequence of primer ratF2 used in Reference Example 5.

[SEQ ID NO: 49]

This shows the nucleotide sequence of primer ratR used in Reference Example 5.

[SEQ ID NO: 50]

This shows the amino acid sequence of the polypeptide of the invention (rat type) obtained in the Reference Example 5 described later (after re-cloning).

[SEQ ID NO: 51]

This shows the nucleotide sequence of a DNA encoding the polypeptide of the invention comprising the amino acid sequence represented by SEQ ID NO: 50.

[SEQ ID NO: 52]

This shows the nucleotide sequence of primer bFF used in Reference Example 9.

[SEQ ID NO: 53]

This shows the nucleotide sequence of primer bFR used in Reference Example 9.

[SEQ ID NO: 54]

This shows the amino acid sequence encoding the protein (polypeptide) designated hOT7T022 obtained in Reference Example 11.

[SEQ ID NO: 55]

This shows the nucleotide sequence of a DNA encoding the protein (polypeptide) designated hOT7T022 comprising the amino acid sequence represented by SEQ ID NO: 54.

[SEQ ID NO: 56]

This shows the nucleotide sequence of a DNA encoding the protein (polypeptide) designated hOT7T022 comprising the amino acid sequence represented by SEQ ID NO: 54.

[SEQ ID NO: 57]

This shows the nucleotide sequence of primer 1 used in Reference Example 11.

[SEQ ID NO: 58]

This shows the nucleotide sequence of primer 2 used in Reference Example 11.

[SEQ ID NO: 59]

This shows the nucleotide sequence of primer #1 used in Example A4.

[SEQ ID NO: 60]

This shows the nucleotide sequence of primer #2 used in Example A4.

[SEQ ID NO: 61]

This shows the nucleotide sequence of primer #3 used in Example A4.

[SEQ ID NO: 62]

This shows the nucleotide sequence of primer #4 used in Example A4.

[SEQ ID NO: 63]

This shows the amino acid sequence of a peptide comprising an amino acid sequence which is from position 104 (Ala) to position 131 (Phe) of the amino acid sequence represented by SEQ ID NO: 1.

[SEQ ID NO: 64]

This shows the nucleotide sequence of a DNA encoding a peptide comprising an amino acid sequence which is from position 104 (Ala) to position 131 (Phe) of the amino acid sequence represented by SEQ ID NO: 1.

[SEQ ID NO: 65]

This shows the amino acid sequence of a peptide comprising an amino acid sequence which is from position 101 (Ser) to position 131 (Phe) of the amino acid sequence represented by SEQ ID NO: 1.

[SEQ ID NO: 66]

This shows the nucleotide sequence of a DNA encoding a peptide comprising an amino acid sequence which is from position 101 (Ser) to position 131 (Phe) of the amino acid sequence represented by SEQ ID NO: 1.

[SEQ ID NO: 67]

This shows the amino acid sequence of a peptide comprising an amino acid sequence which is from position 104(Ala) to position 131 (Phe) of the amino acid sequence represented by SEQ ID NO: 14.

[SEQ ID NO: 68]

This shows the nucleotide sequence of a DNA encoding a peptide comprising an amino acid sequence which is from position 104 (Ala) to position 131 (Phe) of the amino acid sequence represented by SEQ ID NO: 14.

[SEQ ID NO: 69]

This shows the amino acid sequence of peptide RFRP-3 (5) comprising an amino acid sequence which is from position 127 (Leu) to position 131 (Phe) of the amino acid sequence represented by SEQ ID NO: 1 or SEQ ID NO: 12.

[SEQ ID NO: 70]

This shows the amino acid sequence of peptide RFRP-3 (6) comprising an amino acid sequence which is from position 126 (Asn) to position 131 (Phe) of the amino acid sequence represented by SEQ ID NO: 1 or SEQ ID NO: 12.

[SEQ ID NO: 71]

This shows the amino acid sequence of peptide RFRP-3 (7) comprising an amino acid sequence which is from position 125 (Pro) to position 131 The) of the amino acid sequence represented by SEQ ID NO: 1 or SEQ ID NO: 12.

[SEQ ID NO: 72]

This shows the amino acid sequence of peptide RFRP-3 (8) comprising an amino acid sequence which is from position 124 (Val) to position 131 (Phe) of the amino acid sequence represented by SEQ ID NO: 1 or SEQ ID NO: 12.

Transformant *Escherichia coli* JM109/phRF1 obtained in Reference Example 2 described later has been deposited with the International Patent Organism Depository, National Institute of Advanced Industrial Science and Technology (former designation: National Institute of Bioscience and Human Technology, Agency of Industrial Science and Technology, Ministry of International Trade and Industry (NIBH)) located at Central 6, 1-1 Higashi 1-chome, Tsukuba City, Ibaraki Pref., Japan (zip code No.: 305-8566) since Apr. 14, 1999 under the Accession No. FERM BP-6702, and with the Institute for Fermentation, Osaka (IFO) since Mar. 5, 1999 under the Accession No. IFO 16265.

Transformant *Escherichia coli* DH10B/pAK-rOT022L obtained in Reference Example 7 described later has been deposited with the International Patent Organism Depository, National Institute of Advanced Industrial Science and Technology (former designation: NIBH) since Nov. 2, 1998 under the Accession No. FERM BP-6558, and with the Institute for Fermentation, Osaka (IFO) since Oct. 16, 1998 under the Accession No. IFO 16211.

Transformant *Escherichia coli* JM109/pbRF2 obtained in Reference Example 9 described later has been deposited with the International Patent Organism Depository, National Institute of Advanced Industrial Science and Technology (former designation: NIBH) since Aug. 2, 1999 under the Accession No. FERM BP-6811, and with the Institute for Fermentation, Osaka (IFO) since Jun. 18, 1999 under the Accession No. IFO 16288.

Transformant *Escherichia coli* JM109/phRF2 obtained in Reference Example 8 described later has been deposited with the International Patent Organism Depository, National Institute of Advanced Industrial Science and Technology (former designation: NIBH) since Aug. 2, 1999 under the Accession No. FERM BP-6812, and with the Institute for Fermentation, Osaka (IFO) since Jun. 18, 1999 under the Accession No. IFO 16289.

Transformant *Escherichia coli* JM109/pmLP4 obtained in Reference Example 6 described later has been deposited with the International Patent Organism Depository, National Institute of Advanced Industrial Science and Technology (former designation: NIBH) since Aug. 2, 1999 under the Accession No. FERM BP-6813, and with the Institute for Fermentation, Osaka (IFO) since Jun. 18, 1999 under the Accession No. IFO 16290.

Transformant *Escherichia coli* JM109/prLOL6 obtained in Reference Example 5 described later has been deposited with the International Patent Organism Depository, National Institute of Advanced Industrial Science and Technology (former designation: NIBH) since Aug. 2, 1999 under the Accession No. FERM BP-6814, and with the Institute for Fermentation, Osaka (IFO) since Jun. 18, 1999 under the Accession No. IFO 16291.

Transformant *Escherichia coli* DH5α/pCR2.1-hOT022T obtained in Reference Example 11 described later has been deposited with the International Patent Organism Depository, National Institute of Advanced Industrial Science and Technology (former designation: NIBH) since Nov. 8, 1999 under the Accession No. FERM BP-6930, and with the Institute for Fermentation, Osaka (IFO) since Oct. 27, 1999 under the Accession No. IFO 16330.

Transformant *Escherichia coli* DH5α/pCR2.1-hOT022G obtained in Reference Example 11 described later has been deposited with the International Patent Organism Depository, National Institute of Advanced Industrial Science and Technology (former designation: NIBH) since Nov. 8, 1999 under the Accession No. FERM BP-6931, and with the Institute for Fermentation, Osaka (IFO) since Oct. 27, 1999 under the Accession No. IFO 16331.

Transformant *Escherichia coli* MM294 (DE3)/pTFCR-FRP-1 obtained in Example A5 described later has been deposited with the International Patent Organism Depository, National Institute of Advanced Industrial Science and Technology (former designation: NIBH) since Sep. 28, 2000 under the Accession No. FERM BP-7313, and with the Institute for Fermentation, Osaka (IFO) since Sep. 19, 2000 under the Accession No. IFO 16476.

Hybridoma IF3 obtained in Reference Example 12 described later which produces anti-rat RFRP-1 monoclonal antibody has been deposited with the International Patent Organism Depository, National Institute of Advanced Industrial Science and Technology (former designation: NIBH) since Feb. 21, 2001 under the Accession No. FERM BP-7463, and with the Institute for Fermentation, Osaka (IFO) since Jan. 16, 2001 under the Accession No. IFO 50527.

EXAMPLES

Hereinbelow, the present invention will be described in more detail with reference to the following Reference Examples and Examples. However, the present invention is not limited to these Reference Examples and Examples. The genetic engineering procedures using *Escherichia coli* were in accordance with those procedures described in the book "Molecular Cloning".

Reference Example 1

Synthesis of cDNA from Human Fetal Brain Poly(A)+ RNA Fraction and Amplification of a cDNA Encoding Physiologically Active Peptide by RT-PCR Oligo dT primer (Gibco BRL) was added to 1 μg of a human fetal brain poly(A)+ RNA fraction purchased from Clontech. Using a reverse transcriptase from Moloney murine leukemia virus (Gibco BRL) and its accompanied buffer, cDNA was synthesized. The reaction product was extracted with phenol:chloroform (1:1), precipitated with phenol and then dissolved in 30 μl of TE. Using 1 μl of the thus prepared cDNA as a template, PCR amplification was carried out with following two primers (F5 and F6).

F5:
5'-GGGCTGCACATAGAGACTTAATTTTAG-3'    (SEQ ID NO: 3)

F6:
5'-CTAGACCACCTCTATATAACTGCCCAT-3'    (SEQ ID NO: 4)

The composition of the reaction solution was as follows: 20 pM each of synthetic DNA primers (F5 and F6), 0.25 mM dNTPs, 0.5 μl of Ex Taq DNA polymerase and 5 μl of its accompanied buffer. The total volume of the reaction solution was 50 μl. For amplification, 40 cycles of 98° C. for 10 sec, 63° C. for 20 sec and 72° C. for 40 sec were performed in a thermal cycler (Perkin Elmer).

Further, using 1 μl of the resultant PCR product as a template, amplification was performed by nested PCR using the following two primers (F1 and R5).

F1:
5'-GCACATAGAGACTTAATTTTAGATTTAGAC-3' (SEQ ID NO: 5)

R5:
5'-CATGCACTTTGACTGGTTTCCAGGTAT-3'    (SEQ ID NO: 6)

The composition of the reaction solution was as follows: 20 pM each of synthetic DNA primers (F1 and R5), 0.25 mM dNTPs, 0.5 μl of Ex Taq DNA polymerase and 5 μl of its accompanied buffer. The total volume of the reacton solution was 50 μl. For amplification, 40 cycles of 98° C. for 10 sec, 60° C. for 20 sec and 72° C. for 40 sec were performed in a thermal cycler (Perkin Elmer). The amplified product was confirmed by 1.2% agarose gel electrophoresis and ethidium bromide staining.

Reference Example 2

Subcloning of the PCR Product into Plasmid Vector and Selection of Candidate Clones for Novel Physiologically Active Peptide by Analysis of the Nucleotide Sequence of the Inserted cDNA The reaction product obtained by PCR in Reference Example 1 was separated using 1.2% agarose gel. Amplification of a DNA fragment of the expected size was confirmed. Then, the DNA was recovered using Quiagen PCR Purification kit (Quiagen). According to the protocol attached to a TA cloning kit (Invitrogen), the recovered DNA was subcloned into plasmid vector pCR™2.1. This plasmid vector was introduced into *E. coli* JM109 competent cells (Takara Shuzo) to prepare transformants. From the resultant transformants, those clones carrying the inserted cDNA fragment were selected in LB agar medium containing ampicillin, IPTG and X-gal. Only those clones presenting a white color were isolated with a sterilized tooth pick to thereby obtain transformant *Escherichia coli* JM109/phRF1.

Each of these clones was cultured overnight in ampicillin-containing LB medium and then plasmid DNA was prepared therefrom using an automated plasmid extraction apparatus (Kurabo). A part of the thus prepared DNA was digested with EcoRI, followed by confirmation of the size of the inserted cDNA fragment. A part of the remaining DNA was treated with RNase, extracted with phenol:chloroform, and then precipitated with ethanol for concentration. Reactions for determining the nucleotide sequence were performed with Dye Deoxy Terminator Cycle Sequencing Kit (ABI), followed by reading with a fluorescence-based automated sequencer. The resultant information about the nucleotide sequence was analyzed using DNASIS (Hitachi System Engineering). The thus determined nucleotide sequence is shown in FIG. 1.

As a result of homology search and sequence analysis based on FIG. 1, it was found that the cDNA fragment inserted into the plasmid carried by transformant *E. coli* JM109/phRF1 encodes a novel, physiologically active peptide.

Reference Example 3

Acquisition of a Splicing Variant of the cDNA Encoding Physiologically Active Peptide from Human Fetal Brain cDNA Using 1 ml of the human fetal brain cDNA prepared in Reference Example 1 as a template, PCR amplification was performed with the following two primers (F5 and hR1).

```
F5:
5'-GGGCTGCACATAGAGACTTAATTTTAG-3'    (SEQ ID NO: 3)

hR1:
5'-CAGCTTTAGGGACAGGCTCCAGGTTTC-3'    (SEQ ID NO: 7)
```

The composition of the reaction solution was as follows: 20 pM each of synthetic DNA primers (F5 and hR1), 0.25 mM dNTPs, 0.5 ml of Ex Taq DNA polymerase and its accompanied buffer. The total volume of the reacton solution was 50 ml. For amplification, 40 cycles of 98° C. for 10 sec, 65° C. for 20 sec and 72° C. for 20 sec were performed in a thermal cycler (Perkin Elmer). The amplified product was confirmed by 1.2% agarose gel electrophoresis and ethidium bromide staining. After the confirmation of amplification of the PCR product, the reaction product was purified with QIA Quick PCR Purification Kit (Quiagen) and then sequenced. Reactions for determining the nucleotide sequence were performed with Big Dye Deoxy Terminator Cycle Sequencing Kit (ABI), followed by reading with a fluorescence-based automated sequencer (ABI377). The resultant information about the nucleotide sequence was analyzed using DNASIS (Hitachi System Engineering). As a result, a cDNA whose 3'-terminal region was different from that of the cDNA obtained in Reference Example 2 was obtained. It was found that this cDNA was a splicing variant of the cDNA obtained in Reference Example 2. The nucleotide sequence determined (SEQ ID NO: 9) and the amino acid sequence deduced therefrom (SEQ ID NO: 8) are shown in FIG. 3.

Reference Example 4

Acquisition of a cDNA Encoding Physiologically Active Peptide from Bovine Hypothalamus Poly(A)⁺ RNA A cDNA encoding a bovine-type physiologically active peptide was obtained from bovine hypothalamus poly(A)⁺ RNA using Marathon cDNA Amplification Kit (Clontech). Briefly, bovine hypothalamus cDNA was prepared according to the manual attached to the kit. Using this cDNA as a template, PCR amplifications were performed with the following four synthetic primers (bF6, bF7, bR6 and bR7) in combination with two accompanied primers AP1 and AP2 to the kit.

```
bF6:
5'-GCCTAGAGGAGATCTAGGCTGGGAGGA-3'    (SEQ ID NO: 10)

bF7:
5'-GGGAGGAACATGGAAGAAGAAAGGAGC-3'    (SEQ ID NO: 11)

bR6:
5'-GATGGTGAATGCATGGACTGCTGGAGC-3'    (SEQ ID NO: 12)

bR7:
5'-TTCCTCCCAAATCTCAGTGGCAGGTTG-3'    (SEQ ID NO: 13)
```

In order to amplify the 5'-terminal (N-terminal) region, the first PCR reaction was performed using two synthetic primers (bR6 and AP1). The reaction solution contained 20 pM each of the primers, 0.25 mM dNTPs, 0.5 ml of Klen Taq DNA Polymerase and the accompanied buffer to the polymerase to make the total volume 25 ml. For amplification, 5 cycles of 98° C. for 10 sec and 72° C. for 2 min; 5 cycles of 98° C. for 10 sec and 70° C. for 2 min; and 25 cycles of 98° C. for 10 sec and 68° C. for 2.5 min were performed in a thermal cycler (Perkin Elmer). Subsequently, the resultant first PCR reaction solution was diluted 10-fold. Using 1 ml of this dilution as a template, the second PCR was performed with primers bR7 and AP2. The reaction solution contained 20 pM each of the primers, 0.25 mM dNTPs, 0.5 ml of Klen Taq DNA Polymerase and the accompanied buffer to the polymerase to make the total volume 25 ml. For amplification, 5 cycles of 98° C. for 10 sec and 72° C. for 2 min; 5 cycles of 98° C. for 10 sec and 70° C. for 2 min; and 35 cycles of 98° C. for 10 sec and 68° C. for 2.5 min were performed in a thermal cycler (Perkin Elmer).

In order to amplify the 3'-terminal (C-terminal) region, the first PCR reaction was performed using two synthetic primers (bF6 and AP1). The reaction solution contained 20 pM each of the primers, 0.25 mM dNTPs, 0.5 ml of Klen Taq DNA Polymerase and the accompanied buffer to the polymerase to make the total volume 25 ml. For amplification, 5 cycles of 98° C. for 10 sec and 72° C. for 2 min; 5 cycles of 98° C. for 10 sec and 70° C. for 2 min; and 25 cycles of 98° C. for 10 sec and 68° C. for 2.5 min were performed in a thermal cycler (Perkin Elmer). Subsequently, the resultant first PCR reaction solution was diluted 10-fold. Using 1 ml of this dilution as a template, the second PCR was performed with primers bF7 and AP2. The reaction solution contained 20 pM each of the primers, 0.25 mM dNTPs, 0.5 ml of Klen Taq DNA Polymerase and the accompanied buffer to the polymerase to make the total volume 25 ml. For amplification, 5 cycles of 98° C. for 10 sec and 72° C. for 2 min; 5 cycles of 98° C. for 10 sec and 70° C. for 2 min; and 35 cycles of 98° C. for 10 sec and 68° C. for 2.5 min were performed in a thermal cycler (Perkin Elmer). Confirmation of the 5'-terminal and 3'-terminal amplified products were performed by 1.2% agarose gel electrophoresis and ethidium bromide staining. After the confirmation of amplification of the PCR products, the reaction products were purified with QIA Quick PCR Purification Kit (Quiagen) and then sequenced. Reactions for determining the nucleotide sequences were performed with Big Dye Deoxy Terminator Cycle Sequencing Kit (ABI), followed by reading with a fluorescence-based automated sequencer (ABI377).

The resultant information about the nucleotide sequence was analyzed using DNASIS (Hitachi System Engineering). The nucleotide sequence determined (SEQ ID NO: 15) and the amino acid sequence deduced therefrom (SEQ ID NO: 14) are shown in FIG. 4.

Reference Example 5

Acquisition of a cDNA Encoding Physiologically Active Peptide from Rat Brain Poly(A)⁺ RNA A cDNA encoding a bovine-type physiologically active peptide was obtained from rat brain poly(A)⁺ RNA using Marathon cDNA Amplification Kit (Clontech). Briefly, rat brain cDNA was prepared according to the manual attached to the kit. Using this cDNA as a template, PCR amplifications were performed with the following two synthetic primers:

```
rLPR1:
5'-CCCTGGGGCTTCTTCTGTCTTCTATGT-3'    (SEQ ID NO: 16)

rLPF1:
5'-AGCGATTCATTTTATTGACTTTAGCA-3'     (SEQ ID NO: 17)
``` in combination with two accompanied primers AP1 and AP2 to the kit.

In order to amplify the 5'-terminal (1-terminal) region, the first PCR reaction was performed using primers rLPR1 and AP1. The reaction solution contained 200 pM each of the primers, 0.1 mM each of dNTPs, 0.25 ml of Klen Taq DNA Polymerase and the accompanied buffer to the polymerase to make the total volume 25 ml. For amplification, 5 cycles of 98° C. for 10 sec and 72° C. for 2 min; 5 cycles of 98° C. for 10 sec and 70° C. for 2 min; and 25 cycles of 98° C. for 10 sec and 68° C. for 2.5 min were performed in a thermal cycler (Perkin Elmer). Subsequently, using the resultant reaction solution as a template, the second PCR was performed with the same primer set used in the first PCR. The composition of the reaction solution was the same as that for the first PCR. For amplification, 5 cycles of 98° C. for 10 sec and 72° C. for 2 min; 5 cycles of 98° C. for 10 sec and 70° C. for 2 min; and 38 cycles of 98° C. for 10 sec (and 68° C. for 2.5 min) were performed in a thermal cycler (Perkin Elmer).

In order to amplify the 3'-terminal (C-terminal) region, the first PCR reaction was performed using primers rLPF1 and AP1. The composition of the reaction solution was the same as that for the amplification of the 5'-terminal (N-terminal region). For amplification, 5 cycles of 98° C. for 10 sec and 72° C. for 2 min; 5 cycles of 98° C. for 10 sec and 70° C. for 2 min; and 25 cycles of 98° C. for 10 sec, 65° C. for 20 sec and 72° C. for 2 min were performed in a thermal cycler (Perkin Elmer). Subsequently, using the resultant first PCR reaction solution as a template, the second PCR was performed with primers rLPF1 and AP2. The composition of the reaction solution was the same as that for the first PCR. For amplification, 5 cycles of 98° C. for 10 sec and 72° C. for 2 min; 5 cycles of 98° C. for 10 sec and 70° C. for 2 min; and 38 cycles of 98° C. for 10 sec, 65° C. for 20 sec and 72° C. for 2 min were performed in a thermal cycler (Perkin Elmer). Confirmation of the 5'-terminal and 3'-terminal amplified products were performed by 1.2% agarose gel electrophoresis and ethidium bromide staining. Bands of PCR product were purified with QIA Quick Gel Extraction Kit (Quiagen) and then sequenced. Determination of the nucleotide sequences was performed in the same manner as described in Reference Example 3. The nucleotide sequence determined (SEQ ID NO: 19) and the amino acid sequence deduced therefrom (SEQ ID NO: 18) are shown in FIG. 5. Further, based on this nucleotide sequence, the following two primers were synthesized near the initiation codon and the stop codon, respectively.

```
ratF2:
5'-AATGGAAATTATTTCATCAAAGCGATT    (SEQ ID NO: 48)

CAT-3' ratR:
5'-CACCTATACTGACAGGAATGATGGCTC    (SEQ ID NO: 49)

TCC-3'
```

From rat hypothalamus poly(A)⁺ RNA, cDNA was synthesized using an AMV reverse transcriptase (Takara Shuzo) and random 9-mer (Takara Shuzo). Using this cDNA as a template, PCR reaction was performed for 33 cycles of 98° C. for 10 sec and 68° C. for 40 sec. Subsequently, using the resultant reaction solution as a template, PCR reaction was performed for 38 cycles of 98° C. for 10 sec and 68° C. for 1 min, to thereby obtain a PCR product of approximately 690 bp. This product was introduced into cloning vector pCR2.1 TOPO according to the manual of TA Cloning Kit (Invitrogen), which was then introduced into *E. coli* JM109 to thereby obtain transformant *E. coli* JM109/prLPL6. The nucleotide sequence was determined in the same manner as in Reference Example 3 (SEQ ID NO: 51), and the amino acid sequence was deduced therefrom (SEQ ID NO: 50).

Reference Example 6

Acquisition of a cDNA Encoding Mouse-Type Physiologically Active Peptide from Mouse Brain Poly(A)⁺ RNA by Marathon PCR and Confirmation of Its Sequence In order to obtain a cDNA encoding a mouse-type physiologically active peptide, first, 1 µg of mouse brain poly(A)⁺ RNA was reacted with SuperScriptII RNase H-reverse transcriptase (GIBCO BRL) in the presence of 2.5 pmol of oligo d(T) primers (Takara Shuzo), 0.5 mM dNTPs and 10 mM DTT at 42° C. for 1 hr to synthesize cDNA. Using this cDNA as a template, PCR amplification was performed with the following primers:

```
FF2:
5'-GACTTAATTTTAGATTTAGACAAAATGG   (SEQ ID NO: 26)
AA-3' rR4:
5'-TTCTCCCAAACCTTTGGGGCAGGTT-3'   (SEQ ID NO: 27)
``` and Klen Taq DNA polymerase (Clontech) for 39 cycles of 98° C. for 10 sec, 56° C. for 20 sec and 72° C. for 25 sec. Further, using the same primer set, PCR reaction was performed for 25 cycles of 98° C. for 10 sec, 60° C. for 20 sec and 72° C. for 25 sec. The resultant product was detected by 2% agarose gel electrophoresis and ethidium bromide staining. The band was purified with QIA Quick Gel Extraction Kit (Qiagen) and then sequenced in the same manner as in Reference Example 3. In order to obtain the 5'-terminal and 3'-terminal sequences to the resultant cDNA fragment encoding a mouse-type physiologically active peptide, cDNA was synthesized from 1 µg of mouse brain poly(A)⁺ RNA using Marathon cDNA Amplification Kit (Clontech) in the same manner as in Reference Example 5 to thereby prepare a template. The following three primers:

```
mF1:
5'-ACAGCAAAGAAGGTGACGGAAAATACTC-3'  (SEQ ID NO: 28)

mF3:
5'-ATAGATGAGAAAAGAAGCCCCGCAGCAC-3'  (SEQ ID NO: 29)

mR1:
5'-GTGCTGCGGGGCTTCTTTTCTCATCTAT-3'  (SEQ ID NO: 30)
``` were synthesized and used in combination with the accompanied primer AP1 to the kit to perform PCR reactions.

In order to amplify the 5'-terminal (N-terminal) region, the first PCR reaction was performed using primers mR1 and AP1. For the amplification of the 3'-terminal (C-terminal) region, the first PCR reaction was performed using primers mF1 and AP1. The reaction solution contained 200 pM each of the primers, 0.1 mM each of dNTPs, 0.25 ml of Klen Taq DNA Polymerase and the accompanied buffer to the polymerase to make the total volume 25 ml. For amplification, 5 cycles of 98° C. for 10 sec and 72° C. for 2 min; 5 cycles of 98° C. for 10 sec and 70° C. for 2 min; and 25 cycles of 98° C. for 10 sec and 68° C. for 2.5 min were performed. Subsequently, using the first PCR reaction solution as a template, the second PCR was performed. The amplification of the 5'-terminal region was performed with the same primer set as used for the first PCR. The amplification of the 3'-terminal region was performed with primers mF3 and AP1. The composition of the reaction solution was the same as in the reaction solution for the first PCR. For amplification, 5 cycles of 98° C. for 10 sec and 72° C., for 2 min; 5 cycles of 98° C. for 10 sec and 70° C. for 2 min; and 38 cycles of 98° C. for 10 sec and 68° C. for 2.5 min were performed.

Confirmation of the 5'-terminal and 3'-terminal amplified products were performed by 1.2% agarose gel electrophoresis and ethidium bromide staining. PCR product bands were purified with QIA Quick Gel Extraction Kit (Quiagen) and then sequenced. Determination of the nucleotide sequence was performed in the same manner as described in Reference Example 3. Further, based on the resultant nucleotide sequence, the following two primers were synthesized.

```
moF:
5'-TTTAGACTTAGACGAAATGGA-3'   (SEQ ID NO: 31)

moR:
5'-GCTCCGTAGCCTCTTGAAGTC-3'   (SEQ ID NO: 32)
```

Using these primers and, as a template, the above-described cDNA synthesized from mouse brain poly(A)⁺ RNA with SuperScript II RNase H— reverse transcriptase, PCR reaction was performed to amplify a fragment containing the fill-length cDNA encoding a mouse-type physiologically active peptide. The reaction was carried out with Klen Taq DNA polymerase (Clontech) under the conditions of 35 cycles of 98° C. for 10 sec, 56° C. for 20 sec and 72° C. for 15 sec. The amplified product of approximately 600 bp was detected by 2% agarose gel electrophoresis and ethidium bromide staining. The band was purified with QIA Quick Gel Extraction Kit (Qiagen) and sub-cloned into cloning vector pCR2.1-TOPO (TOPO TA cloning kit; Invitrogen), which was then introduced into *E. coli* JM109 to thereby obtain transformant *E. coli* JM109/pmLP4. The nucleotide sequence was determined in the same manner as in Reference Example 3. The nucleotide sequence determined (SEQ ID NO: 34), and the amino acid sequence deduced therefrom (SEQ ID NO: 33) are shown in FIG. 7.

Reference Example 7

(1) Cloning of a cDNA Encoding G Protein-Coupled Receptor Protein from the Peripheral Area of Rat Brainstem and Determination of the Nucleotide Sequence thereof Using cDNA from the peripheral area of rat brainstem as a template, PCR reaction was performed with primer 1 (SEQ ID NO: 35) and primer 2 (SEQ ID NO: 36). The composition of the reaction solution was as follows: ¹/₁₀ volume of the above cDNA as a template, ¹/₅₀ volume of Advantage cDNA Polymerase Mix (Clontech), 0.2 µM each of primer 1 (SEQ ID NO: 35) and primer 2 (SEQ ID NO: 36), 200 µM dNTPs, and the accompanied buffer to the polymerase to make the reaction solution 50 µl. Thermal conditions of the PCR were as follows: (i) 94° C. for 2 min, then (ii) 3 cycles of 94° C. for 30 sec and 72° C. for 2 min, (iii) 3 cycles of 94° C. for 30 sec and 68° C. for 2 min, (iv) 30 cycles of 94° C. for 30 sec, 64° C. for 30 sec and 68° C. for 2 min, and finally (v) extension at 68° C. for 8 min. The resultant PCR product was sub-cloned into plasmid vector pCR2.1 (Invitrogen) according to the protocol attached to TA cloning kit (Invitrogen). This vector was introduced into *E. coli* DH5α. From the resultant transformants, those clones carrying the cDNA were selected in ampicillin-containing LB agar medium. As a result of analysis of the nucleotide sequences of individual clones, a cDNA sequence encoding a novel G protein-coupled receptor protein was obtained (SEQ ID NO: 38). A novel G protein-coupled receptor protein comprising the amino acid sequence (SEQ ID NO: 37) deduced from this cDNA sequence was designated rOT7T022L.

Plasmid pAK-rOT022L into which the cDNA (SEQ ID NO: 38) encoding the G protein-coupled receptor protein rOT7T022L of the invention derived from the peripheral area of rat brainstem had been sub-cloned was introduced into *Escherichia coli* DH10B to thereby obtain transformant *Escherichia coli* DH10B/rOT7T022L.

(2) Establishment of G Protein-Coupled Receptor Protein rOT7T022L-Expressing CHO Cells CHO dhfr⁻ cells ($1 \times 10^6$) were plated in a 10 cm tissue culture plate and cultured for 24 hr. Using 20 μg of the rOT7T022L expression vector obtained in (1) above and a gene transfer kit (Gen Transfer: Nippon Gene) utilizing the liposome method, a DNA/liposome complex was formed. The medium was exchanged for fresh medium, to which the DNA/liposome complex was added and incubated overnight. After exchange of the medium for fresh medium, cells were cultured further for one day. Then, the medium was changed for a transformant selection medium, and cells were cultured for two days in this medium. Further, cells were treated with trypsin-EDTA and recovered from the tissue culture plate, and cells were re-cultured under a state of extremely low cell density in order to increase the ratio of transformants. As a result, a cell clone CHO-rOT7T022L that expresses rOT7T022L highly and stably was obtained.

(3) Synthesis of Met-Pro-His-Ser-Phe-Ala-Asn-Leu-Pro-Leu-Arg-Phe-$NH_2$ (SEQ ID NO: 39)

Commercial p-methyl BHA resin (Applied Biosystems; current Perkin Elmer) (0.5 mmole) was placed in a reactor in a peptide synthesizer (Applied Biosystems Model 430A), and swollen with DCM. Then, the first amino acid Boc-Phe was activated by the HOBt/DCC method and introduced into the p-methyl BHA resin. Subsequently, the resin was treated with 50% TFA/DCM to remove the Boc group to thereby liberate the amino group, and then neutralized with DIEA. The subsequent amino acid Boc-Arg (Tos) was condensed with this amino group by the HOBt/DCC method. The presence or absence of unreacted amino groups was examined by a ninhydrin test When the completion of the reaction was confirmed, Boc-Leu, Boc-Pro, Boc-Leu, Boc-Asn, Boc-Ala, Boc-Phe, Boc-Ser(Bzl), Boc-His(Bom), Boc-Pro and Boc-Met were condensed in succession in the same manner as described above.

The resin into which the entire sequence of the amino acids had been introduced was treated with 50% TFA/DCM to remove the Boc groups on the resin, and then dried. As a result, 0.73 g of Met-Pro-His(Bom)-Ser(Bzl)-Phe-Ala-Asn-Leu-Pro-Leu-Arg(Tos)-Phe-pMBHA-resin (SEQ ID NO: 39) was obtained.

In a hydrogen fluoride reactor made of Teflon, 0.25 g of this resin was reacted with 5.1 g of p-cresol and 15 ml of hydrogen fluoride at 0° C. for 60 minutes. The hydrogen was distilled off under reduced pressure. The residue was diluted with 100 ml of diethyl ether, stirred, filtered through a glass filter, and the fraction on the filter was dried. This fraction was suspended in 50 ml of 50% aqueous solution of acetic acid and stirred to extract the peptide. After the extraction, the resin was separated and the peptide was concentrated under reduced pressure to about 5 ml. This peptide was applied to a Sephadex G-25 column (2×90 cm). Development was carried out with 50% aqueous acetic acid solution, and major fractions were collected and lyophilized. Subsequently, this crude peptide was dissolved in 1.5 ml of 5% thioglycollic acid/50% acetic acid and retained at 50° C. for 12 hr to reduce the Met-oxidant peptide. Then, the peptide was applied to a reversed phase column packed with LiChroprep RP-18 (Merck) and repeatedly purified by gradient elution using 0.1% TFA/$H_2O$ and 0.1% TFA-containing 33% acetonitrile/$H_2O$. Those fractions eluted at the acetonitrile concentration of around 27% were pooled and lyophilized to obtain 26 mg of white powder.

$(M+H)^+$ value by mass spectrometry: 1428.7 (theoretical value: 1428.8)

HPLC elution time: 18.0 min

Column conditions:
    Column: Wakosil 5C18 (4.6×100 mm)
    Eluent: A (0.1% TFA-containing 5% acetonitrile/$H_2O$)
    B (0.1% TFA-containing 55% acetonitrile/$H_2O$)
    Linear gradient elution from A to B (25 min.)
    Flow rate: 1.0 ml/min (4) Synthesis of Val-Pro-Asn-Leu-Pro-Gln-Arg-Phe-$NH_2$ (SEQ ID NO: 40)

Boc-Phe, Boc-Arg(Tos), Boc-Gln, Boc-Pro, Boc-Leu, Boc-Asn, Boc-Pro and

Boc-Val were condensed in succession in the same manner as described in (3) in Reference Example 7, to thereby obtain 0.43 g of Boc-Val-Pro-Asn-Leu-Pro-Gln-Arg(Tos)-Phe-pMBHA-resin (SEQ ID NO: 40). This resin (0.22 g) was treated with hydrogen fluoride and purified by column chromatography in the same manner as described above to thereby obtain 46 mg of desired white powder.

$(M+H)^+$ value by mass spectrometry: 969.5 (theoretical value: 969.6)

HPLC elution time: 11.8 min

Column conditions:
    Column: Wakosil 5C18(4.6×1001 mm)
    Eluent: A (0.1% TFA-containing 5% acetonitrile/$H_2O$)
    B (0.1% TFA-containing 55% acetonitrile/$H_2O$)
    Linear gradient elution from A to B (25 min.)
    Flow rate: 1.0 ml/min (5) Synthesis of Ser-Ala-Gly-Ala-Thr-Ala-Asn-Leu-Pro-Arg-Ser-$NH_2$ (SEQ ID NO: 41)

Boc-Ser(Bzl), Boc-Arg(Tos), Boc-Leu, Boc-Pro, Boc-Leu, Boc-Asn, Boc-Ala, Boc-Thr(Bzl), Boc-Ala, Boc-Gly, Boc-Ala and Boc-Ser(Bzl) were condensed in succession in the same manner as described in (3) in Reference Example 7, to thereby obtain 0.62 g of Boc-Ser(Bzl)-Ala-Gly-Ala-Thr(Bzl)-Ala-Asn-Leu-Pro-Leu-Arg(Tos)-Ser(Bzl)-pM-BHA-resin (SEQ ID NO: 41). This resin (0.23 g) was treated with hydrogen fluoride and purified by column chromatography in the same manner as described above to thereby obtain 71 mg of desired white powder.

$(M+H)^+$ value by mass spectrometry: 1156.4 (theoretical value: 1156.6)

HPLC elution time: 11.8 mm

Figure 2:
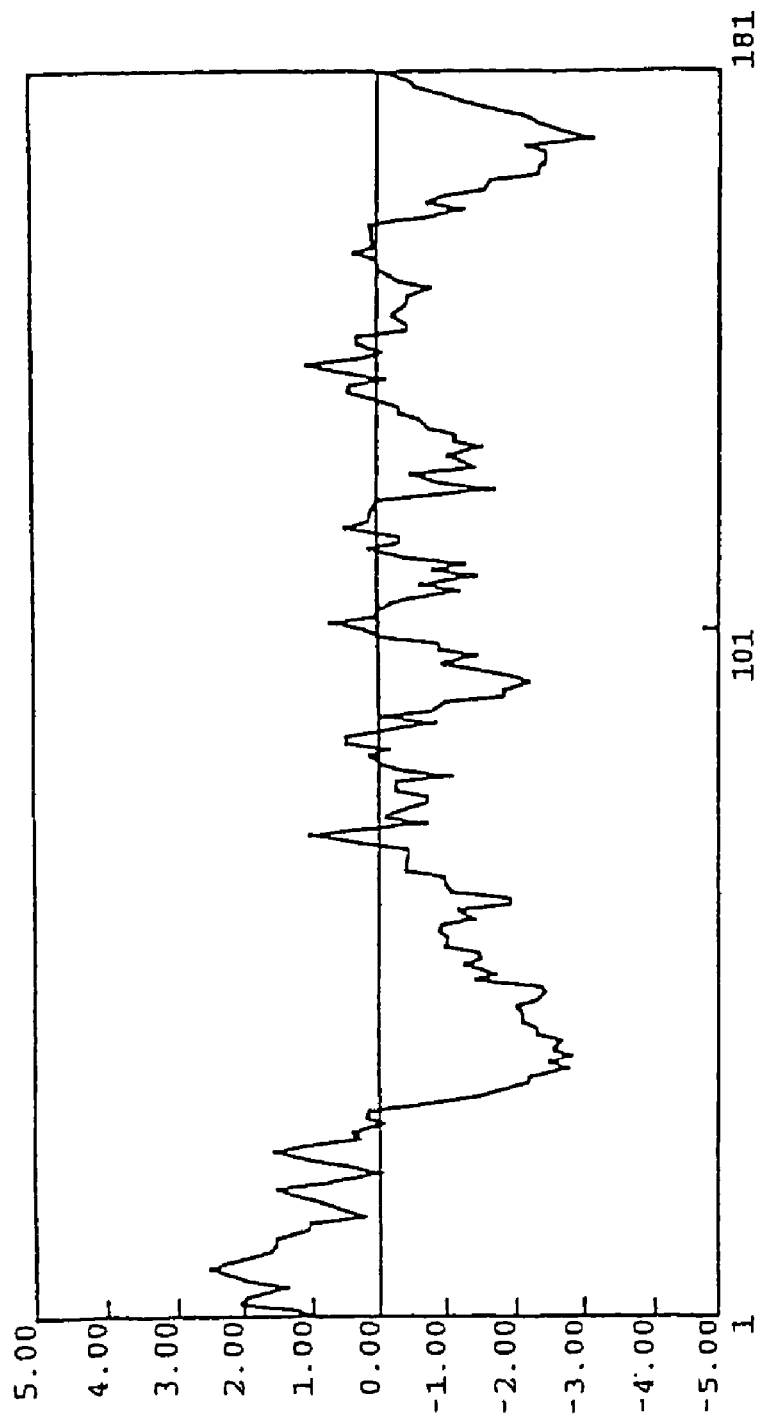
FIG. 2 is a chart showing the hydrophobic plot of the polypeptide of the present invention.
Figure 8:
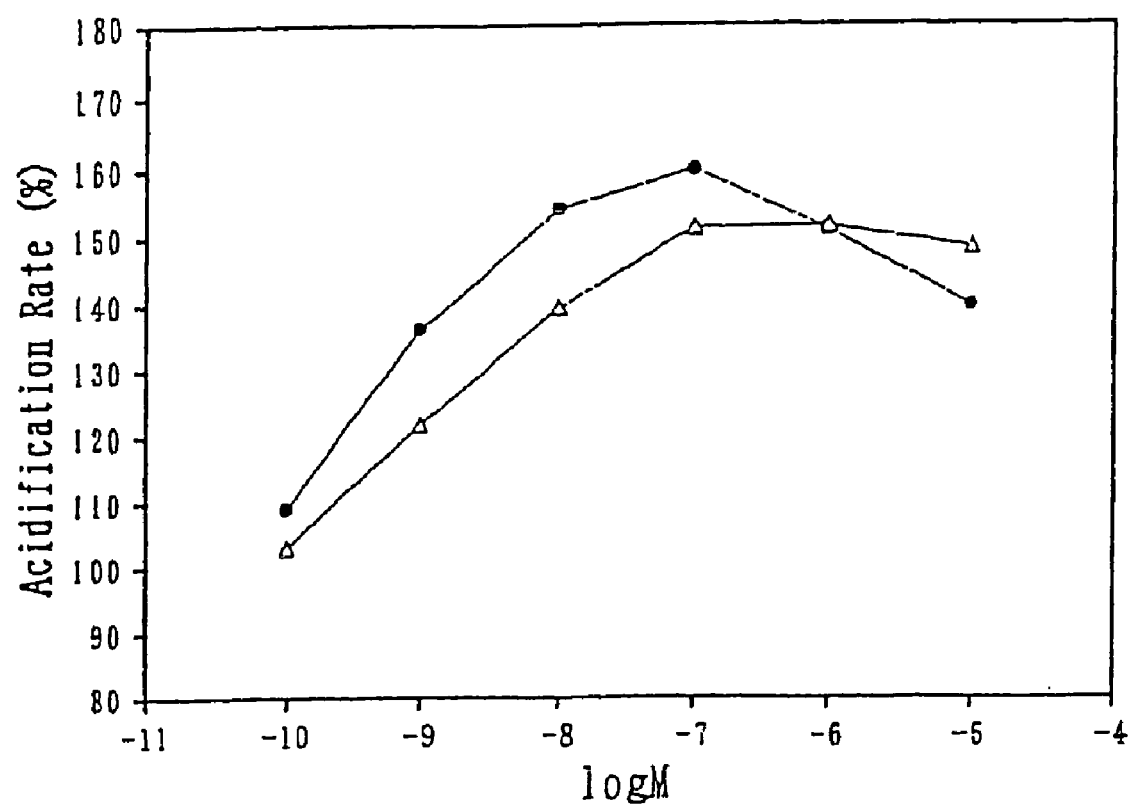
FIG. 8 shows the figure which shows the reactivity of peptides to rOT7T022L receptor-expressing CHO cells examined with a cytosensor in Reference Example 7. In this Figure, ●—● represents MPHSFANLPLRF amide (SEQ ID NO: 39) and Δ—Δ represents VPNLPQRF amide (SEQ ID NO: 40).

Column conditions:
    Column: Wakosil 5C18 (4.6×100 mm)
    Eluent: A (0.1% TFA-containing 5% acetonitrile/$H_2O$)
    B (0.1% TFA-containing 55% acetonitrile/$H_2O$)
    Linear gradient elution from A to B (25 min.)
    Flow rate: 1.0 ml/min (6) Reaction Experiment Between rOT7T022L (SEQ ID NO: 37) and Peptide MPHSFANLPLRF Amide (SEQ ID NO: 39) and Between rOT7T022L and Peptide VPNLPQRF Amide (SEQ ID NO: 40) Using a Cytosensor The rOT7T022L receptor-expressing CHO cells obtained in (2) in Reference Example 7 were sown in cytosensor capsules at $2.7 \times 10^5$ cells/capsule. After overnight culture, the capsules were mounted in the work station of a cytosensor. The assay medium (0.1% bovine serum albumin-containing low buffered RPMI1640 medium) positioned in the flow route of the cytosensor was supplied to the cells under pump ON (80 sec)/pump OFF (40 sec) cycles. In each cycle, the change ratio of extracellular pH for 30 sec starting from 8 sec after the stop of the pump was calculated as acidification rate. The time course of acidification rate was monitored. When this rate began to show stable values, the flow route was shifted to thereby expose individual peptide to the cells for 7 min and 2 sec. The values of acidification rate in individual wells were normalized taking the values for the 3 cycles immediately before the peptide exposure as 100%. Comparison of the reactions of the cells revealed that rOT7T022L receptor-expressing CHO cells were reactive with peptide MPHSFANLPLRF amide (SEQ ID NO: 39) and peptide VPNLPQRF amide (SEQ ID NO: 40) in a strongly dose dependent manner (FIG. 8).

Reference Example 8

Preparation of Transformant Carrying a Candidate Splicing Variant cDNA Encoding a Human Novel Physiologically Active Peptide The reaction product obtained in the PCR performed in Reference Example 3 above was separated with 1.2% agarose gel to thereby confirm the amplification of a DNA fragment of the expected size. Then, the DNA was recovered with Qiagen PCR Purification Kit (Quiagen). According to the protocol attached to a TA cloning kit (Invitrogen), the recovered DNA was subcloned into plasmid vector pCR™2.1. This plasmid vector was introduced into *E. coli* JM109 competent cells (Takara Shuzo) to prepare transformants. From the resultant transformants, those clones carrying the inserted cDNA fragment were selected in LB agar medium containing ampicillin, IPTG and X-gal. Only those clones presenting a white color were isolated with a sterilized tooth pick. Each of these clones was cultured overnight in ampicillin-containing LB medium and then plasmid DNA was prepared therefrom using an automated plasmid extraction apparatus (Kurabo). A part of the thus prepared DNA was digested with EcoRI, followed by confirmation of the size of the inserted cDNA fragment. A part of the remaining DNA was treated with RNase, extracted with phenol:chloroform, and then precipitated with ethanol for concentration. Reactions for determining the nucleotide sequence were performed with Dye Deoxy Terminator Cycle Sequencing Kit (ABI), followed by reading with a fluorescence-based automated sequencer. As a result, transformant *Escherichia coli* JM109/phRF2 was obtained.

Reference Example 9

Preparation of Transformant Carrying a cDNA Encoding Bovine Novel Physiologically Active Peptide Using 1 ml of the bovine hypothalamus cDNA prepared in Reference Example 4, PCR amplification was performed with the following two primers bFF and bFR.

bFF:
5'-TTCTAGATTTTGGACAAAATGGAAATT-3' (SEQ ID NO: 52)

bFR:
5'-CGTCTTTAGGGACAGGCTCCAGATTTC-3' (SEQ ID NO: 53)

The composition of the reaction solution was as follows: 20 pM each of synthetic primers (bFF and bFR), 0.25 mM dNTPs, 0.5 ml of Ex Taq DNA polymerase and the accompanied buffer to the polymerase to make the reaction solution 50 ml. The amplification was performed in a thermal cycler (Perkin Elmer) under the following conditions: 40 cycles of 98° C. for 10 sec, 65° C. for 20 sec and 72° C. for 20 sec. The amplified product was confirmed by 1.2% agarose gel electrophoresis and ethidium staining. The reaction product obtained in the PCR performed in Reference Example 3 above was separated with 1.2% agarose gel to thereby confirm the amplification of a DNA fragment of the expected size. Then, the DNA was recovered with Qiagen PCR Purification Kit (Quiagen). According to the protocol attached to a TA cloning kit (Invitrogen), the recovered DNA was subcloned into plasmid vector pCR™2.1. This plasmid vector was introduced into *E. coli* JM109 competent cells (Takara Shuzo) to prepare transformants. From the resultant transformants, those clones carrying the inserted cDNA fragment were selected in LB agar medium containing ampicillin, IPTG and X-gal. Only those clones presenting a white color were isolated with a sterilized tooth pick. Each of these clones was cultured overnight in ampicillin-containing LB medium and then plasmid DNA was prepared therefrom using an automated plasmid extraction apparatus (Kurabo). A part of the thus prepared DNA was digested with EcoRI followed by confirmation of the size of the inserted cDNA fragment. Further, the prepared DNA was treated with RNase, extracted with phenol:chloroform, and then precipitated with ethanol for concentration. Reactions for determining the nucleotide sequence were performed with Dye Deoxy Terminator Cycle Sequencing Kit (ABI), followed by reading with a fluorescence-based automated sequencer. As a result, transformant *Escherichia coli* JM109/pbRF2 was obtained.

Reference Example 10 cAMP Production Inhibitory Effects of Peptide MPHSFANLPLRF amide (SEQ ID NO: 39) and Peptide VPNLPQRF Amide (SEQ ID NO: 40) Upon rOT7T022L (SEQ ID NO: 37)-Expressing CHO Cells The experiment using a cytosensor conducted in (6) in Reference Example 7 confirmed that peptides MPHSFANLPLRF amide (SEQ ID NO: 39) and VPNLPQRF amide (SEQ ID NO: 40) synthesized in (3) and (4) in Reference Example 7, respectively, react with rOT7T022L receptor specifically. Subsequently, the cAMP production inhibitory effects of these peptides upon rOT7T022L-expressing CHO cells were measured.

The rOT7T022L-expressing CHO cells obtained in (2) in Reference Example 7 were plated in 24-well plated at $1.0 \times 10^5$ cells/well and cultured at 37° C. for 2 days. Cells were washed with Hanks' buffer supplemented with 0.05% BSA and 0.2 mM IBMX, and then left in the same buffer at 37° C. for 30 min. Thirty minutes later, an assay buffer (the above-mentioned buffer to which $10^{-6}$ M forskolin is added) and the above-mentioned peptides at varied concentrations were added to the cells, followed by incubation at 37° C. for 30 min.

Figure 9:
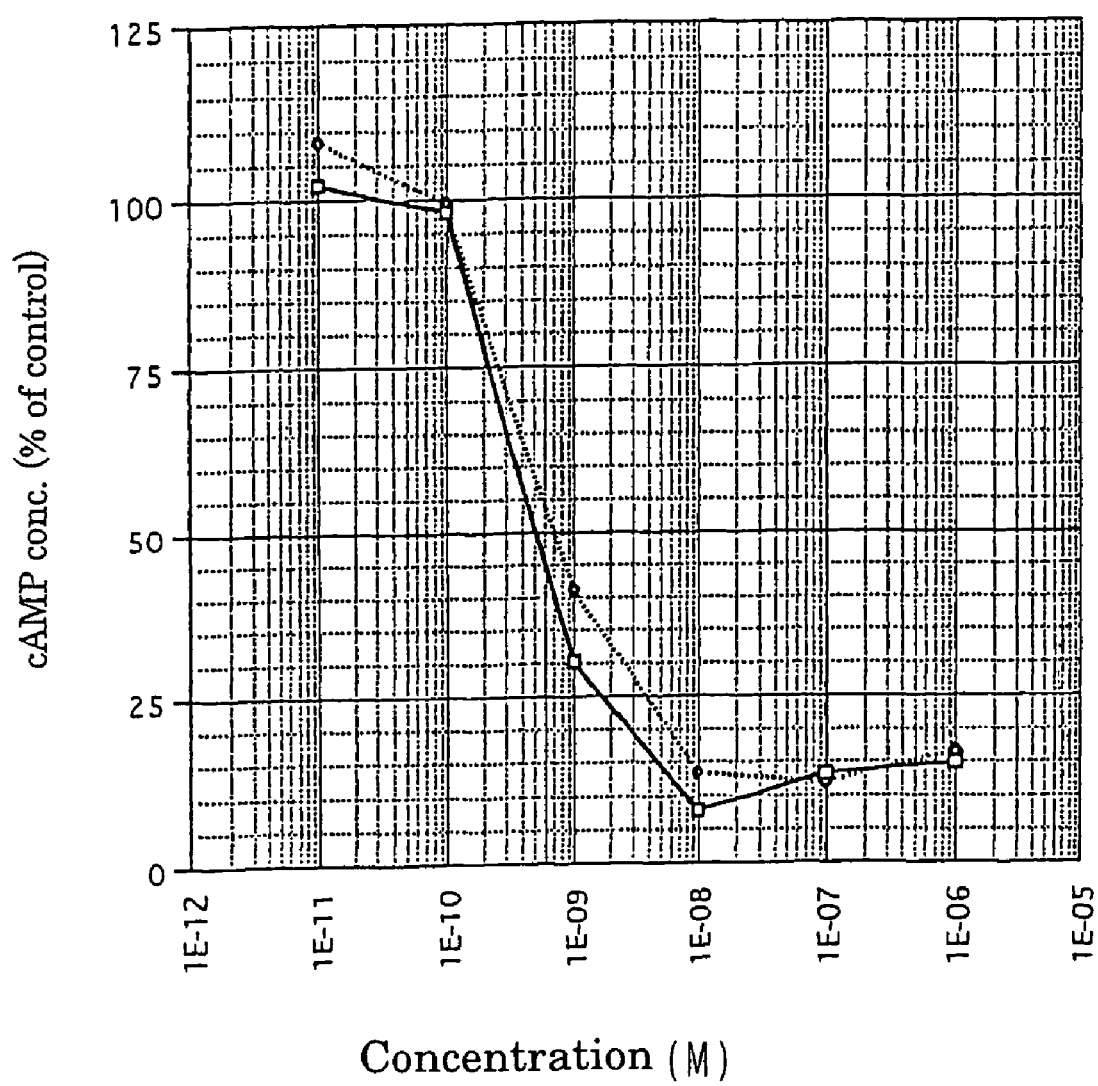
FIG. 9 shows the figure which shows cAMP production inhibitory activity of MPHSFANLPLRFamide (SEQ ID NO: 39) and VPNLPQRFamide (SEQ ID NO: 40) to rOT7T022L-expressing CHO cells examined in Reference Example 10. In this Figure, □—□ represents MPHSFANLPLRFamide (SEQ ID NO: 39) and ●—● represents VPNLPQRF amide (SEQ ID NO: 40).

Thirty minutes later, intracellular cAMP concentrations in individual wells were measured according to the protocol attached to the cAMP EIA Kit (Amersham). As a result, as shown in FIG. 9, peptides MPHSFANLPLRF amide (SEQ ID NO: 39) and VPNLPQRF amide (SEQ ID NO: 40) revealed cAMP production inhibitory effects upon rOT7T022L receptor-expressing CHO cells. The $IC_{50}$ values were 0.5 nM and 0.7 nM, respectively; thus, these peptides revealed strong effects at very low concentrations.

Reference Example 11

(1) Cloning of a cDNA Encoding G Protein-Coupled Receptor Protein from Human Hypothalamus and Determination of the Nucleotide Sequence Thereof PCR reaction was performed using human hypothalamus cDNA (Clontech) as a template and the following two primers: primer 1: 5'-GTCGACATGG AGGGGGAGCC CTCCCAGCCT C-3' (SEQ ID NO: 57) and primer 2: 5'-ACTAGTTCAG ATATCCCAGG CTGGAATGG-3' (SEQ ID NO: 58). The composition of the reaction solution was as follows: 1/10 volume of the above-mentioned cDNA as a template, 1/50 volume of Advantage-HF Polymerase Mix (Clontech), 0.2 µM each of primer 1 (SEQ ID NO: 57) and primer 2 (SEQ ID NO: 58), 200 µM dNTPs, 4% dimethyl sulfoxide, and the accompanied buffer to the polymerase to make the reaction solution 25 µl. Thermal conditions of the PCR were as follows: (i) 94° C. for 2 min, then (ii) 3 cycles of 94° C. for 20 sec and 72° C. for 1.5 min, (iii) 3 cycles of 94° C. for 20 sec and 67° C. for 1.5 min, (iv) 38 cycles of 94° C. for 20 sec., 62° C. for 20 sec and 72° C./68° C. for 1.5 min, and finally (v) extension at 68° C. for 7 min. The resultant PCR product was sub-cloned into plasmid vector pCR2.1 (Invitrogen) according to the protocol attached to TA cloning kit (Invitrogen). This vector was introduced into E. coli DH5α. From the resultant transformants, those clones carrying the cDNA were selected in ampicillin-containing LB agar medium. As a result of analysis of the nucleotide sequences of individual clones, cDNA sequences encoding a novel G protein-coupled receptor protein were obtained (SEQ ID NOS: 55 and 56). Although these two sequences are different from each other in one nucleotide at position 597, amino acid sequences deduced therefrom are the same (SEQ ID NO: 57). A novel G protein-coupled receptor protein comprising this amino acid sequence was designated hOT7T022. The two transformants were designated Escherichia coli DH5 α/pCR2.1-hOT022T (carrying the cDNA represented by SEQ ID NO: 55) and Escherichia coli DH5α/pCR2.1-hOT022G (carrying the cDNA represented by SEQ ID NO: 56), respectively.

Reference Example 12

Preparation of Anti-Rat RFRP-1 Monoclonal Antibody

A monoclonal antibody was prepared against a peptide C-VPHSAANLPLRF-NH$_2$ as an antigen; this peptide represents the C-terminal 12 amino acids of rat-type RFRP-1 (the C-terminal carboxyl group is amidated: an amino acid sequence which is from position 83 (Val) to position 94 (Phe) of the amino acid sequence of SEQ ID NO: 50) to which one Cys residue is added at the N-terminus. The antigen peptide (0.6 mg) was conjugated with bovine serum albumin (BSA) using maleimide. The resultant conjugate (100 µg) was subcutaneously injected into mice three times to immunize them. Then, 50 µg of the conjugate was injected into the tail vein as final immunization. Four days after the final immunization, splenocytes were recovered from each mouse and fused to mouse myeloma cells (P3-X63Ag8-U1; Matsumoto et al, BBRC (1999) vol. 257, 264–268) using polyethylene glycol. After this cell fusion, a hybridoma cell 1F3 was selected and cultured in a large quantity using INTREGRA CL-1000 to thereby obtain a culture supernatant of IF3. From this culture supernatant, anti-rat RFRP-1 monoclonal antibody was obtained using HiTrap rProtein A column (Pharmacia). Isotyping of this monoclonal antibody with Mouse mAb Isotyping Kit (Amersham) revealed that the subtype of this monoclonal antibody was IgG1 κ chain.

Reference Example 13

Construction of Competitive EIA

First, the peptide used as the antigen in Reference Example 12 was conjugated with horse radish peroxidase (HRP) using maleimide to thereby prepare a conjugate HRP-rat RFRP-1. Then, using this conjugate HRP-rat RFRP-1 and the anti-rat RFRP-1 monoclonal antibody obtained in Reference Example 12, a competitive EIA was constructed.

Briefly, 50 µl of the anti-rat RFRP-1 monoclonal antibody diluted with a buffer (phosphate buffered saline (PBS) containing 2 mM EDTA, 0.4% BSA, 0.1 M NaCl and 0.1% micro-O-protect) was added to each well of 96-well plates coated with anti-mouse IgGAM (Cappel) at 1.5 µg/well and blocked with Block ACE (Dainippon Pharmaceutical). A 50 ml sample dissolved in the same buffer was also added to each well. After a 16-hr incubation at 4° C., 50 µl of HRP-rat RFRP-1 diluted with the buffer was added to each well. After 2-hr incubation at room temperature, the plates were washed with 0.1% Tween 20 (Sigma)-containing PBS. Then, the activity of HRP bound to each well was detected by a color reaction using TMB microwell peroxidase system (Kirkegaard & Perry Labs), followed by measurement of the absorbance at 450 nm. Changes in absorbance when RFRP-1-related peptides were added are shown in FIG. 11.

Example A1

Effects of Ligand Peptide upon Plasma Pituitary Hormone Levels

Effects of the administration of the peptide represented by SEQ ID NO: 39 into the third ventricle upon pituitary hormone levels were examined. Briefly, adult male Wistar rats (body weight: 290–350 g at the time of surgery) were anesthetized by intraperitoneal administration of 50 mg/kg pentobarbital and fixed in a stereotaxic apparatus for rat brain. The incisor bar was set 3.3 mm below the interaural line. The skull surface was exposed and a hole was drilled in the skull with a dental drill in order to implant a guide cannula Further, an anchor screw was embedded at one place around the hole. A stainless guide cannula AG-12 (inside dia. 0.4 mm, outside dia. 0.5 mm; Eicom) was inserted so that its tip is located above the third ventricle. The stereotaxic coordinates were set as follows according to the atlas of Paxinos and Watson (1998): AP: +7.2 mm (from the interaural line), L: 0.0 mm, H: +2.0 mm (from the interaural line). The guide cannula was fixed onto the skull with instant glue, dental cement and the anchor screw. A stainless dummy cannula AD-12 (outside dia. 0.35 mm; Eicom) was inserted into the guide cannula and fixed with a cap nut (Eicom). After the surgery, the rats were bred separately in individual cages for more than one week to allow recovery.

The day before the experiment, the rats that had undergone the above surgery were anesthetized by intraperitoneal administration of 50 mg/kg pentobarbital and fixed on anatomical pads in face-up position. Then, a catheter (SP35; Natsume Seisakusho) was inserted into the right jugular vein. The next day, 400 µl of blood was taken from the jugular vein. In order to prevent blood coagulation, 20 µl of physiological saline containing 200 units/ml heparin was put in advance in the injection syringe. The cap nut and the dummy cannula installed on the rat skull were removed. Instead of them, a stainless microinjection cannula AMI13 (inside dia. 0.17 mm, outside dia. 0.35 mm; Eicom) connected with a Teflon tube (length 50 cm, inside dia. 0.1 mm, outside dia. 0.4 mm; Eicom) was inserted into the guide cannula. The length of the microinjection cannula was adjusted in advance so that 1 mm of its tip is exposed from the guide cannula. One end of the Teflon tube was connected with a microsyringe pump. Then, a total 10 µl of PBS alone or PBS containing the peptide represented by SEQ ID NO: 39 was injected into the third ventricle at a flow rate of 5 µl/min. One minute after the completion of the injection, the microinjection cannula was removed, and a dummy cannula was fixed again with a cap nut. A 400 µl blood sample was taken from the cannula inserted into the jugular vein immediately before the start of the intraventricular administration and at 10, 20, 30, 40 and 60 min after the start of the intraventricular administration. The collected blood was centrifuged at 5,000 rpm for 10 min in a high-speed refrigerated microcentrifuge (MR-150; Tomy Seiko) to recover the supernatant (plasma). The prolactin levels in the plasma were measured by radioimmunoassay.

Figure 10:
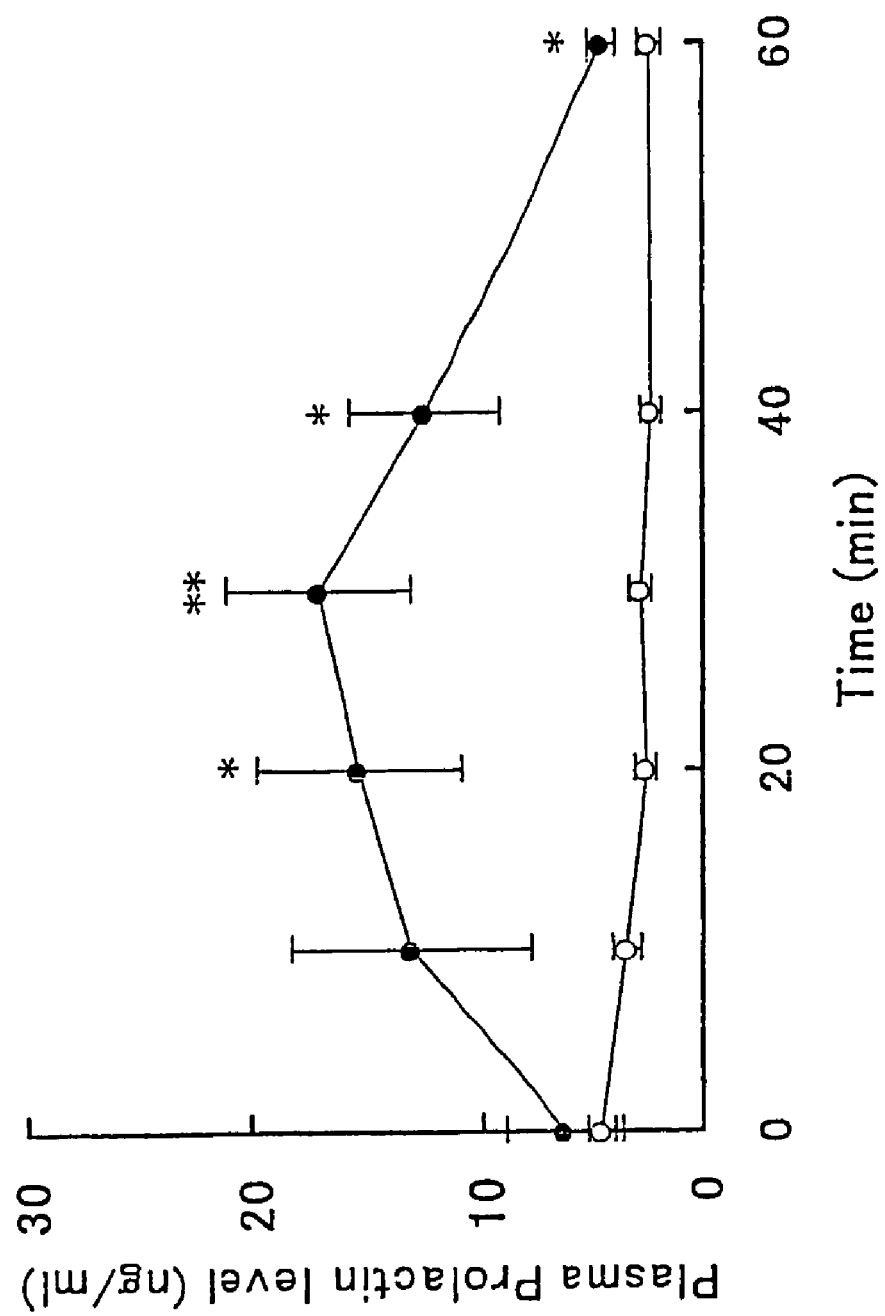
FIG. 10 shows the measurement result of the level of the plasma prolactin determined in Example A1. In this Figure, ●—● represent the prolactin levels of the group to which the peptide represented by SEQ ID NO: 39 was administered in PBS; ○—○ represent the prolactin levels of the control group to which PBS alone was administered.

The results are expressed as mean±S.E.M. Whether there is a significant difference between the group to which PBS containing the peptide represented by SEQ ID NO: 39 was administered and the control group to which PBS alone was administered was tested by Student's t-test. Differences were assessed with two-sided tests, and significance level 5% or below was judged statistically significant. As shown in FIG. 10, plasma prolactin levels showed an increasing tendency from 10 min after the administration of 10 mnol peptide represented by SEQ ID NO: 39 into the third ventricle; the levels increased significantly at 20, 30 and 40 min after the administration. Even 60 min after the administration, significant difference was observed between the administration group and the control group. The GH, LH, ACTH and TSH levels in the plasma did not show significant changes.

Example A2

Purification of Endogenous RFRP-1 from Bovine Hypothalamus

RFRP-1-like immune activity was found in a crude peptide fraction from bovine hypothalamus in the competitive EIA constructed in Reference Example 13. Using this RFRP-1-like immune activity as an indicator, an endogenous RFRP-1 was purified from bovine hypothalamus.

First, 2.0 kg of frozen bovine hypothalamus was boiled in ultra-pure water (milli-Q water), to which acetic acid was added to give a concentration of 1M. Then, the hypothalamus was homogenized with a Polytron. After overnight stirring, supernatant was obtained by centrifugation. Trifluoroacetic acid (TFA) was added to the supernatant to give a concentration of 0.05%, and the supernatant was applied to a C18 column (Prep C18 125 Å; Waters). The peptide bound to the column was eluted in a step-wise manner with 0.05% TFA-containing 10%, 30% and 50% acetonitrile solution. 30% acetonitrile fraction was diluted with two volumes of 20 mM ammonium acetate (pH 4.7) and applied to an ion exchange column HiPrep CM-Sepharose FF (Pharmacia). The peptide bound to the ion exchange column was eluted in a step-wise manner with 0.1, 0.2, 0.5 and 1.0 M NaCl in 10% acetonitrile-containing 20 mM ammonium acetate (pH 4.7). Three volumes of cold acetone was added to 0.1 M NaCl fraction which contained the highest RFRP-1-like immune activity, followed by centrifugation to remove the precipitate. The resultant supernatant was concentrated in an evaporator. TFA was added to the concentrated supernatant to give a concentration of 0.1%, and then the supernatant was applied to a reversed-phase HPLC column RESOURCE RPC (Pharmacia) for further separation. Elution from the RESOURCE RPC column was performed with the density gradient of 10–30% acetonitrile. The major RFRP-1-like activity was eluted with approximately 22% acetonitile. This active fraction was separated in a cation exchange column TSK gel CM-SW (Tosoh) using the density gradient of 0.2–0.6 M NaCl in 10% acetonitrile-containing 20 mM ammonium acetate (pH 4.7). The major RFRP-1-like activity was eluted with approximately 0.3 M NaCl. TFA was added to the RFRP-1-like activity-containing CM-2SW column fraction to give a concentration of 0.1%. Then, this fraction was fractionated further in a reversed-phase column Diphenyl 219TP52 (Vydac). As a result of elution using the density gradient of 21–25% acetonitrile, RFRP-1-like immune activity was eluted with 23% acetonitrile. This RFRP-1-like immune activity-containing fraction was purified finally in a reversed-phase column µRPC C2C18 SC2.1/10 using the density gradient of 22–23% acetonitile to thereby obtain a single peak which is consistent with the RFRP-1-like immune activity (FIG. 12).

Example A3

Analysis of the N-Terminal Amino Acid Sequence of the Finally Purified Product and Determination of its Molecular Weight by Mass Spectrometry When N-terminal amino acids of the finally purified product obtained in Example A3 were analyzed with a protein sequencer (Model 491cLC; Applied Biosystems), an amino acid sequence S-L-T-F-E-E-V-K-D-X-A-P-K-I-K-M-N-K-P-V- (where X represents an unidentified amino acid residue) (SEQ ID NO: 73) was obtained.

When the molecular weight of the finally purified product was determined with ESI-MS (Mermoquest), a value 3997.0 was obtained.

From these results, it was found that the finally purified product from bovine hypothalamus is a peptide consisting of the 35 amino acids from position 58 (Ser) to position 92 (Phe) of the amino acid sequence represented by SEQ ID NO: 14.

Example A4

Preparation of a Structural Gene for a Peptide which has an Amino Acid Sequence which is from Position 56 (Ser) to Position 92 (Phe) of the Amino Acid Sequence Represented by SEQ ID NO: 1 and whose C-Terminal Carboxyl Group is Amidated (Hereinafter, Sometimes Referred to as "hRFRP-1(37)")

A structural gene for hRPRP-1(37) was prepared using the four DNA fragment shown in SEQ ID NOS: 59–62 (#1: SEQ ID NO: 15 and #4: SEQ ID NO: 18; Kiko-Tech) and (#2: SEQ ID NO: 16 and #3: SEQ ID NO: 17; Amersham Pharmacia Biotech).

a) Phosphorylation of DNA Oligomers

Two oligomers #1 and #4 which are to be the 5'-terminal regions were excluded from this treatment. One microgram each of the remaining two oligomers was reacted in 100 μl of phosphorylation reaction solution [50 mM Tris-HCl (pH 7.6), 10 mM MgCl$_2$, 1 mM spermidine, 10 mM dithiothreitol, 0.1 mg/ml bovine serum albumin, 1 mM ATP, 10 units of T4 polynucleotide kinase (Nippon Gene)] at 37° C. for 1 hr to phosphorylate the 5' end. After phenol treatment, the aqueous layer was recovered, and two volumes of ethanol was added thereto. The mixture was cooled to −70° C. and then centrifuged to precipitate DNA.

b) Ligation of DNA Fragments

The phosphorylated DNA fragments obtained in a) above and #1 and #4 (1 μg each) were added together to 10 mM Tris-HCl, 2 mM EDTA to make a 120 μl mixture. This mixture was retained at 80° C. for 10 min and then gradually cooled to room temperature for annealing. Ligation was performed with TaKaRa DNA Ligation Kit ver. 2 (Takara Shuzo). Briefly, 30 μl of liquid II contained in the kit was added to 30 μl of the above annealing mixture and mixed thoroughly. Then, 60 μl of liquid I contained in the kit was added thereto and reacted at 37° C. for 1 hr to perform ligation. After phenol treatment, the aqueous layer was recovered, and two volumes of ethanol was added thereto. The mixture was cooled to −70° C. and then centrifuged to precipitate DNA.

c) Phosphorylation of the 5' End

The precipitate was dissolved in 10 μl of TE buffer (10 mM Tris-HCl (pH 8.0), 1 mM EDTA) and reacted in 100 μl of phosphorylation reaction solution [50 mM Tris-HCl (pH 7.6), 10 mM MgCl$_2$, 1 mM spermidine, 10 mM dithiothreitol, 0.1 mg/ml bovine serum albumin, 1 mM ATP, 10 units of T4 polynucleotide kinase (Nippon Gene)] at 37° C. for 1 hr to phosphorylate the 5' end. After phenol treatment, the aqueous layer was recovered, and two volumes of ethanol was added thereto. The mixture was cooled to −70° C. and then centrifuged to precipitate DNA, which was dissolved in 20 μl of TE buffer.

Example A5

Preparation of hRFRP-1(37) Expression Plasmid

As an expression vector, pTFC (described in Japanese Unexamined Patent Publication No. 2000-270871) was digested with NdeI and AvaI (Takara Shuzo) at 37° C. for 4 hr. The digest was electrophoresed on 1% agarose gel, and a 4.4 kb DNA fragment was extracted with QIAquick Gel Extraction Kit (Qiagen) and dissolved in 25 μl of TE buffer. This NdeI-AvaI fragment from pTFC was ligated to the structural gene for hRFRP-1(37) prepared above using TaKaRa DNA Ligation Kit ver. 2 (Takara Shuzo). With 10 μl of the resultant ligation reaction solution, E. coli JM109 competent cells were transformed and plated on 10 μg/ml tetracycline-containing LB agar medium. After overnight culture at 37° C., tetracycline resistant colonies grown on the medium were selected. This transformant was cultured overnight in LB medium, followed by preparation of plasmid pTFCRFRP-1 using QIAprep8 Miniprep Kit (Qiagen). The nucleotide sequence of the structural gene moiety for hRFRP-1(37) in this plasmid was confirmed with Model 377 DNA Sequencer (Applied Biosystems). E. coli MM294 (DE3) was transformed with plasmid pTFCRFRP-1 to thereby obtain RFRp-1-CS23 fusion protein-expressing Escherichia coli MM294 (DE3)/pTFCRFRP-1 (FIG. 13).

Example A6

The transformant obtained in Example A5 was cultured under shading in 1 L of 5.0 mg/L tetracycline-containing LB medium (1% peptone, 0.5% yeast extract, 0.5% sodium chloride) in a 2 L-flask at 37° C. for 8 hr. The resultant culture broth was transferred into a 50 L-fermenter containing 19 L of primary fermentation medium (1.68% sodium monohydrogenphosphate, 0.3% potassium dihydrogenphosphate, 0.1% ammonium chloride, 0.05% sodium chloride, 0.05% magnesium sulfate, 0.02% defoaming agent, 0.00025% ferrous sulfate, 0.00025% thiamine hydrochloride, 1.5% glucose, 1.5% casamino acid) and cultured at 30° C. under aeration and agitation. When the turbidity of the culture broth reached about 500 Klett Units, isopropyl-β-D-thiogalactopyranoside was added to give a final concentration of 12 mg/L. Cells were cultured for another 4 hr. After completion of the cultivation, the culture broth was centrifuged to thereby obtain about 500 g of wet cells, which were frozen and stored at −80° C.

Example A7

Acquisition of hRFRP-1(37)

To the 500 g of the cells obtained in Example A6, 1000 ml of a solution containing 6 M guanidine hydrochloride and 0.2 M Tris-HCl (pH 8.0) was added and agitated for about 4 hr. The resultant mixture was centrifuged (10000 rpm, 60 min), and the supernatant was diluted with 29 L of a solution containing 1 mM dithiothreitol and 50 mM Tris-HCl (pH 8.0). The diluted solution was left stationary overnight at 10° C. Then, the pH of the solution was adjusted at 6.0 with concentrated HCl. The resultant solution was fed to an AF-Heparin Toyopearl 650M column (11.3 cm ID×13 cm L; Tosoh) pre-equilibrated with 50 mM phosphate buffer (pH 6.0). After adsorption and washing, the adsorbate was eluted with 50 mM phosphate buffer, 2M NaCl, pH 6.0. As a result, 1000 ml of hRFRP-1(37)-CS23 fusion protein (i.e. a fusion protein of the polypeptide of the invention and CS23) fraction was obtained.

This eluate was concentrated in Pellicon Minicassette (Millipore) while adding 0.1 M acetic acid. As a result, a solution of hRFRP-1(37)-CS23 fusion protein in 0.1 M acetic acid was obtained. Urea was added to this solution to give a final concentration of 6M, and then 445 mg of 1-cyano-4-dimethylamino pyridinium salt (DMAP-CN) was added thereto and reacted at room temperature for 15 min. After completion of the reaction, the reaction solution was fed to a Sephadex G-25 column (46 mm ID×600 mm L; Pharmacia) pre-equilibrated with 10% acetic acid. Then, 10% acetic acid was fed to the column at a flow rate of 6 ml/min to thereby obtain a fraction of S-cyanylated hRFRP-1(37)-CS23 fusion protein. This eluate was concentrated and de-salted in Pellicon Minicassette (Millipore) to thereby obtain a de-salted solution of hRFRP-1(37)-CS23 fusion protein. Urea was added to this de-salted solution to give a final concentration of 6 M. Further, 25% aqueous ammonia was added thereto to give a concentration of 3 M. Then, the resultant solution was reacted at 15° C. for 15 min. After completion of the reaction, the pH of the reaction solution was adjusted at 6.0 with acetic acid to thereby obtain hRFRP-1(37). The reaction solution was fed to a SP-5PW column (5.5 cm ID×30 cm L; Tosoh) pre-equilibrated with 50 mM MES buffer containing 3 M urea (pH 4.5). After adsorption and washing, elution was performed with stepwise gradient of 0–50% solution B (solution B=50 mM MES buffer+1 M NaCl+3 M urea) to thereby obtain hRFRP-1(37) (elution time: 60 min). This hRFRP-1(37) fraction was further fed to an ODS-120T column (21.5 mm ID×300 mm L; Tosoh) pre-equilibrated with 0.1% trifluoroacetic acid (TFA). After adsorption and washing, elution was performed with stepwise gradient of 3060% solution B (solution B=80% acetonitrile/0.1% TFA) to thereby pool hRFRP-1 (37) fractions (elution time: 45 min). Then, these fractions were lyophilized to obtain lyophilized powder of hRFRP-1 (37).

Example A8

Comparison of the Agonist Activities of Various RF Amide Peptides upon Human OT7T022 Receptor-Expressing CHO Cells Human OT7T022 receptor-expressing CHO cells prepared based on the procedures described in WO 00/29441 were plated in 24-well plates at 3×10$^5$ cells/well and cultured overnight. The cells were washed with Hanks' buffer (HBSS) supplemented with 0.05% BSA and 0.2 mM IBMX and then preincubated in the same buffer at 37° for 30 min. Then, the buffer was exchanged for HBSS supplemented with 0.05% BSA and 0.2 mM IBMX, this buffer supplemented with 1 µM forskolin alone, or this buffer supplemented with 1 µM forskolin and a peptide at a varied concentration, and the cells were incubated at 37° for 30 min. After the incubation, intracellular cAMP was extracted and determined for each well according to the protocol attached to the cAMP EIA Kit (Amersham). For each concentration of the peptides used, the ratio of inhibition of intracellular cAMP increase by forskolin treatment was calculated to thereby obtain the dose-reaction curves as shown in FIG. 14. The ED$_{50}$ values of the peptides tested were as follows: hRFRP-1–12 (peptide having the amino acid sequence which is from position 81 (Met) to position 92 (Phe) of SEQ ID NO: 1, (○))(4.5 nM); hRFRP-1–37 (peptide having the amino acid sequence which is from position 56 (Ser) to position 92 (Phe) of SEQ ID NO: 1, (■)(21 nM); rRFRP-1–37 (peptide having the amino acid sequence which is from position 58 (Ser) to position 94 (Phe) of SEQ ID NO: 50, (□))(30 nM); hRFRP-2–12 (peptide having the amino acid sequence which is from position 101 (Phe) to position 112 (Ser) of SEQ ID NO: 1, (▲)); hRFRP-3–8 (peptide having the amino acid sequence which is from position 124 (Val) to position 131 (Phe) of SEQ ID NO: 1, (□))(9.9 nM); PQRF amide (peptide represented by Pro-Gln-Arg-Phe-NH$_2$ (□) (SEQ ID NO: 74)) (1000 nM or more); LPLRF amide (peptide represented by Leu-Pro-Leu-Arg-Phe-NH$_2$ (●) (SEQ ID NO: 75))(36 nM); and NPFF (peptide represented by Asn-Pro-Phe-Phe (□)(SEQ ID NO: 76))(140 nM).

Example A9

Examination of the Effect of Pertussis Toxin upon the Activation of Human OT7T022 Receptor by an RFRP Peptide The human OT7T022 receptor-expressing CHO cells obtained in Example A8 were plated in 24-well plates at 1×10$^5$ cells/well and cultured overnight. Then, the medium was changed for 100 ng/nm pertussis toxin (Sigma)-containing medium or a control medium, and the cells were cultured overnight. The cells were washed with Hanks' buffer (HBSS) supplemented with 0.05% BSA and 0.2 mM IBMX and then pre-incubated in the same buffer at 37° C. for 30 min. Subsequently, the buffer was exchanged for HBSS supplemented with 0.05% BSA and 0.2 mM IBMX, HBSS supplemented with 1 µM forskolin alone, or HBSS supplemented with 1 µM forskolin and a peptide at various concentrations, and the cells were incubated at 37° C. for 30 min. After the incubation, the buffer was exchanged for HBSS supplemented with 0.05% BSA and 0.2 mM IBMX (black column), this buffer supplemented with 1 µM forskolin alone (white column), or this buffer supplemented with 1 µM forskolin and 0.1 µM RFRP-1–12 (peptide having the amino acid sequence which is from position 81 (Met) to position 92 (Phe) of SEQ ID NO: 1) (column with slant lines), and the cells were incubated at 37° C. for 30 min. After the incubation, intracellular cAMP was extracted and determined for each well according to the protocol attached to the cAMP EIA Kit (Amersham). As a result, as shown in FIG. 15, cAMP production inhibitory activity disappeared in those cells treated with pertussis toxin. Thus, it was shown that the cAMP production inhibitory reaction mediated by OT7T022 receptor is co-operating with pertussis toxin sensitive G protein α subunit Gi (inhibitory) or Go.

Example B1

Preparation of Anti-Rat RFRP-3 Monoclonal Antibody

A monoclonal antibody was prepared against a peptide C-FPSLPQRF-NH$_2$ (SEQ ID NO: 77) as an antigen; this peptide represents the C-terminal 8 amino acids of rat-type RFRP-3 (the C-terminus is amidated) to which one Cys residue is added at the N-terminus. The antigen peptide (0.6 mg) was conjugated with bovine serum albumin (BSA) using maleimide. The resultant conjugate (100 µg) was subcutaneously injected into mice three times to immunize them. Then, 50 µg of the conjugate was injected into the tail vein as final immunization. Four days after the final immunization, splenocytes were recovered from each mouse and fused to mouse myeloma cells (P3-X63Ag8-U1) using polyethylene glycol. After this cell fusion, a hybridoma cell 7F6 was selected and cultured in a large quantity using INTRE-GRA CL-1000 to thereby obtain a culture supernatant of 7F6. From this culture supernatant, anti-rat RFRP-3 monoclonal antibody was obtained using HiTrap rProtein A column (Pharmacia). Isotyping of this monoclonal antibody with Mouse mAb Isotyping Kit (Amersham) revealed that the subtype of this monoclonal antibody was IgG2b κ chain.

Example B2

Construction of Competitive EIA

First, the peptide used as the antigen was conjugated with horse radish peroxidase (HRP) using maleimide to thereby prepare a conjugate HRP-rat RFRP-3. Then, using this conjugate HRP-rat RFRP-3 and the anti-rat RFRP-3 monoclonal antibody obtained in Example B1, a competitive EIA was constructed.

Briefly, 50 µl of the anti-rat RFRP-3 monoclonal antibody diluted with a buffer (phosphate buffered saline (PBS) containing 2 mM EDTA, 0.4% BSA, 0.1 M NaCl and 0.1% micro-O-protect) was added to each well of 96-well plates coated with anti-mouse IgGAM (Cappel) at 1.5 µg/well and blocked with Block ACE (Dainippon Pharmaceutical). A 50 µl sample dissolved in the same buffer was also added to each well. After a 16-hr incubation at 4° C., 50 µl of HRP-rat RFRP-3 diluted with the buffer was added to each well.

After 2-hr incubation at room temperature, the plates were washed with 0.1% Tween 20 (Sigma)-containing PBS. Then, the activity of HRP bound to each well was detected by a color reaction using TMB microwell peroxidase system, followed by measurement of the absorbance at 450 nm. Changes in absorbance when RFRP-3-related peptides were added are shown in FIG. 16.

Example B3

Purification of Endogenous RFRP-3 from Bovine Hypothalamus

RFRP-3-like immune activity was found in a crude peptide fraction from bovine hypothalamus in the competitive EIA constructed in Example B2. Using this RFRP-3-like immune activity as an indicator, an endogenous RFRP-3 was purified from bovine hypothalamus.

First, 2.0 kg of frozen bovine hypothalamus was boiled in ultra-pure water (milli-water), to which acetic acid was added to give a concentration of 1M. Then, the hypothalamus was homogenized with a Polytron. After overnight stirring, supernatant was obtained by centrifugation. Trifluoroacetic acid (TFA) was added to the supernatant to give a concentration of 0.05%, and the supernatant was applied to a C18 column (Prep C18 125 Å; Waters). The peptide bound to the column was eluted in a step-wise manner with 0.05% TFA-containing 10%, 30% and 50% acetonitrile solution. 30% acetonitrile fraction was diluted with two volumes of 20 mM ammonium acetate (pH 4.7) and applied to an ion exchange column HiPrep C4-Sepharose FF (Pharmacia). The peptide bound to the ion exchange column was eluted in a stepwise manner with 0.1, 0.2, 0.5 and 1.0 M NaCl in 10% acetonitrile-containing 20 mM ammonium acetate (pH 4.7). Three volumes of cold acetone was added to 0.2 M NaCl fraction which contained the highest RFRP-3-like immune activity, followed by centrifugation to remove the precipitate. The resultant supernatant was concentrated in an evaporator. TFA was added to the concentrated supernatant to give a concentration of 0.1%, and then the supernatant was applied to a reversed-phase HPLC column RESOURCE RPC (Pharmacia) for further separation. Elution from the RESOURCE RPC column was performed with the density gradient of 10–30% acetonitrile. The major RFRP-3-like activity was eluted with approximately 23% acetonitrile. This active fraction was separated in a cation exchange column TSK gel CM-SW (Tosoh) using the density gradient of 0.2–0.6 M NaCl in 10% acetonitrile-containing 20 mM ammonium acetate (pH 4.7). The major RFRP-3-like activity was eluted with approximately 0.36 M NaCl. TFA was added to the RFRP-3-like activity-containing CM-2SW column fraction to give a concentration of 0.1%. Then, this fraction was purified finally in a reversed-phase column μRPC C2/C18 SC2.1/10 using the density gradient of 18–23% acetonitrile to thereby obtain a single peak which is consistent with the RFRP-3-like immune activity (FIG. 17).

Example B4

Analysis of the N-Terminal Amino Acid Sequence of the Finally Purified Product and Determination of its Molecular Weight by Mass Spectrometry When N-terminal amino acids of the finally purified product obtained in Example B3 were analyzed with a protein sequencer (Model 491cLC; Applied Biosystems), the amino acid sequence shown in FIG. 18 was obtained.

When the molecular weight of the finally purified product was determined with ESI-MS (LCQ; Thermoquest), a value 3302 was obtained (FIG. 19). The MS/MS spectrum measured with a pentavalent molecule-related ion (m/z 661) as a precursor ion was assigned to the structure of a peptide consisting of the 28 residues starting from Ala 104 of RFRP precursor (FIG. 20). From these results, it was found that the finally purified product from bovine hypothalamus is a peptide consisting of the 28 amino acids from Ala 104 to Phe 131 of bovine RFRP precursor.

Example B5

Preparation of Anti-Rat RFRP-3 Polyclonal Antibody

A polyclonal antibody was prepared against a peptide NMEAGTMSGFPSLPQRF-Cys (SEQ ID NO: 78) as an antigen; this peptide is rat-type RFRP-3 consisting of 17 amino acids to which one Cys residue is added at the C-terminus. The antigen peptide (0.6 mg) was conjugated with bovine serum albumin (BSA) using maleimide. The resultant conjugate (500 μg) was subcutaneously injected into rabbits four times. Then, blood was taken from them to obtain antisera. Two volumes of 3 M ammonium sulfate was added to 10 ml of each anti-serum, followed by preparation of IgG fraction. This fraction was fed to an antigen column (Sulfo-link column (Pierce) to which the antigen is bound) for affinity purification. The bound fraction was obtained as anti-rat RFRP-3 polyclonal antibody.

Example B6

Construction of Competitive EIA

First, the peptide used as the antigen was conjugated with horse radish peroxidase (HRP) using maleimide to thereby prepare a conjugate HRP-rat RFRP-3 (N). Then, using this conjugate HRP-rat RFRP-3 (N) and the anti-rat RFRP-3 polyclonal antibody obtained in Example B5, a competitive EIA was constructed.

Briefly, 50 μl of the anti-rat RFRP-3 polyclonal antibody diluted with a buffer (phosphate buffered saline (PBS) containing 2 mM EDTA, 0.4% BSA, 0.1 M NaCl and 0.1% micro-O-protect) was added to each well of 96-well plates coated with anti-rabbit IgG (Cappel) at 1.5 μg/well and blocked with Block ACE (Dainippon Pharmaceutical). A 50 μl sample dissolved in the same buffer was also added to each well. After a 16-hr incubation at 4° C., 50 μl of HRP-rat RFRP-3 (N) diluted with the buffer was added to each well. After 2-hr incubation at room temperature, the plates were washed with 0.1% Tween 20 (Sigma)-containing PBS. Then, the activity of HRP bound to each well was detected by a color reaction using TMB microwell peroxidase system, followed by measurement of the absorbance at 450 nm. Changes in absorbance when RFRP-3-related peptides were added are shown in FIG. 21.

Example B7

Preparation of Human-Type RFRP-3(28)

Ala-Thr-Ala-Asn-Leu-Pro-Leu-Arg-Ser-Gly-Arg-Asn-

Met-Glu-Val-Ser-Leu-Val-Arg-Arg-Val-Pro-Asn-Leu-

Pro-Gln-Arg-Phe-NH$_2$ (SEQ ID NO: 63)

Commercial p-methyl BHA resin (Applied Biosystems) (0.5 mmole) was placed in a reactor in a peptide synthesizer (Applied Biosystems Model 430A), and swollen with DCM. Then, the first amino acid Boc-Phe was activated by the HOBt/DCC method and introduced into the p-methyl BHA resin. Subsequently, the resin was treated with 50% TFA/DCM to remove the Boc group to thereby liberate the amino group, and then neutralized with DIEA. The subsequent amino acid Boc-Arg(Tos) was condensed with this amino group by the HOBt/DCC method. The presence or absence of unreacted amino groups was examined by a ninhydrin test. If unreacted amino groups remained, the condensation was repeated. When the completion of the reaction was confirmed, Boc-Gln, Boc-Pro, Boc-Leu, Boc-Asn, Boc-Val, Boc-Arg(Tos), Boc-Ser(Bzl), Boc-Glu(OcHex), Boc-Met, Boc-Asn, Boc-Gly and Boc-Thr(Bzl) were condensed in the same manner according to the order of the sequence of human-type RFRP-3(28) to thereby obtain Boc-Ala-Thr(Bzl)-Ala-Asn-Leu-Pro-Leu-Arg(Tos)-Ser(Bzl)-Gly-Arg(Tos)-Asn-Met-Glu(OcHex)-Val-Ser(Bzl)-Leu-Val-Arg(Tos)-Arg(Tos)-Val-Pro-Asn-Leu-Pro-Gln-Arg(Tos)-Phe-pMBHA (SEQ ID NO: 63) resin.

In a hydrogen fluoride reactor made of Teflon, 0.3 g of this resin was reacted with 3.1 g of p-cresol and 15 ml of hydrogen fluoride at 0° C. for 60 min. The hydrogen was distilled off under reduced pressure. The residue was diluted with 100 ml of diethyl ether, stirred, filtered through a glass filter, and the fraction on the filter was dried. This fraction was suspended in 50 ml of 50% aqueous solution of acetic acid and stirred to extract the peptide. After the extraction, the resin was separated and the peptide was concentrated under reduced pressure to about 5 ml. This peptide was applied to a Sephadex G-25 column (2×90 cm). Development was carried out with 50% aqueous acetic acid solution, and major fractions were collected and lyophilized. Subsequently, this crude peptide was dissolved in 1.5 ml of 5% thioglycollic acid/50% acetic acid and retained at 50° C. for 12 hr to reduce the Met-oxidant peptide. Then, the peptide was applied to a reversed phase column packed with LiChroprep RP-18 (Merck) and repeatedly purified by gradient elution using 0.1% TFA/H$_2$O and 0.1% TFA-containing 33% acetonitrile/H$_2$O. Major fractions were pooled and lyophilized to obtain 30 mg of white powder.

(M+H)$^+$ value by mass spectrometry: 3190.9
HPLC elution time: 15.5 min
Column conditions:
  Column: Wakosil II5C18HG (4.6×100 mm)
  Eluent: A (0.1% TFA-containing 5% acetonitrile/H$_2$O)
    B (0.1% TFA-containing 55% acetonitrile/H$_2$O)
    Linear gradient elution from A to B (25 min.)
  Flow rate: 1.0 ml/min Example B8

Preparation of Human-Type RFRP-3(31)

Ser-Ala-Gly-Ala-Thr-Ala-Asn-Leu-Pro-Leu-Arg-Ser-Gly-Arg-Asn-Met-Glu-Val-Ser-Leu-Val-Arg-Arg-Val-Pro-Asn-Leu-Pro-Gln-Arg-Phe-NH$_2$ (SEQ ID NO: 65)

Boc-Gly, Boc-Ala and Boc-Ser(Bzl) were further condensed in succession in the same manner with the Boc-Ala-Thr(Bzl)-Ala-Asn-Leu-Pro-Leu-Arg(Tos)-Ser(Bzl)-Gly-Arg(Tos)-Asn-Met-Glu(OcHex)-Val-Ser(Bzl)-Leu-Val-Arg(Tos)-Arg(Tos)-Val-Pro-Asn-Leu-Pro-Gln-Arg(Tos)-Phe-pMBHA resin prepared in Example B7 to thereby obtain Boc-Ser(Bzl)-Ala-Gly-Ala-Thr(Bzl)-Ala-Asn-Leu-Pro-Leu-Arg(Tos)-Ser(Bzl)-Gly-Arg(Tos)-Asn-Met-Glu(OcHex)-Val-Ser(Bzl)-Leu-Val-Arg(Tos)-Arg(Tos)-Val-Pro-Asn-Leu-Pro-Gln-Arg(Tos)-Phe-pMBHA (SEQ ID NO: 65) resin.

This resin was treated with hydrogen fluoride in the same manner as in Example B7. The resultant crude peptide was purified in the same manner to thereby obtain 25 mg of white powder.

(M+H)$^+$ value by mass spectrometry: 3405.9
HPLC elution time: 15.7 min
Column conditions:
  Column: Wakosil II5C18HG (4.6×100 mm)
  Eluent: A (0.1% TFA-containing 5% acetonitrile/H$_2$O)
    B (0.1% TFA-containing 55% acetonitrile/H$_2$O)
    Linear gradient elution from A to B (25 min.)
  Flow rate: 1.0 ml/min Example B9

Preparation of Leu-Pro-Gln-Arg-Phe-NH$_2$ (SEQ ID NO: 69): hRFRP-3(5)

In the course of preparation of the resin of Example B7, a part of Boc-Leu-Pro-Gln-Arg(Tos)-Phe-pMBHA resin (SEQ ID NO: 69) was taken out, treated with hydrogen fluoride, purified in a Sephadex G-25 column (2×90 cm) and further purified in a reversed-phase column packed with LICHROPREP™ RP-18 (Merck) in the same manner as in Examples B7 and B8, to thereby obtain Leu-Pro-Gln-Arg-Phe-NH$_2$ (SEQ ID NO: 69).

Example B10

Preparation of Asn-Leu-Pro-Gln-Arg-Phe-NH$_2$ (SEQ ID NO: 70): hRFRP-3(6)

In the course of preparation of the resin of Example B7, a part of Boc-Asn-Leu-Pro-Gln-Arg(Tos)-Phe-pMBHA (SEQ ID NO: 70) resin was taken out, treated with hydrogen fluoride, purified in a Sephadex G-25 column (2×90 cm) and further purified in a reversed-phase column packed with LICHROPREP™ RP-18 (Merck) in the same manner as in Examples B7 and B8, to thereby obtain Asn-Leu-Pro-Gln-Arg-Phe-NH$_2$ (SEQ ID NO: 70).

Example B11

Preparation of Pro-Asn-Leu-Pro-Gln-Arg-Phe-NH$_2$ (SEQ ID NO: 71): hRFRP-3(7)

In the course of preparation of the resin of Example B7, a part of Boc-Pro-Asn-Leu-Pro-Gln-Arg(Tos)-Phe-pMBHA (SEQ ID NO: 71) resin was taken out, treated with hydrogen fluoride, purified in a Sephadex G-25 column (2×90 cm) and further purified in a reversed-phase column packed with LICHROPREP™ RP-18 (Merck) in the same manner as in Examples B7 and B8, to thereby obtain Pro-Asn-Leu-Pro-Gln-Arg-Phe-NH$_2$ (SEQ ID NO: 71).

Example B12

Preparation of $^{125}$I-Labeled hRFRP-3(8)

Twenty microliters of Tyr-hRFRP-3(8) (0.1 M), 10 μl of distilled water, 20 μl of lactoperoxidase (Sigma; diluted to 10 μg/ml with 0.1 M HEPES-NaOH pH 7.0), 10 μl of Iodine-125 (Amersham; IMS-30, 74 MBq) and 20 µl of 0.005% hydrogen peroxide (Wako Purechemical Industries) were mixed and left stationary at room temperature for 10 min. Then, 600 µl of 0.1% TFA was added thereto. The resultant mixture was separated by reversed-phase HPLC and the peak of the labeled peptide was recovered. This fraction was immediately stored on ice, and an equal volume of assay buffer [50 mM Tris-HCl, pH 7.5, 5 mM EDTA, 0.1% bovine serum albumin (Sigma), 0.5 mM PMSF (Wako Purechemical Industries), 20 µg/ml leupeptin (Peptide Institute, Inc.), 0.1 µg/ml pepstatin A (Peptide Institute, Inc.), 4 µg/ml E64 (Peptide Institute, Inc.) and 10 mM $MgCl_2$] was added thereto. An aliquot of this mixture was taken and subjected to measurement of radioactivity with a γ counter. The remaining sample was divided into 100 µl aliquots and stored frozen.

Example B13

Preparation of the Membrane Fraction from Human-Type OT7T022-Expressing CHO Cells A flask used for culturing human-type OT7T022-expressing CHO cells was washed with 5 mM EDTA/PBS. The cells were peeled off using 5 mM EDTA/PBS, centrifuged, and recovered. Then, the cells were suspended in 25 ml of membrane fraction preparation buffer [50 mM Tris-HCl, pH 7.5, 5 mM EDTA, 0.1% bovine serum albumin (Sigma), 0.5 mM PMSF (Wako Purechemical Industries), 20 µl g/ml leupeptin (Peptide Institute, Inc.), 0.1 µg/ml pepstatin A (Peptide Institute, Inc.) and 4 µg/ml E-64 (Peptide Institute, Inc.)] and homogenized on ice using a Polytron (12,000 rpm; 15 sec×3 times). The homogenized cells were centrifuged in a high-speed refrigerated microcentrifuge at 4° C., at 1,000 g for 10 min to recover the supernatant. To the precipitate, 25 ml of the membrane fraction preparation buffer was added and centrifuged in the same manner to recover the supernatant. These supernatants were collected together, passed through a cell strainer and dispensed into centrifugal tubes, followed by centrifugation at 4° C. at 100,000 g for 1 hr. The resultant pellet was recovered, suspended in a small amount of the membrane fraction preparation buffer and suspended with a Teflon homogenizer. Subsequently, an aliquot of this sample was used for measuring the amount of protein, and the remaining sample was dispensed into small aliquots and stored at −80° C.

Example B14

Binding Inhibition Experiment

An assay buffer [50 mM Tris-HCl, pH 7.5, 5 mM EDTA, 0.1% bovine serum albumin (Sigma), 0.5 mM PMSF (Wako Purechemical Industries), 20 µg/ml leupeptin (Peptide Institute, Inc.), 0.1 µg/ml pepstatin A (Peptide Institute, Inc.), 4 µg/ml E64 (Peptide Institute, Inc.) and 10 mM $MgCl_2$] was prepared. With this buffer, the membrane fraction from human-type OT7T022-expressing CHO cells was diluted to give a concentration of 1 µg/25 µl. With respect to the peptides shown in Table 1, $10^{-2}$ M or $10^{-3}$M stock solution was diluted with the assay buffer to give 2-fold concentrations of the assay concentrations ($10^{-5}$M, $10^{-6}$M, $10^{-7}$M, $10^{-8}$M, $10^{-9}$M, $10^{-10}$M, $10^{-11}$M). In order to measure non-specific binding, 20 µM Tyr-hRFRP-3(8) was prepared. Sample solutions prepared, NSB and the assay buffer were dispensed into polypropylene 96-well plates in quadruplicate as total 50 µl/well. With respect to the labeled peptide, the $^{125}$I-Tyr-hRFRP-3(8) prepared was diluted to 400 pM with measuring buffer, and 25 µl of this dilution was added to each well and agitated with a plate mixer. Twenty-five microliter of the membrane fraction solution from human-type OT7T022-expressing CHO cells was added thereto, agitated with a plate mixer and incubated at room temperature for 1.5 hr. Using a cell harvester for 96-well plates, the contents of each well were adsorbed onto a filter unit (GF/C, treated with polyethylene imine) pre-moisturized with washing buffer (50 mM Tris-HCl, pH 7.5). After washing 5 times with the washing buffer, the adsorbate was dried thoroughly. The lower part of the filter unit was sealed. Then, 50 µl of liquid scintillator was added to each well and the upper part of the filter unit was sealed. Radioactivity was measured with a Top Count (Packard), and data were analyzed in triplicate. $IC_{50}$ values are shown in Table 1.

Example B15 cAMP Production Inhibition Experiment

Human-type OT7T022-expressing CHO cells were subcultured to 24-well plates at $3 \times 10^5$ cells/well and cultured for one day at 37° C. under 5% $CO_2$ 95% air. An assay buffer was prepared by adding to Hanks' Balanced Salt Solution (Gibco) 0.05% bovine serum albumin and 200 µM 3-isobutyl-1-methylxanthine (Sigma). The plates cultured overnight were washed twice with 400 µl of the assay buffer. Then, the medium was exchanged for 400 µl of the assay buffer, and the cells were cultured at 37° C., for 30 min under 100% air. A sample dilution buffer was prepared by adding 1 µM forskolin to the assay buffer. Using this sample dilution buffer, stock solutions ($10^{-2}$ M or $10^{-3}$ M) of the peptides shown in Table 1 were diluted to prepare $10^{-6}$M, $10^{-7}$M, $10^{-8}$M, $10^{-9}$M and $10^{-10}$M sample solutions. The plates cultured for 30 min with the assay buffer were taken out, washed with the assay buffer once, and 500 µl of a sample solution was added thereto. For each sample, measurement was performed in triplicate. Further, the equal volume of the assay buffer was added for measuring the basal level; and the equal volume of the sample dilution buffer was added for measuring the maximum level. Plates were cultured at 37° C. for 30 min under 100% air. Then, the amount of intracellular cAMP was determined with Biotrak™ cAMP enzyme immunoassay (EIA) system (Amersham Pharmacia Biotech) according to the protocol attached to this system. The difference between the maximum cAMP level and cAMP level when each sample was added was calculated, and then percentage against the amount of cAMP production promoted by forskolin was calculated. This percentage was taken as inhibition ratio against cAMP production. $EC_{50}$ values of individual samples are shown in Table 1.

TABLE 1

|  | Binding inhibition $IC_{50}$ (nM) | cAMP production inhibition $EC_{50}$ (nM) |
| --- | --- | --- |
| hRFRP-3 (31) | 1.3 | 4.8 |
| hRFRP-3 (28) | 1.1 | 5.1 |
| hRFRP-3 (8) | 1.2 | 4.1 |
| hRFRP-3 (7) | 0.62 | 3.2 |
| hRFRP-3 (6) | 2.6 | 37 |
| hRFRP-3 (5) | 2.1 | 38 |
| hRFRP-3 (28) | 1.6 | 4.1 |

INDUSTRIAL APPLICABILITY

The RFRP-3 of the invention has both promoting and inhibiting effects upon prolactin secretion. This means that the RFRP-3 of the invention may be used as prophylactic and therapeutic agents for various diseases associated with prolactin secretion insufficiency based on its prolactin secretion-promoting effect. On the other hand, since the RFRP-3 of the invention has strong affinity with its receptor protein, when administered at a high dose the RFRP-3 of the invention causes desensitization against prolactin secretion and, as a result, has an effect in inhibiting prolactin secretion. In such cases, the RFRP-3 of the invention may be used as prophylactic and therapeutic agents for various diseases associated with excessive prolactin secretion.

What is claimed is:

1. An isolated RFamide-Related Peptide-3 (RFRP-3) peptide consisting of an amino acid sequence selected from the group consisting of:
  (1) an amino acid sequence which is from position 104 (Ala) to position 131 (Phe) of SEQ ID NO: 1;
  (2) an amino acid sequence which is from position 101 (Ser) to position 131 (Phe) of SEQ ID NO: 1;
  (4) an amino acid sequence which is from position 125 (Pro) to position 131 (Phe) of SEQ ID NO: 1;
  (5) an amino acid sequence which is from position 126 (Asn) to position 131 (Phe) of SEQ ID NO: 1; or
  (6) an amino acid sequence which is from position 127 (Leu) to position 131 (Phe) of SEQ ID NO: 1,
or an amide or ester thereof, or a salt thereof.

2. The peptide according to claim 1 wherein the C-terminal carboxyl group is amidated, or a salt thereof.

3. A pharmaceutical composition for regulating, promoting or inhibiting prolactin secretion comprising an effective amount of the peptide according to claim 1 or an amide or ester thereof, or a salt thereof and a pharmaceutically acceptable carrier excipient or diluent.

* * * * *

SEQUENCE LISTING

<160> NUMBER OF SEQ ID NOS: 72

<210> SEQ ID NO 1
<211> LENGTH: 180
<212> TYPE: PRT
<213> ORGANISM: Human

<400> SEQUENCE: 1

```
Met Glu Ile Ile Ser Ser Lys Leu Phe Ile Leu Leu Thr Leu Ala Thr
 1               5                   10                  15
Ser Ser Leu Leu Thr Ser Asn Ile Phe Cys Ala Asp Glu Leu Val Met
                20                  25                  30
Ser Asn Leu His Ser Lys Glu Asn Tyr Asp Lys Tyr Ser Glu Pro Arg
            35                  40                  45
Gly Tyr Pro Lys Gly Glu Arg Ser Leu Asn Phe Glu Glu Leu Lys Asp
        50                  55                  60
Trp Gly Pro Lys Asn Val Ile Lys Met Ser Thr Pro Ala Val Asn Lys
65                  70                  75                  80
Met Pro His Ser Phe Ala Asn Leu Pro Leu Arg Phe Gly Arg Asn Val
                85                  90                  95
Gln Glu Glu Arg Ser Ala Gly Ala Thr Ala Asn Leu Pro Leu Arg Ser
               100                 105                 110
Gly Arg Asn Met Glu Val Ser Leu Val Arg Arg Val Pro Asn Leu Pro
            115                 120                 125
Gln Arg Phe Gly Arg Thr Thr Thr Ala Lys Ser Val Cys Arg Met Leu
        130                 135                 140
Ser Asp Leu Cys Gln Gly Ser Met His Ser Pro Cys Ala Asn Asp Leu
145                 150                 155                 160
Phe Tyr Ser Met Thr Cys Gln His Gln Glu Ile Gln Asn Pro Asp Gln
                165                 170                 175
Lys Gln Ser Arg
            180
```

<210> SEQ ID NO 2
<211> LENGTH: 540
<212> TYPE: DNA
<213> ORGANISM: Human

<400> SEQUENCE: 2

```
atggaaatta tttcatcaaa actattcatt ttattgactt tagccacttc aagcttgtta    60
acatcaaaca tttttttgtgc agatgaatta gtgatgtcca atcttcacag caaagaaaat   120
tatgacaaat attctgagcc tagaggatac ccaaaagggg aaagaagcct caattttgag   180
gaattaaaag attggggacc aaaaaatgtt attaagatga gtacacctgc agtcaataaa   240
atgccacact ccttcgccaa cttgccattg agatttggga ggaacgttca agaagaaaga   300
agtgctggag caacagccaa cctgcctctg agatctgga agaaatatgga ggtgagcctc    360
```

```
gtgagacgtg ttcctaacct gccccaaagg tttgggagaa caacaacagc caaaagtgtc    420
tgcaggatgc tgagtgattt gtgtcaagga tccatgcatt caccatgtgc caatgactta    480
ttttactcca tgacctgcca gcaccaagaa atccagaatc ccgatcaaaa acagtcaagg    540
```

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3

```
gggctgcaca tagagactta attttag                                         27
```

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4

```
ctagaccacc tctatataac tgcccat                                         27
```

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5

```
gcacatagag acttaatttt agatttagac                                      30
```

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6

```
catgcacttt gactggtttc caggtat                                         27
```

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7

```
cagctttagg gacaggctcc aggtttc                                         27
```

<210> SEQ ID NO 8
<211> LENGTH: 196
<212> TYPE: PRT
<213> ORGANISM: Human

<400> SEQUENCE: 8

```
Met Glu Ile Ile Ser Ser Lys Leu Phe Ile Leu Leu Thr Leu Ala Thr
 1               5                  10                  15

Ser Ser Leu Leu Thr Ser Asn Ile Phe Cys Ala Asp Glu Leu Val Met
                20                  25                  30
```

Ser Asn Leu His Ser Lys Glu Asn Tyr Asp Lys Tyr Ser Glu Pro Arg
    35                  40                  45

Gly Tyr Pro Lys Gly Glu Arg Ser Leu Asn Phe Glu Glu Leu Lys Asp
    50                  55                  60

Trp Gly Pro Lys Asn Val Ile Lys Met Ser Thr Pro Ala Val Asn Lys
65                  70                  75                  80

Met Pro His Ser Phe Ala Asn Leu Pro Leu Arg Phe Gly Arg Asn Val
                85                  90                  95

Gln Glu Glu Arg Ser Ala Gly Ala Thr Ala Asn Leu Pro Leu Arg Ser
            100                 105                 110

Gly Arg Asn Met Glu Val Ser Leu Val Arg Arg Val Pro Asn Leu Pro
            115                 120                 125

Gln Arg Phe Gly Arg Thr Thr Thr Ala Lys Ser Val Cys Arg Met Leu
        130                 135                 140

Ser Asp Leu Cys Gln Gly Ser Met His Ser Pro Cys Ala Asn Asp Leu
145                 150                 155                 160

Phe Tyr Ser Met Thr Cys Gln His Gln Glu Ile Gln Asn Pro Asp Gln
                165                 170                 175

Lys Gln Ser Arg Arg Leu Leu Phe Lys Lys Ile Asp Asp Ala Glu Leu
            180                 185                 190

Lys Gln Glu Lys
        195

<210> SEQ ID NO 9
<211> LENGTH: 588
<212> TYPE: DNA
<213> ORGANISM: Human

<400> SEQUENCE: 9
atggaaatta tttcatcaaa actattcatt ttattgactt tagccacttc aagcttgtta      60
acatcaaaca ttttttgtgc agatgaatta gtgatgtcca atcttcacag caaagaaaat     120
tatgacaaat attctgagcc tagaggatac ccaaaagggg aaagaagcct caattttgag     180
gaattaaaag attggggacc aaaaaatgtt attaagatga gtacacctgc agtcaataaa     240
atgccacact ccttcgccaa cttgccattg agatttggga ggaacgttca agaagaaaga     300
agtgctggag caacagccaa cctgcctctg agatctggaa gaaatatgga ggtgagcctc     360
gtgagacgtg ttcctaacct gccccaaagg tttgggagaa caacaacagc caaaagtgtc     420
tgcaggatgc tgagtgattt gtgtcaagga tccatgcatt caccatgtgc caatgactta     480
ttttactcca tgacctgcca gcaccaagaa atccagaatc ccgatcaaaa acagtcaagg     540
agactgctat tcaagaaaat agatgatgca gaattgaaac aagaaaaa                  588

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
gcctagagga gatctaggct gggagga                                          27

<210> SEQ ID NO 11
<211> LENGTH: 27
<212> TYPE: DNA
<213> ORGANISM: Artificial Sequence

```
<220> FEATURE:
<223> OTHER INFORMATION: primer

<400> SEQUENCE: 11
gggaggaaca tggaagaaga aaggagc                                              27

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
gatggtgaat gcatggactg ctggagc                                              27

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
ttcctcccaa atctcagtgg caggttg                                              27

<210> SEQ ID NO 14
<211> LENGTH: 196
<212> TYPE: PRT
<213> ORGANISM: Bovine

<400> SEQUENCE: 14
```

Met Glu Ile Ile Ser Leu Lys Arg Phe Ile Leu Leu Met Leu Ala Thr
 1               5                  10                  15

Ser Ser Leu Leu Thr Ser Asn Ile Phe Cys Thr Asp Glu Ser Arg Met
            20                  25                  30

Pro Asn Leu Tyr Ser Lys Lys Asn Tyr Asp Lys Tyr Ser Glu Pro Arg
        35                  40                  45

Gly Asp Leu Gly Trp Glu Lys Glu Arg Ser Leu Thr Phe Glu Glu Val
    50                  55                  60

Lys Asp Trp Ala Pro Lys Ile Lys Met Asn Lys Pro Val Val Asn Lys
65                  70                  75                  80

Met Pro Pro Ser Ala Ala Asn Leu Pro Leu Arg Phe Gly Arg Asn Met
                85                  90                  95

Glu Glu Glu Arg Ser Thr Arg Ala Met Ala His Leu Pro Leu Arg Leu
            100                 105                 110

Gly Lys Asn Arg Glu Asp Ser Leu Ser Arg Trp Val Pro Asn Leu Pro
        115                 120                 125

Gln Arg Phe Gly Arg Thr Thr Thr Ala Lys Ser Ile Thr Lys Thr Leu
    130                 135                 140

Ser Asn Leu Leu Gln Gln Ser Met His Ser Pro Ser Thr Asn Gly Leu
145                 150                 155                 160

Leu Tyr Ser Met Ala Cys Gln Pro Gln Glu Ile Gln Asn Pro Gly Gln
                165                 170                 175

Lys Asn Leu Arg Arg Arg Gly Phe Gln Lys Ile Asp Asp Ala Glu Leu
            180                 185                 190

Lys Gln Glu Lys
        195

-continued

<210> SEQ ID NO 15
<211> LENGTH: 588
<212> TYPE: DNA
<213> ORGANISM: Bovine

<400> SEQUENCE: 15

```
atggaaatta tttcattaaa acgattcatt ttattgatgt tagccacttc aagcttgtta      60
acatcaaaca tcttctgcac agacgaatca aggatgccca atctttacag caaaaagaat     120
tatgacaaat attccgagcc tagaggagat ctaggctggg agaaagaaag aagtcttact     180
tttgaagaag taaagattg ggctccaaaa attaagatga ataaacctgt agtcaacaaa      240
atgccacctt ctgcagccaa cctgccactg agatttggga ggaacatgga agaagaaagg     300
agcactaggg cgatggccca cctgcctctg agactcggaa aaatagaga ggacagcctc      360
tccagatggg tcccaaatct gccccagagg tttggaagaa caacaacagc caaaagcatt     420
accaagaccc tgagtaattt gctccagcag tccatgcatt caccatctac caatgggcta     480
ctctactcca tggcctgcca gccccaagaa atccagaatc ctggtcaaaa gaacctaagg     540
agacggggat ccagaaaaat agatgatgca gaattgaaac aagaaaaa                  588
```

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16

```
ccctgggcct tcttctgtct tctatgt                                          27
```

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17

```
agcgattcat tttattgact ttagca                                           26
```

<210> SEQ ID NO 18
<211> LENGTH: 203
<212> TYPE: PRT
<213> ORGANISM: Rat

<400> SEQUENCE: 18

```
Met Glu Ile Ile Ser Ser Lys Arg Phe Ile Leu Leu Thr Leu Ala Thr
 1               5                  10                  15

Ser Ser Phe Leu Thr Ser Asn Thr Leu Cys Ser Asp Glu Leu Met Met
                20                  25                  30

Pro His Phe His Ser Lys Glu Gly Tyr Gly Lys Tyr Tyr Gln Leu Arg
            35                  40                  45

Gly Ile Pro Lys Gly Val Lys Glu Arg Ser Val Thr Phe Gln Glu Leu
        50                  55                  60

Lys Asp Trp Gly Ala Lys Lys Asp Ile Lys Met Ser Pro Ala Pro Ala
 65                  70                  75                  80

Asn Lys Val Pro His Ser Ala Ala Asn Leu Pro Leu Arg Phe Gly Arg
                85                  90                  95

Asn Ile Glu Asp Arg Arg Ser Pro Arg Ala Arg Ala Asn Met Glu Ala
            100                 105                 110
```

```
Gly Thr Met Ser His Phe Pro Ser Leu Pro Gln Arg Phe Gly Arg Thr
        115                 120                 125

Thr Ala Arg Arg Ile Thr Lys Thr Leu Ala Gly Leu Pro Gln Lys Ser
130                 135                 140

Leu His Ser Leu Ala Ser Ser Glu Ser Leu Tyr Ala Met Thr Arg Gln
145                 150                 155                 160

His Gln Glu Ile Gln Ser Pro Gly Gln Glu Pro Arg Lys Arg Val
                165                 170                 175

Phe Thr Glu Thr Asp Asp Ala Glu Arg Lys Gln Glu Lys Ile Gly Asn
                180                 185                 190

Leu Gln Pro Val Leu Gln Gly Ala Met Lys Leu
        195                 200
```

<210> SEQ ID NO 19
<211> LENGTH: 609
<212> TYPE: DNA
<213> ORGANISM: Rat

<400> SEQUENCE: 19

```
atggaaatta tttcatcaaa gcgattcatt ttattgactt tagcaacttc aagcttctta      60
acttcaaaca cccttttgttc agatgaatta atgatgcccc attttcacag caaagaaggt    120
tatgaaaat attaccagct gagaggaatc ccaaaagggg taaaggaaag aagtgtcact     180
tttcaagaac tcaaagattg gggggcaaag aaagatatta agatgagtcc agcccctgcc   240
aacaaagtgc cccactcagc agccaacctt ccctgaggt tgggaggaa catagaagac    300
agaagaagcc ccagggcacg ggccaacatg gaggcaggga ccatgagcca ttttcccagc    360
ctgcccaaa ggtttgggag aacaacagcc agacgcatca ccaagacact ggctggtttg    420
ccccagaaat ccctgcactc cctggcctcc agtgaatcgc tctatgccat gacccgccag    480
catcaagaaa ttcagagtcc tggtcaagag caacctagga acgggtgtt cacgaaaaca    540
gatgatgcag aaaggaaaca agaaaaaata ggaaacctcc agccagtcct tcaaggggct    600
atgaagctg                                                             609
```

<210> SEQ ID NO 20
<211> LENGTH: 12
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a, c, g or t
<220> FEATURE:
<221> NAME/KEY: misc_feature
<222> LOCATION: (9)..(9)
<223> OTHER INFORMATION: a, c, g or t

<400> SEQUENCE: 20

```
mgnttyggna ar                                                          12
```

<210> SEQ ID NO 21
<211> LENGTH: 12
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a, c, g or t
<220> FEATURE:
<221> NAME/KEY: misc_feature
<222> LOCATION: (9)..(9)

-continued

<223> OTHER INFORMATION: a, c, g or t
<220> FEATURE:
<221> NAME/KEY: misc_feature
<222> LOCATION: (12)..(12)
<223> OTHER INFORMATION: a, c, g or t

<400> SEQUENCE: 21
mgnttyggnm gn                                                           12

<210> SEQ ID NO 22
<211> LENGTH: 12
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a, c, g or t
<220> FEATURE:
<221> NAME/KEY: misc_feature
<222> LOCATION: (6)..(6)
<223> OTHER INFORMATION: a, c, g or t
<220> FEATURE:
<221> NAME/KEY: misc_feature
<222> LOCATION: (9)..(9)
<223> OTHER INFORMATION: a, c, g or t

<400> SEQUENCE: 22
mgnwsnggna ar                                                           12

<210> SEQ ID NO 23
<211> LENGTH: 12
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a, c, g or t
<220> FEATURE:
<221> NAME/KEY: misc_feature
<222> LOCATION: (6)..(6)
<223> OTHER INFORMATION: a, c, g or t
<220> FEATURE:
<221> NAME/KEY: misc_feature
<222> LOCATION: (9)..(9)
<223> OTHER INFORMATION: a, c, g or t
<220> FEATURE:
<221> NAME/KEY: misc_feature
<222> LOCATION: (12)..(12)
<223> OTHER INFORMATION: a, c, g or t

<400> SEQUENCE: 23
mgnwsnggnm gn                                                           12

<210> SEQ ID NO 24
<211> LENGTH: 12
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a, c, g or t
<220> FEATURE:
<221> NAME/KEY: misc_feature
<222> LOCATION: (6)..(6)
<223> OTHER INFORMATION: a, c, g or t
<220> FEATURE:
<221> NAME/KEY: misc_feature
<222> LOCATION: (9)..(9)
<223> OTHER INFORMATION: a, c, g or t

<400> SEQUENCE: 24
mgnytnggna ar                                                           12

```
<210> SEQ ID NO 25
<211> LENGTH: 12
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: a, c, g or t
<220> FEATURE:
<221> NAME/KEY: misc_feature
<222> LOCATION: (6)..(6)
<223> OTHER INFORMATION: a, c, g or t
<220> FEATURE:
<221> NAME/KEY: misc_feature
<222> LOCATION: (9)..(9)
<223> OTHER INFORMATION: a, c, g or t
<220> FEATURE:
<221> NAME/KEY: misc_feature
<222> LOCATION: (12)..(12)
<223> OTHER INFORMATION: a, c, g or t

<400> SEQUENCE: 25
mgnytnggnm gn                                                         12

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
gacttaattt tagatttaga caaaatggaa                                      30

<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27
ttctcccaaa cctttggggc aggtt                                           25

<210> SEQ ID NO 28
<211> LENGTH: 28
<212> TYPE: DNA
<213> ORGANISM: Artificial Sequence
<220> FEATURE:
<223> OTHER INFORMATION: primer

<400> SEQUENCE: 28
acagcaaaga aggtgacgga aaatactc                                        28

<210> SEQ ID NO 29
<211> LENGTH: 28
<212> TYPE: DNA
<213> ORGANISM: Artificial Sequence
<220> FEATURE:
<223> OTHER INFORMATION: primer

<400> SEQUENCE: 29
atagatgaga aaagaagccc cgcagcac                                        28

<210> SEQ ID NO 30
<211> LENGTH: 28
<212> TYPE: DNA
```

```
<213> ORGANISM: Artificial Sequence
<220> FEATURE:
<223> OTHER INFORMATION: primer

<400> SEQUENCE: 30
gtgctgcggg gcttcttttc tcatctat                                            28

<210> SEQ ID NO 31
<211> LENGTH: 21
<212> TYPE: DNA
<213> ORGANISM: Artificial  Sequence
<220> FEATURE:
<223> OTHER INFORMATION: primer

<400> SEQUENCE: 31
tttagactta gacgaaatgg a                                                   21

<210> SEQ ID NO 32
<211> LENGTH: 21
<212> TYPE: DNA
<213> ORGANISM: Artificial  Sequence
<220> FEATURE:
<223> OTHER INFORMATION: primer

<400> SEQUENCE: 32
gctccgtagc ctcttgaagt c                                                   21

<210> SEQ ID NO 33
<211> LENGTH: 188
<212> TYPE: PRT
<213> ORGANISM: Mouse

<400> SEQUENCE: 33
```

Met Glu Ile Ile Ser Leu Lys Arg Phe Ile Leu Thr Val Ala Thr
 1               5                  10                  15

Ser Ser Phe Leu Thr Ser Asn Thr Phe Cys Thr Asp Glu Phe Met Met
            20                  25                  30

Pro His Phe His Ser Lys Glu Gly Asp Gly Lys Tyr Ser Gln Leu Arg
        35                  40                  45

Gly Ile Pro Lys Gly Glu Lys Glu Arg Ser Val Ser Phe Gln Glu Leu
    50                  55                  60

Lys Asp Trp Gly Ala Lys Asn Val Ile Lys Met Ser Pro Ala Pro Ala
65                  70                  75                  80

Asn Lys Val Pro His Ser Ala Ala Asn Leu Pro Leu Arg Phe Gly Arg
                85                  90                  95

Thr Ile Asp Glu Lys Arg Ser Pro Ala Ala Arg Val Asn Met Glu Ala
            100                 105                 110

Gly Thr Arg Ser His Phe Pro Ser Leu Pro Gln Arg Phe Gly Arg Thr
        115                 120                 125

Thr Ala Arg Ser Pro Lys Thr Pro Ala Asp Leu Pro Gln Lys Pro Leu
    130                 135                 140

His Ser Leu Gly Ser Ser Glu Leu Leu Tyr Val Met Ile Cys Gln His
145                 150                 155                 160

Gln Glu Ile Gln Ser Pro Gly Gly Lys Arg Thr Arg Arg Gly Ala Phe
                165                 170                 175

Val Glu Thr Asp Asp Ala Glu Arg Lys Pro Glu Lys
            180                 185

```
<210> SEQ ID NO 34
<211> LENGTH: 564
```

-continued

```
<212> TYPE: DNA
<213> ORGANISM: Mouse

<400> SEQUENCE: 34
atggaaatta tttcattaaa acgattcatt ttattgactg tggcaacttc aagcttctta      60
acatcaaaca ccttctgtac agatgagttc atgatgcctc attttcacag caaagaaggt     120
gacgaaaaat actcccagct gagaggaatc ccaaaagggg aaaaggaaag aagtgtcagt     180
tttcaagaac taaaagattg gggggcaaag aatgttatta agatgagtcc agcccctgcc     240
aacaaagtgc cccactcagc agccaacctg cccctgagat tggaaggac catagatgag      300 aaaagaagcc ccgcagcacg ggtcaacatg gaggcaggga ccaggagcca tttccccagc     360
ctgccccaaa ggtttgggag aacaacagcc agaagcccca agacaccggc tgatttgcca     420
cagaaacccc tgcactcact gggctccagc gagttgctct acgtcatgat ctgccagcac     480
caagaaattc agagtcctgg tggaaagcga acgaggagag gagcgtttgt ggaaacagat     540
gatgcagaaa ggaaaccaga aaaa                                             564

<210> SEQ ID NO 35
<211> LENGTH: 27
<212> TYPE: DNA
<213> ORGANISM: Artificial  Sequence
<220> FEATURE:
<223> OTHER INFORMATION: primer

<400> SEQUENCE: 35
agtcgacagt atggaggcgg agccctc                                           27

<210> SEQ ID NO 36
<211> LENGTH: 29
<212> TYPE: DNA
<213> ORGANISM: Artificial  Sequence
<220> FEATURE:
<223> OTHER INFORMATION: primer

<400> SEQUENCE: 36
gactagttca aatgttccag gccgggatg                                          29

<210> SEQ ID NO 37
<211> LENGTH: 432
<212> TYPE: PRT
<213> ORGANISM: Rat

<400> SEQUENCE: 37

Met Glu Ala Glu Pro Ser Gln Pro Pro Asn Gly Ser Trp Pro Leu Gly
 1               5                  10                  15

Gln Asn Gly Ser Asp Val Glu Thr Ser Met Ala Thr Ser Leu Thr Phe
             20                  25                  30

Ser Ser Tyr Tyr Gln His Ser Ser Pro Val Ala Ala Met Phe Ile Ala
         35                  40                  45

Ala Tyr Val Leu Ile Phe Leu Leu Cys Met Val Gly Asn Thr Leu Val
     50                  55                  60

Cys Phe Ile Val Leu Lys Asn Arg His Met Arg Thr Val Thr Asn Met
 65                  70                  75                  80

Phe Ile Leu Asn Leu Ala Val Ser Asp Leu Leu Val Gly Ile Phe Cys
                 85                  90                  95

Met Pro Thr Thr Leu Val Asp Asn Leu Ile Thr Gly Trp Pro Phe Asp
            100                 105                 110

Asn Ala Thr Cys Lys Met Ser Gly Leu Val Gln Gly Met Ser Val Ser
```

```
            115                 120                 125
Ala Ser Val Phe Thr Leu Val Ala Ile Ala Val Glu Arg Phe Arg Cys
    130                 135                 140

Ile Val His Pro Phe Arg Glu Lys Leu Thr Leu Arg Lys Ala Leu Phe
145                 150                 155                 160

Thr Ile Ala Val Ile Trp Ala Leu Ala Leu Leu Ile Met Cys Pro Ser
                165                 170                 175

Ala Val Thr Leu Thr Val Thr Arg Glu Glu His Phe Met Leu Asp
            180                 185                 190

Ala Arg Asn Arg Ser Tyr Pro Leu Tyr Ser Cys Trp Glu Ala Trp Pro
            195                 200                 205

Glu Lys Gly Met Arg Lys Val Tyr Thr Ala Val Leu Phe Ala His Ile
            210                 215                 220

Tyr Leu Val Pro Leu Ala Leu Ile Val Val Met Tyr Val Arg Ile Ala
225                 230                 235                 240

Arg Lys Leu Cys Gln Ala Pro Gly Pro Ala Arg Asp Thr Glu Glu Ala
                245                 250                 255

Val Ala Glu Gly Gly Arg Thr Ser Arg Arg Ala Arg Val Val His
            260                 265                 270

Met Leu Val Met Val Ala Leu Phe Phe Thr Leu Ser Trp Leu Pro Leu
            275                 280                 285

Trp Val Leu Leu Leu Leu Ile Asp Tyr Gly Glu Leu Ser Glu Leu Gln
            290                 295                 300

Leu His Leu Leu Ser Val Tyr Ala Phe Pro Leu Ala His Trp Leu Ala
305                 310                 315                 320

Phe Phe His Ser Ser Ala Asn Pro Ile Ile Tyr Gly Tyr Phe Asn Glu
                325                 330                 335

Asn Phe Arg Arg Gly Phe Gln Ala Ala Phe Arg Ala Gln Leu Cys Trp
            340                 345                 350

Pro Pro Trp Ala Ala His Lys Gln Ala Tyr Ser Glu Arg Pro Asn Arg
            355                 360                 365

Leu Leu Arg Arg Arg Val Val Val Asp Val Gln Pro Ser Asp Ser Gly
370                 375                 380

Leu Pro Ser Glu Ser Gly Pro Ser Ser Gly Val Pro Gly Pro Gly Arg
385                 390                 395                 400

Leu Pro Leu Arg Asn Gly Arg Val Ala His Gln Asp Gly Pro Gly Glu
                405                 410                 415

Gly Pro Gly Cys Asn His Met Pro Leu Thr Ile Pro Ala Trp Asn Ile
                420                 425                 430

<210> SEQ ID NO 38
<211> LENGTH: 1299
<212> TYPE: DNA
<213> ORGANISM: Rat

<400> SEQUENCE: 38
atggaggcgg agccctccca gcctcccaac ggcagctggc ccctgggtca gaacgggagt      60
gatgtggaga ccagcatggc aaccagcctc accttctcct cctactacca acactcctct     120
ccggtggcag ccatgttcat cgcggcctac gtgctcatct cctcctctg catggtgggc     180 aacaccctgg tctgcttcat tgtgctcaag aaccggcaca tgcgcactgt caccaacatg     240
tttatcctca acctgccgt cagcgacctg ctggtgggca tcttctgcat gcccacaacc     300
cttgtggaca accttatcac tggttggcct tttgacaacg ccacatgcaa gatgagcggc     360
```

```
ttggtgcagg gcatgtccgt gtctgcatcg gttttcacac tggtggccat cgctgtggaa    420
aggttccgct gcatcgtgca cccttccgc gagaagctga cccttcggaa ggcgctgttc     480
accatcgcgg tgatctgggc tctggcgctg ctcatcatgt gtccctcggc ggtcactctg    540
acagtcaccc gagaggagca tcacttcatg ctggatgctc gtaaccgctc ctacccgctc    600
tactcgtgct gggaggcctg gcccgagaag gcatgcgca aggtctacac cgcggtgctc     660
ttcgcgcaca tctacctggt gccgctggcg ctcatcgtag tgatgtacgt gcgcatcgcg    720
cgcaagctat gccaggcccc cggtcctgcg cgcgacacgg aggaggcggt ggccgagggt    780
ggccgcactt cgcgccgtag ggcccgcgtg gtgcacatgc tggtcatggt ggcgctcttc    840
ttcacgttgt cctggctgcc actctgggtg ctgctgctgc tcatcgacta tggggagctg    900
agcgagctgc aactgcacct gctgtcggtc tacgccttcc ccttggcaca ctggctggcc    960
ttcttccaca gcagcgccaa ccccatcatc tacggctact caacgagaa cttccgccgc    1020 ggcttccagg ctgccttccg tgcacagctc tgctggcctc cctgggccgc ccacaagcaa    1080
gcctactcgg agcggcccaa ccgcctcctg cgcaggcggg tggtggtgga cgtgcaaccc    1140
agcgactccg gcctgccatc agagtctggc cccagcagcg gggtcccagg gcctggccgg    1200
ctgccactgc gcaatgggcg tgtggcccat caggatggcc cggggaagg gccaggctgc     1260 aaccacatgc ccctcaccat cccggcctgg aacatttga                           1299
```

<210> SEQ ID NO 39
<211> LENGTH: 12
<212> TYPE: PRT
<213> ORGANISM: Artificial Sequence
<220> FEATURE:
<223> OTHER INFORMATION: the C-terminus of the polypeptide is amide
       (-CONH2) form

<400> SEQUENCE: 39

Met Pro His Ser Phe Ala Asn Leu Pro Leu Arg Phe
  1               5                  10

<210> SEQ ID NO 40
<211> LENGTH: 8
<212> TYPE: PRT
<213> ORGANISM: Artificial Sequence
<220> FEATURE:
<223> OTHER INFORMATION: the C-terminus of the polypeptide is amide
       (-CONH2) form

<400> SEQUENCE: 40

Val Pro Asn Leu Pro Gln Arg Phe
  1               5

<210> SEQ ID NO 41
<211> LENGTH: 11
<212> TYPE: PRT
<213> ORGANISM: Artificial Sequence
<220> FEATURE:
<223> OTHER INFORMATION: the C-terminus of the polypeptide is amide
       (-CONH2) form

<400> SEQUENCE: 41

Ser Ala Gly Ala Thr Ala Asn Leu Pro Arg Ser
  1               5                  10

<210> SEQ ID NO 42
<211> LENGTH: 36
<212> TYPE: DNA
<213> ORGANISM: Human

<400> SEQUENCE: 42
atgccacact ccttcgccaa cttgccattg agattt                                    36

<210> SEQ ID NO 43
<211> LENGTH: 36
<212> TYPE: DNA
<213> ORGANISM: Human

<400> SEQUENCE: 43
agtgctggag caacagccaa cctgcctctg agatct                                    36

<210> SEQ ID NO 44
<211> LENGTH: 24
<212> TYPE: DNA
<213> ORGANISM: Human

<400> SEQUENCE: 44
gttcctaacc tgccccaaag gttt                                                 24

<210> SEQ ID NO 45
<211> LENGTH: 276
<212> TYPE: DNA
<213> ORGANISM: Human

<400> SEQUENCE: 45
atggaaatta tttcatcaaa actattcatt ttattgactt tagccacttc aagcttgtta          60
acatcaaaca ttttttgtgc agatgaatta gtgatgtcca atcttcacag caaagaaaat        120
tatgacaaat attctgagcc tagaggatac ccaaaagggg aaagaagcct caattttgag        180
gaattaaaag attggggacc aaaaaatgtt attaagatga gtacacctgc agtcaataaa        240
atgccacact ccttcgccaa cttgccattg agattt                                  276

<210> SEQ ID NO 46
<211> LENGTH: 336
<212> TYPE: DNA
<213> ORGANISM: Human

<400> SEQUENCE: 46
atggaaatta tttcatcaaa actattcatt ttattgactt tagccacttc aagcttgtta          60
acatcaaaca ttttttgtgc agatgaatta gtgatgtcca atcttcacag caaagaaaat        120
tatgacaaat attctgagcc tagaggatac ccaaaagggg aaagaagcct caattttgag        180
gaattaaaag attggggacc aaaaaatgtt attaagatga gtacacctgc agtcaataaa        240
atgccacact ccttcgccaa cttgccattg agatttggga ggaacgttca agaagaaga         300 agtgctggag caacagccaa cctgcctctg agatct                                  336

<210> SEQ ID NO 47
<211> LENGTH: 393
<212> TYPE: DNA
<213> ORGANISM: Human

<400> SEQUENCE: 47
atggaaatta tttcatcaaa actattcatt ttattgactt tagccacttc aagcttgtta          60
acatcaaaca ttttttgtgc agatgaatta gtgatgtcca atcttcacag caaagaaaat        120
tatgacaaat attctgagcc tagaggatac ccaaaagggg aaagaagcct caattttgag        180
gaattaaaag attggggacc aaaaaatgtt attaagatga gtacacctgc agtcaataaa        240

-continued

```
atgccacact ccttcgccaa cttgccattg agatttggga ggaacgttca agaagaaaga    300
agtgctggag caacagccaa cctgcctctg agatctggaa agaaatatgga ggtgagcctc   360 gtgagacgtg ttcctaacct gccccaaagg ttt                                 393
```

<210> SEQ ID NO 48
<211> LENGTH: 27
<212> TYPE: DNA
<213> ORGANISM: Artificial Sequence
<220> FEATURE:
<223> OTHER INFORMATION: primer

<400> SEQUENCE: 48

```
ccctggggct tcttctgtct tctatgt                                        27
```

<210> SEQ ID NO 49
<211> LENGTH: 26
<212> TYPE: DNA
<213> ORGANISM: Artificial Sequence
<220> FEATURE:
<223> OTHER INFORMATION: primer

<400> SEQUENCE: 49

```
agcgattcat tttattgact ttagca                                         26
```

<210> SEQ ID NO 50
<211> LENGTH: 203
<212> TYPE: PRT
<213> ORGANISM: Rat

<400> SEQUENCE: 50

Met Glu Ile Ile Ser Ser Lys Arg Phe Ile Leu Leu Thr Leu Ala Thr
 1               5                  10                  15

Ser Ser Phe Leu Thr Ser Asn Thr Leu Cys Ser Asp Glu Leu Met Met
             20                  25                  30

Pro His Phe His Ser Lys Glu Gly Tyr Gly Lys Tyr Tyr Gln Leu Arg
         35                  40                  45

Gly Ile Pro Lys Gly Val Lys Glu Arg Ser Val Thr Phe Gln Glu Leu
     50                  55                  60

Lys Asp Trp Gly Ala Lys Lys Asp Ile Lys Met Ser Pro Ala Pro Ala
 65                  70                  75                  80

Asn Lys Val Pro His Ser Ala Ala Asn Leu Pro Leu Arg Phe Gly Arg
                 85                  90                  95

Asn Ile Glu Asp Arg Arg Ser Pro Arg Ala Arg Ala Asn Met Glu Ala
            100                 105                 110

Gly Thr Met Ser His Phe Pro Ser Leu Pro Gln Arg Phe Gly Arg Thr
        115                 120                 125

Thr Ala Arg Arg Ile Thr Lys Thr Leu Ala Gly Leu Pro Gln Lys Ser
    130                 135                 140

Leu His Ser Leu Ala Ser Ser Glu Leu Leu Tyr Ala Met Thr Arg Gln
145                 150                 155                 160

His Gln Glu Ile Gln Ser Pro Gly Gln Glu Pro Arg Lys Arg Val
                165                 170                 175

Phe Thr Glu Thr Asp Asp Ala Glu Arg Lys Gln Glu Lys Ile Gly Asn
            180                 185                 190

Leu Gln Pro Val Leu Gln Gly Ala Met Lys Leu
        195                 200

<210> SEQ ID NO 51

```
<211> LENGTH: 609
<212> TYPE: DNA
<213> ORGANISM: Rat

<400> SEQUENCE: 51
atggaaatta tttcatcaaa gcgattcatt ttattgactt tagcaacttc aagcttctta      60
acttcaaaca ccctttgttc agatgaatta atgatgcccc attttcacag caaagaaggt     120
tatggaaaat attaccagct gagaggaatc ccaaaagggg taaggaaaag aagtgtcact     180
tttcaagaac tcaaagattg gggggcaaag aaagatatta agatgagtcc agcccctgcc     240
aacaaagtgc cccactcagc agccaacctt cccctgaggt ttgggaggaa catagaagac     300
agaagaagcc cagggcacg ggccaacatg gaggcaggga ccatgagcca ttttcccagc      360
ctgccccaaa ggtttgggag aacaacagcc agacgcatca ccaagacact ggctggtttg     420
ccccagaaat ccctgcactc cctggcctcc agtgaattgc tctatgccat gacccgccag     480
catcaagaaa ttcagagtcc tggtcaagag caacctagga acgggtgtt cacgaaaaca      540
gatgatgcag aaaggaaaca agaaaaaata ggaaacctcc agccagtcct tcaaggggct     600
atgaagctg                                                              609

<210> SEQ ID NO 52
<211> LENGTH: 27
<212> TYPE: DNA
<213> ORGANISM: Artificial Sequence
<220> FEATURE:
<223> OTHER INFORMATION: primer

<400> SEQUENCE: 52
ttctagattt tggacaaaat ggaaatt                                          27

<210> SEQ ID NO 53
<211> LENGTH: 27
<212> TYPE: DNA
<213> ORGANISM: Artificial Sequence
<220> FEATURE:
<223> OTHER INFORMATION: primer

<400> SEQUENCE: 53
cgtctttagg gacaggctcc agatttc                                          27

<210> SEQ ID NO 54
<211> LENGTH: 430
<212> TYPE: PRT
<213> ORGANISM: Human

<400> SEQUENCE: 54
```

Met Glu Gly Glu Pro Ser Gln Pro Pro Asn Ser Ser Trp Pro Leu Ser
1               5                   10                  15

Gln Asn Gly Thr Asn Thr Glu Ala Thr Pro Ala Thr Asn Leu Thr Phe
            20                  25                  30

Ser Ser Tyr Tyr Gln His Thr Ser Pro Val Ala Ala Met Phe Ile Val
        35                  40                  45

Ala Tyr Ala Leu Ile Phe Leu Leu Cys Met Val Gly Asn Thr Leu Val
    50                  55                  60

Cys Phe Ile Val Leu Lys Asn Arg His Met His Thr Val Thr Asn Met
65                  70                  75                  80

Phe Ile Leu Asn Leu Ala Val Ser Asp Leu Leu Val Gly Ile Phe Cys
                85                  90                  95

Met Pro Thr Thr Leu Val Asp Asn Leu Ile Thr Gly Trp Pro Phe Asp

```
               100                 105                 110
Asn Ala Thr Cys Lys Met Ser Gly Leu Val Gln Gly Met Ser Val Ser
            115                 120                 125

Ala Ser Val Phe Thr Leu Val Ala Ile Ala Val Glu Arg Phe Arg Cys
        130                 135                 140

Ile Val His Pro Phe Arg Glu Lys Leu Thr Leu Arg Lys Ala Leu Val
145                 150                 155                 160

Thr Ile Ala Val Ile Trp Ala Leu Ala Leu Leu Ile Met Cys Pro Ser
                165                 170                 175

Ala Val Thr Leu Thr Val Thr Arg Glu Glu His His Phe Met Val Asp
            180                 185                 190

Ala Arg Asn Arg Ser Tyr Pro Leu Tyr Ser Cys Trp Glu Ala Trp Pro
        195                 200                 205

Glu Lys Gly Met Arg Arg Val Tyr Thr Thr Val Leu Phe Ser His Ile
    210                 215                 220

Tyr Leu Ala Pro Leu Ala Leu Ile Val Val Met Tyr Ala Arg Ile Ala
225                 230                 235                 240

Arg Lys Leu Cys Gln Ala Pro Gly Pro Ala Pro Gly Gly Glu Glu Ala
                245                 250                 255

Ala Asp Pro Arg Ala Ser Arg Arg Ala Arg Val Val His Met Leu
            260                 265                 270

Val Met Val Ala Leu Phe Phe Thr Leu Ser Trp Leu Pro Leu Trp Ala
        275                 280                 285

Leu Leu Leu Leu Ile Asp Tyr Gly Gln Leu Ser Ala Pro Gln Leu His
    290                 295                 300

Leu Val Thr Val Tyr Ala Phe Pro Phe Ala His Trp Leu Ala Phe Phe
305                 310                 315                 320

Asn Ser Ser Ala Asn Pro Ile Ile Tyr Gly Tyr Phe Asn Glu Asn Phe
                325                 330                 335

Arg Arg Gly Phe Gln Ala Ala Phe Arg Ala Arg Leu Cys Pro Arg Pro
            340                 345                 350

Ser Gly Ser His Lys Glu Ala Tyr Ser Glu Arg Pro Gly Gly Leu Leu
        355                 360                 365

His Arg Arg Val Phe Val Val Arg Pro Ser Asp Ser Gly Leu Pro
    370                 375                 380

Ser Glu Ser Gly Pro Ser Ser Gly Ala Pro Arg Pro Gly Arg Leu Pro
385                 390                 395                 400

Leu Arg Asn Gly Arg Val Ala His His Gly Leu Pro Arg Glu Gly Pro
                405                 410                 415

Gly Cys Ser His Leu Pro Leu Thr Ile Pro Ala Trp Asp Ile
            420                 425                 430

<210> SEQ ID NO 55
<211> LENGTH: 1290
<212> TYPE: DNA
<213> ORGANISM: Human

<400> SEQUENCE: 55 atggagggg agccctccca gcctcccaac agcagttggc ccctaagtca gaatgggact      60
aacactgagg ccaccccggc tacaaacctc accttctcct cctactatca gcacacctcc    120
cctgtggcgg ccatgttcat tgtggcctat gcgctcatct tcctgctctg catggtgggc    180
aacaccctgg tctgtttcat cgtgctcaag aaccggcaca tgcatactgt caccaacatg    240
ttcatcctca acctggctgt cagtgacctg ctggtgggca tcttctgcat gcccaccacc    300
```

```
cttgtggaca acctcatcac tgggtggccc ttcgacaatg ccacatgcaa gatgagcggc    360
ttggtgcagg gcatgtctgt gtcggcttcc gttttcacac tggtggccat tgctgtggaa    420
aggttccgct gcatcgtgca ccctttccgc gagaagctga ccctgcggaa ggcgctcgtc    480
accatcgccg tcatctgggc cctggcgctg ctcatcatgt gtccctcggc cgtcacgctg    540
accgtcaccc gtgaggagca ccacttcatg gtggacgccc gcaaccgctc ctaccctctc    600
tactcctgct gggaggcctg gcccgagaag ggcatgcgca gggtctacac cactgtgctc    660
ttctcgcaca tctacctggc gccgctggcg ctcatcgtgg tcatgtacgc ccgcatcgcg    720
cgcaagctct gccaggcccc gggcccggcc cccggggggcg aggaggctgc ggaccccgcga   780 gcatcgcggc gcagagcgcg cgtggtgcac atgctggtca tggtggcgct gttcttcacg    840
ctgtcctggc tgccgctctg ggcgctgctg ctgctcatcg actacgggca gctcagcgcg    900
ccgcagctgc acctggtcac cgtctacgcc ttccccttcg cgcactggct ggccttcttc    960
aacagcagcg ccaaccccat catctacggc tacttcaacg agaacttccg ccgcggcttc   1020
caggccgcct tccgcgcccg cctctgcccg cgcccgtcgg ggagccacaa ggaggcctac   1080
tccgagcggc ccggcgggct tctgcacagg cgggtcttcg tggtggtgcg gcccagcgac   1140
tccgggctgc cctctgagtc gggccctagc agtggggccc ccaggcccgg ccgcctcccg   1200
ctgcggaatg ggcgggtggc tcaccacggc ttgcccaggg aagggcctgg ctgctcccac   1260
ctgcccctca ccattccagc ctgggatatc                                    1290

<210> SEQ ID NO 56
<211> LENGTH: 1290
<212> TYPE: DNA
<213> ORGANISM: Human

<400> SEQUENCE: 56
atggaggggg agccctccca gcctcccaac agcagttggc ccctaagtca gaatgggact     60
aacactgagg ccaccccggc tacaaacctc accttctcct cctactatca gcacacctcc    120
cctgtggcgg ccatgttcat tgtggcctat gcgctcatct cctgctctg catggtgggc     180 aacaccctgg tctgtttcat cgtgctcaag aaccggcaca tgcatactgt caccaacatg    240
ttcatcctca acctggctgt cagtgacctg ctggtgggca tcttctgcat gcccaccacc    300
cttgtggaca acctcatcac tgggtggccc ttcgacaatg ccacatgcaa gatgagcggc    360
ttggtgcagg gcatgtctgt gtcggcttcc gttttcacac tggtggccat tgctgtggaa    420
aggttccgct gcatcgtgca ccctttccgc gagaagctga ccctgcggaa ggcgctcgtc    480
accatcgccg tcatctgggc cctggcgctg ctcatcatgt gtccctcggc cgtcacgctg    540
accgtcaccc gtgaggagca ccacttcatg gtggacgccc gcaaccgctc ctaccctctc    600
tactcctgct gggaggcctg gcccgagaag ggcatgcgca gggtctacac cactgtgctc    660
ttctcgcaca tctacctggc gccgctggcg ctcatcgtgg tcatgtacgc ccgcatcgcg    720
cgcaagctct gccaggcccc gggcccggcc cccggggggcg aggaggctgc ggaccccgcga   780 gcatcgcggc gcagagcgcg cgtggtgcac atgctggtca tggtggcgct gttcttcacg    840
ctgtcctggc tgccgctctg ggcgctgctg ctgctcatcg actacgggca gctcagcgcg    900
ccgcagctgc acctggtcac cgtctacgcc ttccccttcg cgcactggct ggccttcttc    960
aacagcagcg ccaaccccat catctacggc tacttcaacg agaacttccg ccgcggcttc   1020
caggccgcct tccgcgcccg cctctgcccg cgcccgtcgg ggagccacaa ggaggcctac   1080
```

```
tccgagcggc cggcgggct tctgcacagg cgggtcttcg tggtggtgcg gcccagcgac    1140
tccgggctgc cctctgagtc gggccctagc agtgggcccc ccaggcccgg ccgcctcccg    1200
ctgcggaatg ggcgggtggc tcaccacggc ttgcccaggg aagggcctgg ctgctcccac    1260
ctgcccctca ccattccagc ctgggatatc                                    1290
```

<210> SEQ ID NO 57
<211> LENGTH: 31
<212> TYPE: DNA
<213> ORGANISM: Artificial Sequence
<220> FEATURE:
<223> OTHER INFORMATION: primer

<400> SEQUENCE: 57

```
gtcgacatgg aggggagcc ctcccagcct c                                   31
```

<210> SEQ ID NO 58
<211> LENGTH: 29
<212> TYPE: DNA
<213> ORGANISM: Artificial Sequence
<220> FEATURE:
<223> OTHER INFORMATION: primer

<400> SEQUENCE: 58

```
actagttcag atatcccagg ctggaatgg                                     29
```

<210> SEQ ID NO 59
<211> LENGTH: 58
<212> TYPE: DNA
<213> ORGANISM: Artificial Sequence
<220> FEATURE:
<223> OTHER INFORMATION: Primer

<400> SEQUENCE: 59

```
tatgagcctg aactttgaag aactgaaaga ttggggtccg aaaaatgtga ttaaaatg    58
```

<210> SEQ ID NO 60
<211> LENGTH: 61
<212> TYPE: DNA
<213> ORGANISM: Artificial Sequence
<220> FEATURE:
<223> OTHER INFORMATION: Primer

<400> SEQUENCE: 60

```
agcaccccgg cggtgaataa aatgccgcat agctttgcga atctgccgct gcgttttgc    60 c                                                                   61
```

<210> SEQ ID NO 61
<211> LENGTH: 62
<212> TYPE: DNA
<213> ORGANISM: Artificial Sequence
<220> FEATURE:
<223> OTHER INFORMATION: Primer

<400> SEQUENCE: 61

```
ggtgctcatt ttaatcacat ttttcggacc ccaatctttc agttcttcaa agttcaggct    60
ca                                                                  62
```

<210> SEQ ID NO 62
<211> LENGTH: 59
<212> TYPE: DNA
<213> ORGANISM: Artificial Sequence
<220> FEATURE:
<223> OTHER INFORMATION: Primer

<400> SEQUENCE: 62
tcggggcaaa aacgcagcgg cagattcgca aagctatgcg gcattttatt caccgccgg    59

<210> SEQ ID NO 63
<211> LENGTH: 28
<212> TYPE: PRT
<213> ORGANISM: Human

<400> SEQUENCE: 63

Ala Thr Ala Asn Leu Pro Leu Arg Ser Gly Arg Asn Met Glu Val Ser
1               5                   10                  15

Leu Val Arg Arg Val Pro Asn Leu Pro Gln Arg Phe
            20                  25

<210> SEQ ID NO 64
<211> LENGTH: 84
<212> TYPE: DNA
<213> ORGANISM: Human

<400> SEQUENCE: 64
gcaacagcca acctgcctct gagatctgga agaaatatgg aggtgagcct cgtgagacgt    60
gttcctaacc tgccccaaag gttt                                          84

<210> SEQ ID NO 65
<211> LENGTH: 31
<212> TYPE: PRT
<213> ORGANISM: Human

<400> SEQUENCE: 65

Ser Ala Gly Ala Thr Ala Asn Leu Pro Leu Arg Ser Gly Arg Asn Met
1               5                   10                  15

Glu Val Ser Leu Val Arg Arg Val Pro Asn Leu Pro Gln Arg Phe
            20                  25                  30

<210> SEQ ID NO 66
<211> LENGTH: 93
<212> TYPE: DNA
<213> ORGANISM: Human

<400> SEQUENCE: 66
agtgctggag caacagccaa cctgcctctg agatctggaa gaaatatgga ggtgagcctc    60
gtgagacgtg ttcctaacct gccccaaagg ttt                                93

<210> SEQ ID NO 67
<211> LENGTH: 28
<212> TYPE: PRT
<213> ORGANISM: Bovine

<400> SEQUENCE: 67

Ala Met Ala His Leu Pro Leu Arg Leu Gly Lys Asn Arg Glu Asp Ser
1               5                   10                  15

Leu Ser Arg Trp Val Pro Asn Leu Pro Gln Arg Phe
            20                  25

<210> SEQ ID NO 68
<211> LENGTH: 84
<212> TYPE: DNA
<213> ORGANISM: Bovine

<400> SEQUENCE: 68

```
gcgatggccc acctgcctct gagactcgga aaaaatagag aggacagcct ctccagatgg     60
gtcccaaatc tgccccagag gttt                                           84
```

<210> SEQ ID NO 69
<211> LENGTH: 5
<212> TYPE: PRT
<213> ORGANISM: Artificial Sequence
<220> FEATURE:
<223> OTHER INFORMATION: Peptide

<400> SEQUENCE: 69

Leu Pro Gln Arg Phe
 1               5

<210> SEQ ID NO 70
<211> LENGTH: 6
<212> TYPE: PRT
<213> ORGANISM: Artificial Sequence
<220> FEATURE:
<223> OTHER INFORMATION: Peptide

<400> SEQUENCE: 70

Asn Leu Pro Gln Arg Phe
 1               5

<210> SEQ ID NO 71
<211> LENGTH: 7
<212> TYPE: PRT
<213> ORGANISM: Artificial Sequence
<220> FEATURE:
<223> OTHER INFORMATION: Peptide

<400> SEQUENCE: 71

Pro Asn Leu Pro Gln Arg Phe
 1               5

<210> SEQ ID NO 72
<211> LENGTH: 8
<212> TYPE: PRT
<213> ORGANISM: Artificial Sequence
<220> FEATURE:
<223> OTHER INFORMATION: Peptide

<400> SEQUENCE: 72

Val Pro Asn Leu Pro Gln Arg Phe
 1               5